(12) United States Patent
Roberge et al.

(10) Patent No.: US 12,427,165 B2
(45) Date of Patent: *Sep. 30, 2025

(54) PHARMACEUTICAL COMPOSITION

(71) Applicant: MedinCell S.A., Jacou (FR)

(72) Inventors: Christophe Roberge, Jacou (FR);
Adolfo López-Noriega, Jacou (FR);
Jean-Manuel Cros, Jacou (FR);
Juliette Serindoux, Jacou (FR);
Murielle Oster, Jacou (FR); Fang Liu, Jacou (FR); Charlotte Molinier, Jacou (FR); Sylvestre Grizot, Jacou (FR);
Tjasa Vrlinic, Jacou (FR); Feifei Ng, Jacou (FR); Elise Guégain, Jacou (FR);
Marie-Emérentienne Cagnon, Jacou (FR)

(73) Assignee: MEDINCELL S.A., Jacou (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,713

(22) Filed: May 2, 2024

(65) Prior Publication Data

US 2024/0293444 A1    Sep. 5, 2024

Related U.S. Application Data

(63) Continuation of application No. 17/421,602, filed as application No. PCT/EP2020/050333 on Jan. 8, 2020.

(30) Foreign Application Priority Data

Jan. 8, 2019  (GB) .................................. 1900258

(51) Int. Cl.
| | |
|---|---|
| A61K 9/00 | (2006.01) |
| A61K 31/445 | (2006.01) |
| A61K 31/4985 | (2006.01) |
| A61K 31/5415 | (2006.01) |
| A61K 31/675 | (2006.01) |
| A61K 31/7048 | (2006.01) |
| A61K 31/765 | (2006.01) |
| A61K 47/34 | (2017.01) |

(52) U.S. Cl.
CPC .......... *A61K 31/765* (2013.01); *A61K 9/0024* (2013.01); *A61K 31/445* (2013.01); *A61K 31/4985* (2013.01); *A61K 31/5415* (2013.01); *A61K 31/675* (2013.01); *A61K 31/7048* (2013.01); *A61K 47/34* (2013.01)

(58) Field of Classification Search
None
See application file for complete search history.

(56) References Cited

U.S. PATENT DOCUMENTS

| | | |
|---|---|---|
| 5,225,521 A | 7/1993 | Spinu |
| 6,350,812 B1 | 2/2002 | Vert et al. |
| 7,265,186 B2 | 9/2007 | Zhao |
| 8,557,535 B2 | 10/2013 | Pathak |
| 8,815,293 B2 | 8/2014 | Ahlheim et al. |
| 2005/0255091 A1 | 11/2005 | Loomis |
| 2011/0070320 A1 | 3/2011 | Hahn et al. |
| 2012/0172454 A1* | 7/2012 | Gaudriault ............. A01N 25/10 514/772.1 |
| 2015/0297729 A1 | 10/2015 | Ottoboni et al. |
| 2016/0058698 A1 | 3/2016 | Mayadunne et al. |
| 2020/0155449 A1 | 5/2020 | Gaudriault et al. |

FOREIGN PATENT DOCUMENTS

| | | |
|---|---|---|
| CN | 1413118 A | 4/2003 |
| CN | 1671362 A | 9/2005 |
| CN | 102432852 A | 5/2012 |
| CN | 104582733 A | 4/2015 |
| CN | 103976976 B | 5/2016 |
| CN | 106543454 A | 3/2017 |
| CN | 106832844 A | 6/2017 |
| CN | 108586775 A | 9/2018 |
| EP | 3 257 498 A1 | 12/2017 |
| WO | WO 01/35929 A2 | 5/2001 |
| WO | WO 01/45742 A1 | 6/2001 |
| WO | WO 2004/002456 A1 | 1/2004 |
| WO | WO 2008/066787 A2 | 6/2008 |
| WO | WO 2012/090070 A2 | 7/2012 |
| WO | WO 2014/001904 A1 | 1/2014 |
| WO | WO 2017/085561 A1 | 5/2017 |
| WO | WO 2019/016233 A1 | 1/2019 |
| WO | WO 2019/016234 A1 | 1/2019 |
| WO | WO 2019/016236 A1 | 1/2019 |

OTHER PUBLICATIONS

Lin et al., J. Appl. Poly. Sci., 2012, 124(6), pp. 4496-4501 (Year: 2012).*
Zhang et al., Biomacromol., 2006, 7(4), pp. 1139-1146 (Year: 2006).*
Lemmouchi et al., J. Poly. Sci. A, 2007, vol. 45, pp. 3966-3974 (Year: 2007).*
Gu et al., J. Mater. Chem. B, 2015, vol. 3, pp. 316-322 (Year: 2015).*
Breitenbach et al., "Branched Biodegradable Polyesters for Parenteral Drug Delivery Systems," Journal of Controlled Release, vol. 64, 2000, pp. 167-178.
Burke et al., "The Effect of Branching (Star Architecture) on poly(D,L-lactide) (PDLLA) Degradation and Drug Delivery," Biomacromolecules, vol. 18, 2017 (Publication Date on Web: Dec. 8, 2016), pp. 1-34 (total 35 pages).

(Continued)

*Primary Examiner* — Brian Gulledge
(74) *Attorney, Agent, or Firm* — Birch, Stewart, Kolasch & Birch, LLP

(57) ABSTRACT

The present invention provides a pharmaceutical composition comprising:
a biodegradable multi-branched copolymer comprising at least three polyester arms attached to a central core which comprises a polyether, and wherein the multi-branched copolymer is substantially insoluble in aqueous solution, further comprising at least one pharmaceutically active ingredient.

27 Claims, 51 Drawing Sheets

(56) References Cited

OTHER PUBLICATIONS

Buwalda et al., "Influence of Amide versus Ester Linkages on the Properties of Eight-Armed PEG-PLA Star Block Copolymer Hydrogels," Biomacromolecules, vol. 11, No. 1, 2010 (Published on Web Nov. 25, 2009), doi:10.1021/BM901080D, pp. 224-232, XP002633320.
Buwalda, "Hydrogels Based on Amphiphilic PEG Star Block Copolymers," Dissertation submitted to Universiteit Twente, Dec. 8, 2011, pp. 1-159 (total 160 pages).
Calucci et al., "Self-Aggregation of Gel Forming PEG-PLA Star Block Coplymers in Water," Langmuir, vol. 26, No. 15, 2010 (Published on Web Jul. 12, 2010), pp. 12890-12896.
Cameron et al., "Aliphatic Polyester Polymer Stars: Synthesis, Properties and Applications in Biomedicine and Nonotechnology," Chemical Society Reviews, vol. 40, 2011 (Published on Nov. 16, 2010), pp. 1761-1776.
Choi et al., "Star-Shaped Poly(ether-ester) Block Copolymers: Synthesis, Charaterization, and Their Physical Properties," Macromolecules, vol. 31, No. 25, 1998, pp. 8766-8774.
Hiemstra et al., "In-Situ Formation of Biodegrabable Hydrogels by Stereocompelxation of PEG-(PLLA)$_s$: and PEG-(PDLA)$_a$: Star Block Copolymers," Biomacromolecules, vol. 7, No. 10, 2006 (Published on Web Sep. 13, 2006), pp. 2790-2795.
International Preliminary Report on Patentability for PCT/EP2020/050333 (PCT/IB/373) mailed on Jul. 22, 2021.
International Search Report, issued in PCT/EP2020/050333, dated Mar. 20, 2020.
Japanese Office Action for Japanese Application No. 2021-539653, dated Jan. 16, 2024, with an English translation.
Jeong et al., "New Biodegradable Polymers for Injectable Drug Delivery Systems," Journal of Controlled Release, vol. 62, 1999, pp. 109-114.
Jun et al., "In situ Gel Forming Stereocomplex Composed of Four-Arm PEG-PDLA and PEG-PLLA Block Copolymers", Macromolecular Research, 2008, vol. 16, No. 8, pp. 704-710.
Li et al., "Biodegradable Polymersomes from Four-Arm PEG-b-PDLLA for Encapsulating Hemoglobin," Journal of Applied Polymer Science, vol. 131, 2014, pp. 1-5.
Lin et al., "Preparation of Ibuprofen/sPEG-b-PLLA Copolymer Microspheres and Its in vitro Release Properties," Acta Pharmaceutica Sinica, vol. 45, No. 12, 2010, pp. 1570-1575, with an English abstract.
Michalski et al., "Star-shaped and branched polylactides: Synthesis, characterization, and properties," Progress in Polymer Science, vol. 89, 2019, pp. 159-212.
Neckel et al., "Preparação e caracterização de nanocápsulas contendo camptotecina a partir do ácido poli (D,L-lático) e de copolimeros diblocos do ácido poli (D,L-lático) e polietilenoglicol," Acta Farm. Bonaerense, vol. 24, No. 4, 2005, pp. 504-511.
United Kingdom Search Report, issued in Priority Application No. 1900258.3, dated Jun. 27, 2019.
Written Opinion of the International Searching Authority, issued in PCT/EP2020/050333, dated Mar. 20, 2020.
U.S. Appl. No. 17/421,602, filed Jul. 8, 2021.
Chinese Office Action and Search Report for Chinese Application No. 202080017968.9, dated Sep. 20, 2022, with English translation.

\* cited by examiner

F396: 40.00%P2R6_2.00%Meloxicam_58.00%DMSO

F397: 40.00%s4-P2R6_2.00%Meloxicam_58.00%DMSO

F396: 40.00%P2R6_2.00%Meloxicam_58.00%DMSO

F397: 40.00%s4-P2R6_2.00%Meloxicam_58.00%DMSO

F511: 38.00%dP2R6_2.00%Meloxicam_60.00%DMSO

F397: 40.00%s4-P2R6_2.00%Meloxicam_58.00%DMSO

F511: 38.00%dP2R6_2.00%Meloxicam_60.00%DMSO

F397: 40.00%s4-P2R6_2.00%Meloxicam_58.00%DMSO

F397: 40.00%s4-P2R6_2.00%Meloxicam_58.00%DMSO

F510: 61.00%dP2R1.5_2.00%Meloxicam_37.00%DMSO

F391: 40.00%P2R3.5_2.00%Meloxicam_58.00%DMSO

F451: 47.00%s4-P2R3_2.00%Meloxicam_51.00%DMSO

F391: 40.00%P2R3.5_2.00%Meloxicam_58.00%DMSO

F451: 47.00%s4-P2R3_2.00%Meloxicam_51.00%DMSO

F449: 45.00%dP2R3_2.00%Meloxicam_53.00%DMSO

F451: 47.00%s4-P2R3_2.00%Meloxicam_51.00%DMSO

F449: 45.00%dP2R3_2.00%Meloxicam_53.00%DMSO

F451: 47.00%s4-P2R3_2.00%Meloxicam_51.00%DMSO

F509: 68.00%dP2R0.8_2.00%Meloxicam_30.00%DMSO

F451: 47.00%s4-P2R3_2.00%Meloxicam_51.00%DMSO

F509: 68.00%dP2R0.8_2.00%Meloxicam_30.00%DMSO

F451: 47.00%s4-P2R3_2.00%Meloxicam_51.00%DMSO

F388: 40.00%P2R2_2.00%Meloxicam_58.00%DMSO

F389: 40.00%s4-P2R2_2.00%Meloxicam_58.00%DMSO

F388: 40.00%P2R2_2.00%Meloxicam_58.00%DMSO

F389: 40.00%s4-P2R2_2.00%Meloxicam_58.00%DMSO

F483: 44.00%P2R3.5_2.00%Meloxicam_54.00%NMP

F484: 47.00%dP2R3_2.00%Meloxicam_51.00%NMP

F489: 51.00%s4P2R3_2.00%Meloxicam_47.00%NMP

F483: 44.00%P2R3.5_2.00%Meloxicam_54.00%NMP

F484: 47.00%dP2R3_2.00%Meloxicam_51.00%NMP

F489: 51.00%s4P2R3_2.00%Meloxicam_47.00%NMP

F391: 40.00%P2R3.5_2.00%Meloxicam_58.00%DMSO

F449: 45.00%dP2R3_2.00%Meloxicam_53.00%DMSO

F451: 47.00%s4-P2R3_2.00%Meloxicam_51.00%DMSO

F397: 40.00%s4-P2R6_2.00%Meloxicam_58.00%DMSO

◇ F2: 20.00%s4-P2R3_20.00%P2R2_2.00%Meloxicam_58.00%DMSO

PHARMACEUTICAL COMPOSITION

CROSS-REFERENCE TO RELATED APPLICATIONS

This application is a Continuation of copending application Ser. No. 17/421,602, filed on Jul. 8, 2021, which is the National Phase under 35 U.S.C. § 371 of International Application No. PCT/EP2020/050333, filed on Jan. 8, 2020, which claims the benefit under 35 U.S.C. § 119(a) to Patent Application No. 1900258.3, filed in United Kingdom on Jan. 8, 2019, all of which are hereby expressly incorporated by reference into the present application.

FIELD OF THE INVENTION

The present invention relates to controlled release drug delivery or pharmaceutical compositions, in particular pharmaceutical compositions suitable for generating an in-situ depot. Specifically, the present invention relates to a pharmaceutical composition comprising a biodegradable multi-branched copolymer comprising at least three polyester arms attached to a central core which comprises a polyether, and wherein the multi-branched copolymer is substantially insoluble in aqueous solution, further comprising at least one pharmaceutically active ingredient.

BACKGROUND OF THE INVENTION

WO2012/090070A describes a solvent-exchange in situ forming depot (ISFD) technology comprising a mixture of linear (m)PEG-polyesters dissolved in a biocompatible organic solvent. Upon injection, the solvent diffuses and the polymers, insoluble in water, precipitate and form a depot that can entrap an active pharmaceutical ingredient (API). The drug substance is released during a prolonged time from this depot.

There is still a need to provide an improved technology for sustained release. The use of branched PEG-polyester block copolymers has been identified as a potential way of improving presently used technologies which suffer from drawbacks such as high viscosity, high injectability values, and slow degradation kinetics.

Star-shaped PEG-polyester copolymers are branched structures consisting of several (three or more) linear chains connected to a central core. Star-shaped copolymers can be classified into two categories: star-shaped homopolymers or star-shaped copolymers. Star-shaped homopolymers consist of a symmetrical structure comprising radiating arms with identical chemical composition and similar molecular weight. Star-shaped copolymers consist of a symmetrical structure comprising radiating arms with similar molecular weight but composed of at least two different monomers.

Star-shaped (also known as multi-arm or multi-branched) copolymers are described in Cameron et al, Chemical Society Reviews, 40, 1761, 2011, and in Burke et al, Biomacromolecules, 18, 728, 2017).

Hiemstra et al, Biomacromolecules, 7, 2790, 2006; Buwalda et al, Biomacromolecules, 11, 224, 2010; Calucci et al, Langmuir, 26, 12890, 2010; Mayadunne et al, US2016/0058698A1, 2016 describe thermogelling aqueous systems.

EP1404294B1 describes the utilization of branched (co)polymers for formulating in situ forming depots (ISFDs) by solvent exchange.

Accordingly, there is a need to provide new solvent-exchange ISFD formulations based on star-shaped copolymers with lower viscosity, improved injectability, improved or different release characteristics of the API or depot degradation kinetics.

SUMMARY OF THE INVENTION

The present invention provides a pharmaceutical composition comprising: a biodegradable multi-branched copolymer comprising at least three polyester arms attached to a central core which comprises a polyether, and wherein the multi-branched copolymer is substantially insoluble in aqueous solution, further comprising at least one pharmaceutically active ingredient.

Typically, the molecular weight of the polyether is 10 kDa or less, preferably 5 kDa or less, 4 kDa or less, 3 kDa or less, or 2 kDa or less, or 1 kDa or less, or 0.5 kDa or less.

The present invention also provides a pharmaceutical composition comprising:

a biodegradable polyester multi-branched copolymer comprising at least three polyester arms attached to a central core which comprises a polyether, and wherein the molecular weight of the polyether is 10 kDa or less, preferably 5 kDa or less, 4 kDa or less, 3 kDa or less, or 2 kDa or less, or 1 kDa or less, or 0.5 kDa or less, further comprising at least one pharmaceutically active ingredient.

The above-mentioned compositions are suitable for forming an in-situ depot.

It has been surprisingly found that formulations based on multi-branched or star-shaped copolymers have a lower viscosity and improved injectability, whilst at the same time providing improved or different release profiles of the active ingredient, over formulations comprising linear copolymer analogues alone. In addition, depots resulting from multi-branched or star-shaped based formulations degrade quicker than those made of analogue linear copolymers.

Typically, the multi-branched copolymer is substantially insoluble in aqueous solution.

In a preferred embodiment, the multi-branched copolymer has less than 15 mg/mL, optionally less than 10 mg/mL, less than 5 mg/mL, less than 2 mg/mL, or less than 1 mg/mL solubility in aqueous solution. Typically, the solubility is measured at 37° C.

Typically, the multi-branched copolymer is of formula $A(B)_n$ wherein A represents the central core and B represents the polyester arms and n is an integer of at least 3. In embodiments of the invention n is at least 4, or at least 6, or at least 8. n may be 3, 4, 6 or 8. Preferably, n is 4.

In one embodiment the central core is a multi-branched polyether which is derivable from poly(ethylene glycol) (PEG) and a polyol. Typically the polyol comprises at least three hydroxyl groups. The polyol is typically a hydrocarbon functionalized with at least three hydroxyl groups, optionally 3, 4, 5, 6 or 8 hydroxyl groups. In some embodiments the polyol further comprises one or more ether groups. Preferably the polyol is pentaerythritol (PE), dipentaerythritol (DPE), trimethylolpropane (TMP), glycerol, hexaglycerol, erythritol, xylitol, di(trimethylolpropane) (diTMP), sorbitol, or inositol.

In preferred embodiments the multi-branched polyether has Formula 1 or Formula 2 or Formula 3 or Formula 4:

Formula 1

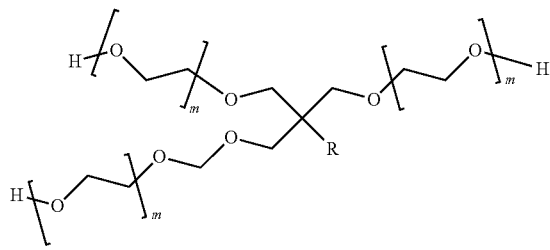

wherein m is an integer between 2 and 150.
R is H or an alkyl or PEG. Preferably R is PEG.

Formula 2

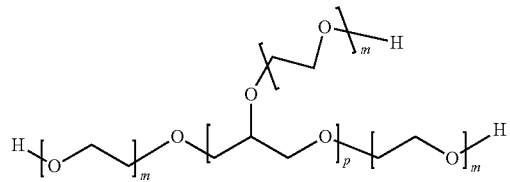

wherein m is an integer between 2 and 150 and p is 6.

Formula 3

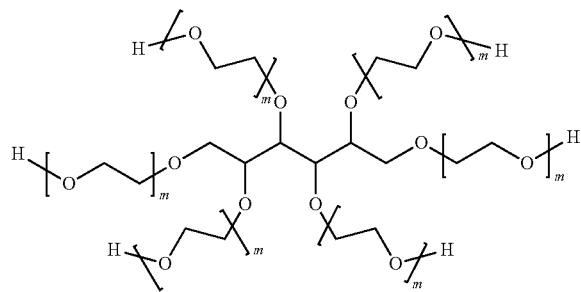

wherein m is an integer between 2 and 150.

Formula 4

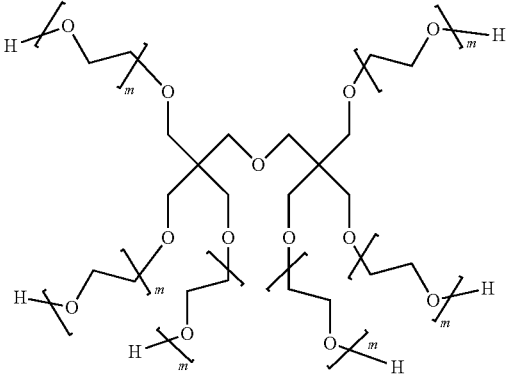

wherein m is an integer between 2 and 150.

Typically, the polyester is or is formed from at least one polymer or copolymer selected from the group of poly(lactic acid) (PLA), poly(glycolic acid) (PGA), poly(epsilon-caprolactone) (PCL), poly(ethylene adipate) (PEA), poly(lactic acid-co-glycolic acid) (PLGA) and poly(hydroxyalkanoate) (PHA) or mixtures thereof. The polyester arms are typically formed by reacting a precursor or monomer of the polyester with the polyether core. For example, when forming PLA arms, the polyether is reacted with D,L-lactide.

In preferred embodiments each branch of the multi-branched polyether has a terminal reactive group capable of reacting with a polyester or monomer or precursor thereof. Typically, the terminal reactive group is a hydroxyl group or an amine group, but preferably a hydroxyl group.

In one embodiment the polyester is a homopolymer.

In one embodiment the polyester is derived from more than one monomer. When the polyester is derived from more than one monomer, the polyester may be a random copolymer or a block copolymer.

In a preferred embodiment the polyester is or comprises PLA.

In a preferred embodiment the multi-branched copolymer is obtainable by reacting a multi-branched polyether as defined above with D,L-lactide. The multi-branched copolymer may be obtainable by ring-opening polymerisation of the D,L-lactide initiated by the multi-branched polyether.

In a preferred embodiment the multi-branched copolymer has Formula 5 or Formula 6 or Formula 7 or Formula 8:

Formula 5

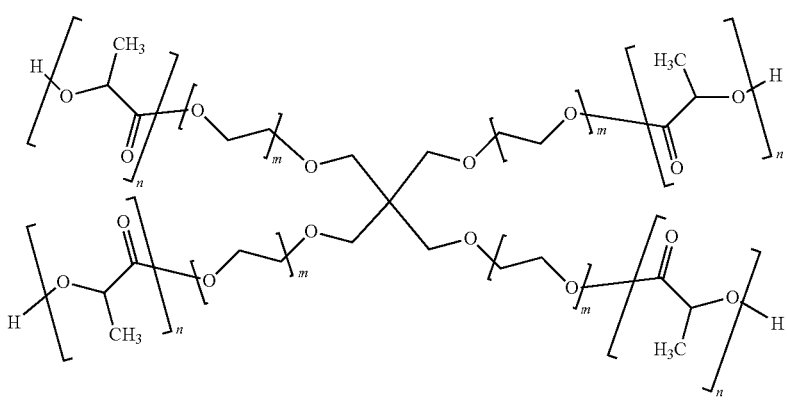

wherein u is an integer between 4 to 200 and m is an integer between 2 and 150
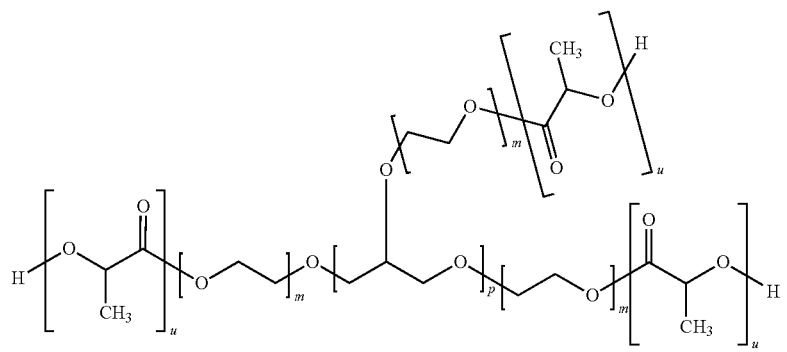
Formula 6
wherein u is an integer between 4 to 200, m is an integer between 2 and 150 and p is 6.
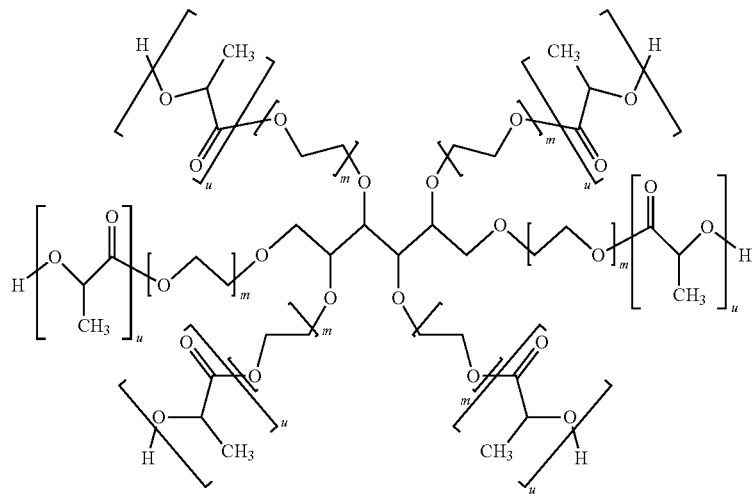
Formula 7
wherein u is an integer between 4 to 200 and m is an integer between 2 and 150.

Formula 8

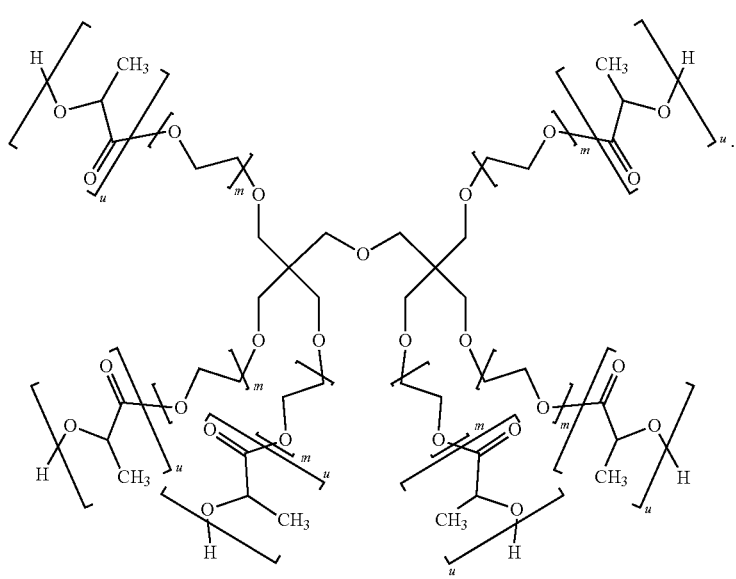

wherein u is an integer between 4 to 200 and m is an integer between 2 and 150

In preferred embodiments of the above-mentioned multi-branched copolymer of Formula 5 the polyether core (i.e. the compound of Formula 5 minus the PLA arms) has a molecular weight of 2 kDa and the ester repeat unit to ethylene oxide molar ratio is 2, 3 or 6.

In one embodiment the number of ester repeat units in each arm is independently in the range of from 4 to 200.

In a preferred embodiment, the molecular weight of the polyether ranges from 0.5 kDa to 10 kDa, optionally 1 kDa to 10 kDa preferably 2 kDa to 10 kDa, most preferably 2 kDa to 5 kDa. In a further embodiment, the molecular weight of the polyester ranges from 0.5 kDa to 2 kDa.

In preferred embodiments the ester repeat unit to ethylene oxide molar ratio of the multi-branched copolymer in the composition is from 1 to 10, preferably from 2 to 6.

In an additional embodiment, the composition of the invention may comprise one or more further biodegradable multi-branched copolymers as defined above. Providing a composition comprising two or more multi-branched copolymers provides a further means of modulating the release of a pharmaceutically active agent. Different combinations of the multi-branched copolymers can be provided, and the relative amounts of the two or more multi-branched copolymers can be altered. This allows the release profile of the pharmaceutically active agent to be controlled.

In one embodiment the composition comprises a first biodegradable multi-branched copolymer as defined above and a second different biodegradable multi-branched copolymer as defined above, optionally wherein the first biodegradable multi-branched copolymer is present in an amount of from 15 to 25 (w/w %), optionally 18 to 20 (w/w %) and the second biodegradable multi-branched copolymer is present in an amount of from 15 to 25 (w/w %), optionally 18 to 20 (w/w %) of the total composition.

In one embodiment the first and second biodegradable multi-branched copolymers each have a structure according to Formula 5:

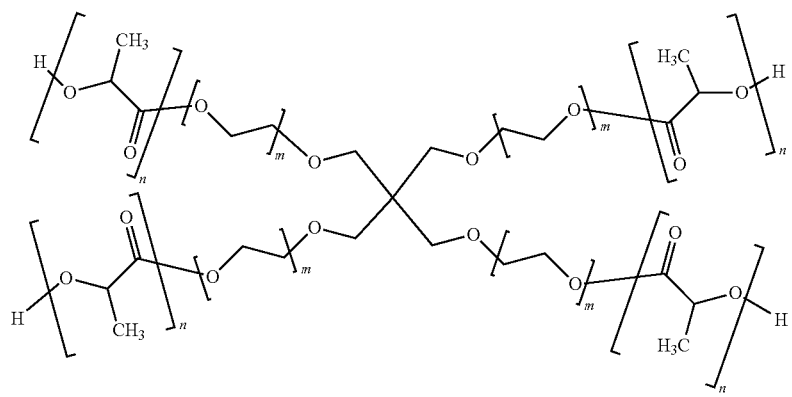

wherein u is an integer between 4 to 200 and m is an integer between 2 and 150; and wherein the first biodegradable multi-branched copolymer has a polyether core having a molecular weight of 2 kDa and the ester repeat unit to ethylene oxide molar ratio is 2; and wherein the second biodegradable multi-branched copolymer has a polyether core having a molecular weight of 2 kDa and the ester repeat unit to ethylene oxide molar ratio is 6; or the first biodegradable multi-branched copolymer has a polyether core having a molecular weight of 5 kDa and the ester repeat unit to ethylene oxide molar ratio is 2;

and wherein the second biodegradable multi-branched copolymer has a polyether core having a molecular weight of 2 kDa and the ester repeat unit to ethylene oxide molar ratio is 6.

In an alternative embodiment of the invention the composition further comprises a biodegradable triblock copolymer having the formula:

$$A_v\text{-}B_w\text{-}A_x$$

wherein A is a polyester and B is polyethylene glycol and v and x are the number of repeat units ranging from 1 to 3,000 and w is the number of repeat units ranging from 3 to 300 and v=x or v≠x.

The combination of a multi-branched copolymer with a linear triblock copolymer leads to a further option for modulating the release of a pharmaceutically active ingredient.

Typically the mass of the polyethylene glycol chain in the triblock copolymer ranges from 180 Da to 12 kDa or 194 Da to 12 kDa or 200 Da to 12 kDa or from 100 Da to 4 kDa, preferably 1 kDa to 2 kDa.

Typically the molar ratio of the ester repeat unit to the ethylene oxide repeat unit in the triblock copolymer is from 0.5 to 22.3, optionally 0.5 to 10, preferably 0.5 to 3.5.

In a preferred embodiment the triblock copolymer has a polyethylene glycol chain having a mass of 1 kDa and has a molar ratio of the ester repeat unit to the ethylene oxide repeat unit of 4, and the multi-branched copolymers has a structure according to Formula 5:

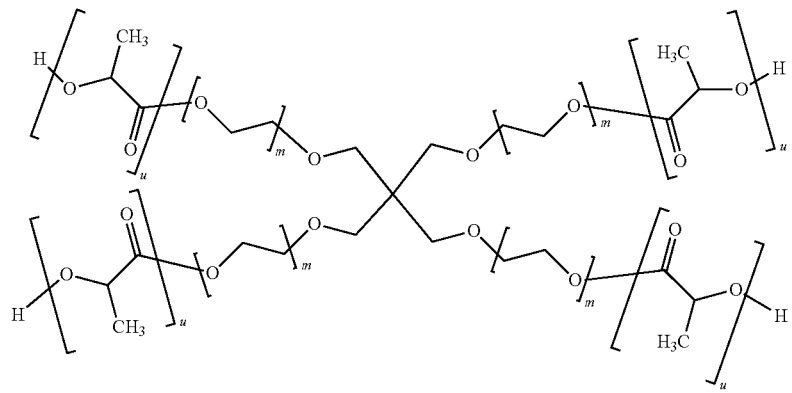

wherein u is an integer between 4 to 200 and m is an integer between 2 and 150; having a polyether core having a molecular weight of 2 kDa and the ester repeat unit to ethylene oxide molar ratio is 3; or wherein the triblock copolymer has a polyethylene glycol chain having a mass of 2 kDa and has a molar ratio of the ester repeat unit to the ethylene oxide repeat unit of 2, and the multi-branched copolymers has a structure according to Formula 5 having a polyether core having a molecular weight of 2 kDa and the ester repeat unit to ethylene oxide molar ratio is 2;

wherein the triblock copolymer has a polyethylene glycol chain having a mass of 2 kDa and has a molar ratio of the ester repeat unit to the ethylene oxide repeat unit of 2, and the multi-branched copolymers has a structure according to Formula 5 having a polyether core having a molecular weight of 2 kDa and the ester repeat unit to ethylene oxide molar ratio is 6;

optionally wherein the multi-branched copolymer is present in an amount of from 15 to 25 (w/w %), optionally 18 to 20 (w/w %) of the total composition and the triblock copolymer is present in an amount of from 15 to 25 (w/w %), optionally 18 to 20 (w/w %) of the total composition.

In a further alternative embodiment the composition further comprises a biodegradable diblock copolymer having the formula:

$$C_y\text{-}A_z$$

wherein A is a polyester and C is an end-capped polyethylene glycol and y and z are the number of repeat units with y ranging from 2 to 250 and z ranging from 1 to 3,000.

The combination of a multi-branched copolymer with a linear diblock copolymer provides an additional option for modulating the release of a pharmaceutically active ingredient.

In one embodiment the molecular weight of the end-capped polyethylene glycol chain of the diblock copolymer ranges from 100 Da to 10 kDa or 164 Da to 2 kDa, preferably 1 kDa to 2 kDa.

In one embodiment the molar ratio of the ester repeat unit to the ethylene oxide repeat unit in the diblock copolymer is from 0.8 to 15, optionally 1 to 10.

Typically, the polyester A in the triblock or diblock copolymer is selected from the group of, (PLA), polyglycolic acid, polycaprolactone, polyethylene adipate, polylactic acid polyhydroxyalkanoate, poly(ε-caprolactone-co-lactide) (PCLA), poly(lactic-co-glycolic acid) (PLGA) and mixtures thereof and optionally wherein the end-capped polyethylene glycol is methoxy polyethylene glycol. Preferably the polyester A is polylactic acid.

In an embodiment of the invention, the composition further comprises a pharmaceutically acceptable vehicle, optionally wherein the pharmaceutically acceptable vehicle is an organic solvent, optionally wherein the organic solvent is a biocompatible organic solvent, optionally wherein the amount of said vehicle is at least 25%, or at least 35% (w/w %) of the total composition. Preferably, the pharmaceutically acceptable vehicle is selected from the group of:

benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin, glycofurol and mixtures thereof.

In one embodiment the pharmaceutically active ingredient is hydrophobic. By this is meant a pharmaceutical active ingredient having positive log P or log D values and aqueous solubility at physiological pH (pH 7.0 to 7.4) below 1 mg/mL.

In a preferred embodiment the pharmaceutically active ingredient is meloxicam, bupivacaine, tamsulosin, octreotide, tadalafil, empaglifozin, tenofovir, liothyronine, or combinations thereof.

In one embodiment the at least one pharmaceutically active ingredient is present in an amount of from 0.05% to 60% (w/w %), optionally 0.05% to 40%, optionally 0.05% to 30%, optionally 0.05% to 10%, optionally 0.05% to 7%, optionally 0.05% to 2% of the total composition.

In a preferred embodiment the composition is an injectable liquid.

In one embodiment the multi-branched copolymer is present in an amount of 2% to 80%, optionally 2% to 70%, optionally 2% to 60%, optionally 10% to 60%, optionally 10% to 50%, optionally 20% to 40%, optionally 20% to 35%, optionally 30% to 50% (w/w %) of the total composition.

In one embodiment the composition is as defined in Table 1 or Table 4.

Typically, the release of at least one pharmaceutically active ingredient can be modulated by the composition.

In one embodiment the composition is suitable to deliver a pharmaceutically active ingredient to a subject for at least 1 day, optionally at least 3 days, optionally at least 7 days, optionally at least 30 days, optionally at least 90 days, optionally at least 1 year.

In a further aspect, the present invention provides use of the pharmaceutical composition as defined above to modulate the kinetics of release of at least one active ingredient.

In an additional aspect, the present invention provides a method of producing a pharmaceutical composition as defined above, said method comprising dissolving a multi-branched copolymer as defined above in a pharmaceutically acceptable vehicle, such as a solvent. In one embodiment the method further comprises adding a pharmaceutically active ingredient to the composition.

In a further aspect, the invention provides a bioresorbable depot which is produced ex vivo or in situ by contacting the composition as defined above with an aqueous medium, water or body fluid. The depot is bioresorbable in the sense that the PLA moiety degrades in vivo, and that the PEG is assimilated by the body and excreted.

In a final aspect, provided is a method for the controlled release of a pharmaceutically active ingredient comprising administering the composition as defined above and allowing a solvent-exchange in situ depot to be formed in vivo.

DETAILED DESCRIPTION

As used herein the term "biodegradeable" or "bioresorbable" means that the block copolymers undergo hydrolysis in vivo to form their constituent (m)PEG and oligomers or monomers or repeat units derived from the polyester block. For example, PLA undergoes hydrolysis to form lactic acid. The result of the hydrolysis process leads to a progressive mass loss of the depot and ultimately to its disappearance.

The term "multi-branched copolymer" means a polymer with at least three polyester arms attached to a central core which comprises a polyether. The polyester arms may be referred to as "branches", "arms" or "chains". The term "multi-branched copolymer" has the same meaning as the term "star polymer" or "star-shaped polymer" or "multi-arm copolymer" and these terms are used interchangeably throughout.

Typically, the molecular weight of the polyether is 10 kDa or less, preferably 5 kDa or less, 4 kDa or less, 3 kDa or less, or 2 kDa or less, or 1 kDa or less or 0.5 kDa or less. Preferably, the polyether has a molecular weight of at least 0.2 kDa, or at least 0.5 kDa.

Typically, the multi-branched copolymer is of formula $A(B)_n$ wherein A represents the central core and B represents the polyester arms and n is an integer of at least 3. In embodiments of the invention n is at least 4, or at least 6, or at least 8. Preferably, n is 4. An example of the structure of a multi-branched PEG-PLA block copolymer with n=4 is provided below.

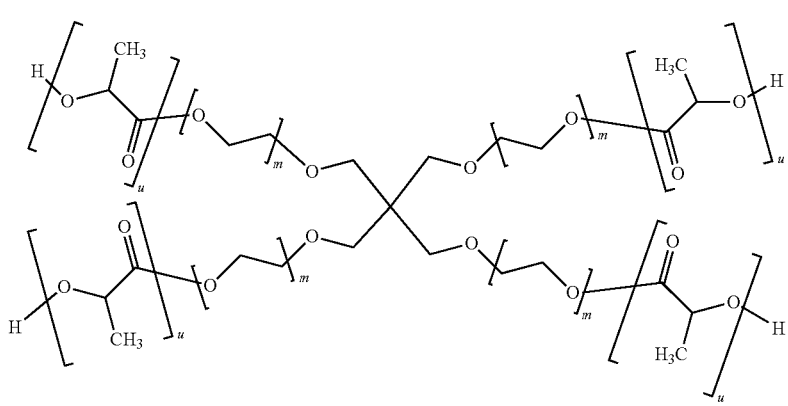

Formula 5

The letters m and u correspond to the number of ethylene oxide and lactic acid repeat units constituting each block respectively.

A polyol is an organic compound comprising a plurality of hydroxyl groups. Typically, the polyol has at least three hydroxyl groups. Typically, the polyol is a hydrocarbon functionalized with at least three hydroxyl groups, for example 3, 4, 5, 6, or 8 hydroxyl groups. The polyol may also comprise one or more ether groups. Typically, the polyol is pentaerythritol (PE), dipentaerythritol (DPE), trimethylolpropane (TMP), glycerol, hexaglycerol, erythritol, xylitol, di(trimethylolpropane) (diTMP), sorbitol, or inositol.

A polyether is an organic compound comprising a plurality of ether groups.

In a preferred embodiment the central core is a multi-branched polyether which is derivable from poly(ethylene glycol) (PEG) and a polyol. For example, the multi-branched polyether may be formed by reaction of ethylene oxide with a polyol. The multi-branched polyether may be referred to as a star-shaped PEG. The ethylene oxide reacts with a hydroxyl group of a polyol to form a PEG arm. For example, pentaerythritol may be reacted with ethylene oxide to form the four or three arm or four or three branched polyether set out below in Formula 1.

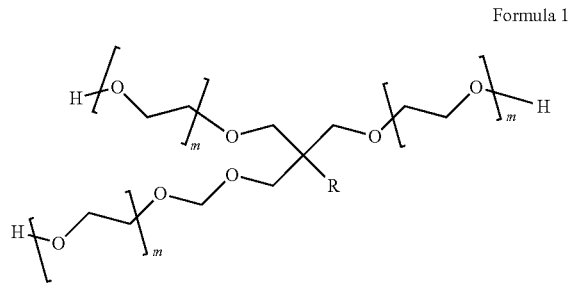

Formula 1 wherein m is an integer between 2 and 150.

R is H or alkyl or PEG.

In an alternative embodiment the multi-branched polyether is an eight-arm or eight branched polyether (p=6) as set out below in Formula 2.

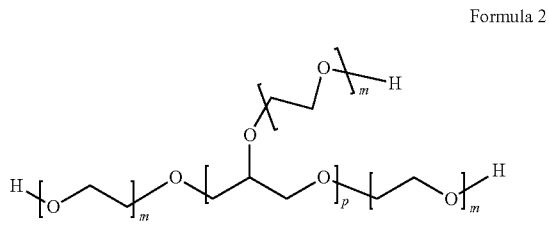

Formula 2 wherein m is an integer between 2 and 150 and p is 6.

In an alternative embodiment the multi-branched polyether is a six-arms, or six branched polyether as set out below in Formula 3 and formula 4.

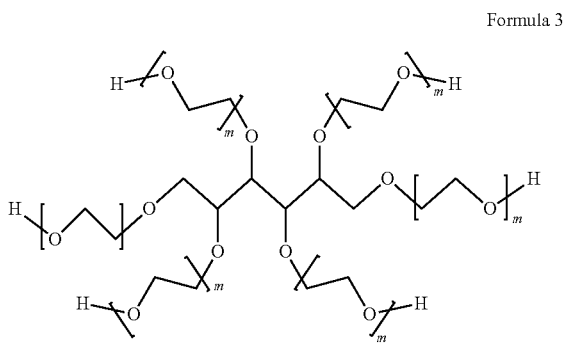

Formula 3 wherein m is an integer between 2 and 150.

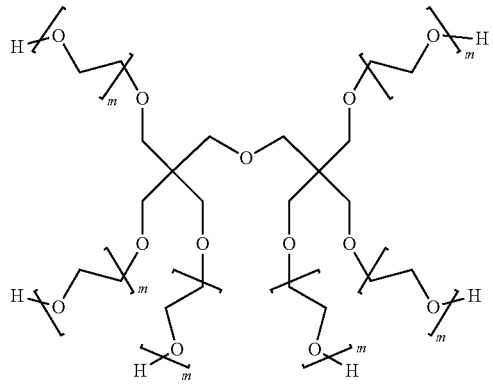

Formula 4 wherein m is an integer between 2 and 150.

Typically, each branch of the multi-branched polyether has a terminal hydroxyl group, however other terminal reactive groups capable of reacting with a polyester or monomers or precursors thereof may also be contemplated. Typically, the polyester is formed from at least one polymer or copolymer selected from the group of poly(lactic acid) (PLA), poly(glycolic acid) (PGA), poly(epsilon-caprolactone) (PCL), poly(ethylene adipate) (PEA), poly(lactic acid-co-glycolic acid) (PLGA) and poly(hydroxyalkanoate) (PHA) or mixtures thereof. Typically, the terminal hydroxyl group of each branch of the multi-branched polyether reacts with a monomer or precursor of the polyester to form a polyester arm. For example, D-L-lactide may react with the multi-branched polyether to form a PLA arm.

In one embodiment the polyester is a homopolymer.

In one embodiment the polyester is derived from more than one monomer. When the polyester is derived from more than one monomer, the polyester may be a random copolymer or a block copolymer.

In a preferred embodiment the polyester is or comprises PLA.

In one embodiment the number of ester repeat units in each arm is independently in the range of 4 to 200.

The term "depot injection" means an injection of a flowing pharmaceutical composition, usually subcutaneous, intradermal or intramuscular that deposits a drug in a localized mass, such as a solid mass, called a "depot". The depots as defined herein are in situ forming upon injection. Thus, the formulations can be prepared as solutions or suspensions and can be injected into the body.

An "in situ depot" is a solid, localized mass formed by precipitation of the pharmaceutical composition after injection of the composition into the subject. The pharmaceutical composition comprises a multi-branched copolymer which is substantially insoluble in aqueous solution. Thus, when the pharmaceutical composition contacts the aqueous environment of the human or animal body, a phase inversion occurs causing the composition to change from a liquid to a solid, i.e. precipitation of the composition occurs, leading to formation of an "in situ depot".

An "in situ depot" can be clearly distinguished from hydrogel pharmaceutical formulations described in the prior art.

Hydrogels can be formed from star polymers comprising a polyether core and PLA branches. Certain star polymers comprising a polyether core and PLA branches can form micelles in aqueous solution. The hydrophobic PLA outer blocks associate with neighbouring micelles to form a network of linked micelles or large aggregates, giving rise to gels under specific temperature and concentration ranges. Hydrogels have three-dimensional networks that are able to absorb large quantities of water. The polymers making up hydrogels are soluble in aqueous solution. By contrast, the multi-branched polymers used in the present invention are substantially insoluble in aqueous solution. The pharmaceutical compositions of the invention are free of water, or substantially free of water. For example, the pharmaceutical compositions of the invention comprise less than 0.5% w/w water.

Typically, the multi-branched copolymer is substantially insoluble in aqueous solution. Typically, this means that the multi-branched copolymer has less than 15 mg/mL, optionally less than 10 mg/mL, less than 5 mg/mL, less than 2 lymers provides a further means of modulating the release of a pharmaceutically active agent. Different combinations of the multi-branched copolymers can be provided, and the relative amounts of the two or more multi-branched copolymers can be altered.

In one embodiment the composition comprises a first biodegradable multi-branched copolymer as defined above and a second different biodegradable multi-branched copolymer as defined above. The first biodegradable multi-branched copolymer may be present in an amount of from 15 to 25 (w/w %) and the second biodegradable multi-branched copolymer may be present in an amount of from 15 to 25 (w/w %) of the total composition.

In one embodiment the first and second biodegradable multi-branched copolymers each have a structure according to Formula 5:

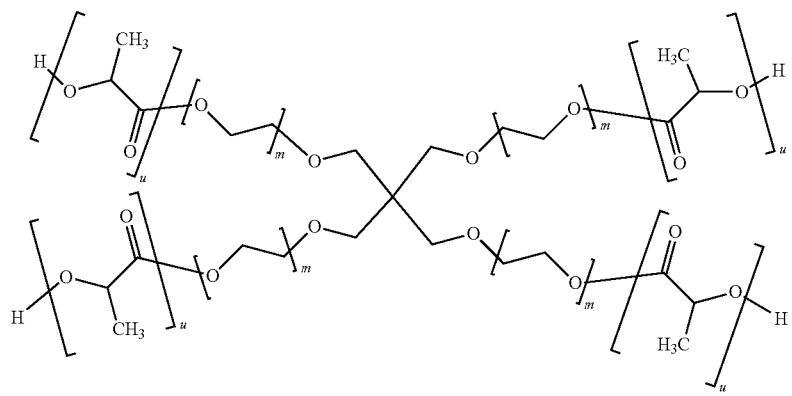

mg/mL, optionally less than 1 mg/mL solubility in aqueous solution. Typically, the solubility is measured at 37° C.

In a preferred embodiment, the solubility of the multi-branched copolymer in water was determined as follows:

500 mg of copolymer were put in an empty 20 mL vial. 5 mL of ultra-pure water were added, the vial was put at 37° C. under continuous vortexing for 2 hours. Then, the vial was centrifuged 10 min at 3000 rpm. The supernatant was transferred to another vial of known weight which was placed at −80° C. overnight, prior to lyophilization during 24 h. The amount of solubilized copolymer was determined as the difference of weight of the empty vial and the lyophilized one.

Temperature sensitive hydrogels, or thermogels as described in the prior art are typically solid at a specific narrow temperature range, for example 30 to 35° C., and this solidification is reversible. By contrast, the in-situ depot formed in the present invention is solid when injected over a much broader temperature range, for example 20° C. to 37° C.

In addition, hydrogels based on PEG and PLA have been shown to function as sustained release formulations for up to about 6 months. By contrast, the depot formed by the composition of the present invention, allows release of the API over a longer period.

In an additional embodiment, the composition of the invention may comprise one or more further biodegradable multi-branched copolymers as defined above. Providing a composition comprising two or more multi-branched copowherein u is an integer between 4 to 200 and m is an integer between 2 and 150;

and wherein the first biodegradable multi-branched copolymer has a polyether core having a molecular weight of 2 kDa and the ester repeat unit to ethylene oxide molar ratio is 2;

and wherein the second biodegradable multi-branched copolymer has a polyether core having a molecular weight of 2 kDa and the ester repeat unit to ethylene oxide molar ratio is 6; or the first biodegradable multi-branched copolymer has a polyether core having a molecular weight of 5 kDa and the ester repeat unit to ethylene oxide molar ratio is 2;

and wherein the second biodegradable multi-branched copolymer has a polyether core having a molecular weight of 2 kDa and the ester repeat unit to ethylene oxide molar ratio is 6.

In an alternative embodiment of the invention the composition further comprises a biodegradable triblock copolymer having the formula:

$$A_v\text{-}B_w\text{-}A_x$$

wherein A is a polyester and B is polyethylene glycol and v and x are the number of repeat units ranging from 1 to 3,000 and w is the number of repeat units ranging from 3 to 300 and v=x or v≠x.

The combination of a multi-branched copolymer with a linear triblock copolymer leads to a further option for modulating the release of a pharmaceutically active ingredient.

Typically the mass of the polyethylene glycol chain in the triblock copolymer ranges from 180 Da to 12 kDa or 194 Da to 12 kDa or 200 Da to 12 kDa or from 100 Da to 4 kDa, preferably 1 kDa to 2 kDa.

Typically the molar ratio of the ester repeat unit to the ethylene oxide repeat unit in the triblock copolymer is from 0.5 to 22.3, optionally 0.5 to 10, preferably 0.5 to 3.5.

In a preferred embodiment the triblock copolymer has a polyethylene glycol chain having a mass of 1 kDa and has a molar ratio of the ester repeat unit to the ethylene oxide repeat unit of 4, and the multi-branched copolymers has a structure according to Formula 5:

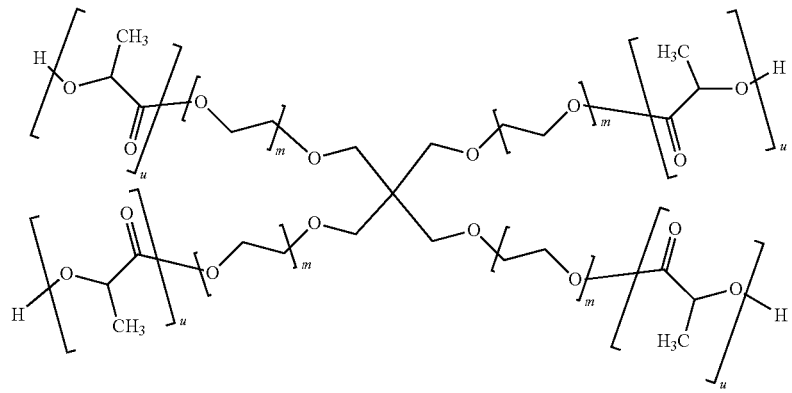

wherein u is an integer between 4 to 200 and m is an integer between 2 and 150; having a polyether core having a molecular weight of 2 kDa and the ester repeat unit to ethylene oxide molar ratio is 3; or
  wherein the triblock copolymer has a polyethylene glycol chain having a mass of 2 kDa and has a molar ratio of the ester repeat unit to the ethylene oxide repeat unit of 2, and the multi-branched copolymers has a structure according to Formula 5 having a polyether core having a molecular weight of 2 kDa and the ester repeat unit to ethylene oxide molar ratio is 2; or
  wherein the triblock copolymer has a polyethylene glycol chain having a mass of 2 kDa and has a molar ratio of the ester repeat unit to the ethylene oxide repeat unit of 2, and the multi-branched copolymers has a structure according to Formula 5 having a polyether core having a molecular weight of 2 kDa and the ester repeat unit to ethylene oxide molar ratio is 6;
  optionally wherein the multi-branched copolymer is present in an amount of from 15 to 25 (w/w %) of the total composition and the triblock copolymer is present in an amount of from 15 to 25 (w/w %) of the total composition.

In a further alternative embodiment the composition further comprises a biodegradable diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000.

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolactide, caprolactone and the like or other esters and mixtures thereof. The reaction of an end-capped PEG polymer with lactide generates a diblock cPEG-PLA copolymer.

The combination of a multi-branched copolymer with a linear diblock copolymer provides an additional option for modulating the release of a pharmaceutically active ingredient.

In one embodiment the molecular weight of the end-capped polyethylene glycol chain of the diblock copolymer ranges from 100 Da to 10 kDa or 164 Da to 2 kDa, preferably 1 kDa to 2 kDa.

In one embodiment the molar ratio of the ester repeat unit to the ethylene oxide repeat unit in the diblock copolymer is from 0.8 to 15, optionally 1 to 10.

Typically, the polyester A in the triblock or diblock copolymer is selected from the group of, polylactic acid (PLA), polyglycolic acid, polycaprolactone, polyethylene adipate, polyhydroxyalkanoate, poly(ε-caprolactone-co-lactide) (PCLA), poly(lactic-co-glycolic acid) (PLGA) and mixtures thereof and optionally wherein the end-capped polyethylene glycol is methoxy polyethylene glycol. Preferably the polyester A is polylactic acid.

Triblock and diblock linear copolymers suitable for use in the compositions of the invention are described in WO2012/090070A1, WO2019016233A1, WO2019016234A1, and WO2019016236A1 incorporated by reference herein.

In an embodiment of the invention, the composition further comprises a pharmaceutically acceptable vehicle, optionally wherein the pharmaceutically acceptable vehicle is an organic solvent. The solvent is typically a biocompatible solvent. Preferably, the pharmaceutically acceptable vehicle is selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin, glycofurol, and mixtures thereof. The amount of said vehicle is typically at least 25%, or at least 35% (w/w %) of the total composition.

The composition comprises at least one pharmaceutically active ingredient.

In one embodiment the pharmaceutically active ingredient is hydrophobic.

In a preferred embodiment the pharmaceutically active ingredient is meloxicam, bupivacaine, tamsulosin, octreotide, tadalafil, empaglifozin, tenofovir, liothyronine, or combinations thereof.

In one embodiment the at least one pharmaceutically active ingredient is present in an amount of from 0.05% to 60% (w/w %), optionally 0.05% to 40%, optionally 0.05% to 30%, optionally 0.05% to 10%, optionally 0.05% to 7%, optionally 0.05% to 2% of the total composition.

In a preferred embodiment the composition is an injectable liquid.

In one embodiment the multi-branched copolymer is present in an amount of 2% to 80%, optionally 2% to 70%, optionally 2% to 60%, optionally 10% to 60%, optionally 10% to 50%, optionally 20% to 40%, optionally 20% to 35%, optionally 30% to 50% (w/w %) of the total composition. This may be the amount of a single multi-branched copolymer if only one multi-branched copolymer is present or the total amount of multi-branched copolymer if two or more multi-branched copolymers are present. If a diblock or triblock copolymer is present the amount of the multi-branched copolymer is preferably altered so that the total amount of copolymer remains substantially constant.

Typically, the ester repeat unit to ethylene oxide molar ratio in the composition is from 1 to 10, preferably from 2 to 6.

Typically, the release of at least one pharmaceutically active ingredient can be modulated by the composition.

In one embodiment the composition is suitable to deliver a pharmaceutically active ingredient to a subject for at least 1 day, optionally at least 3 days, optionally at least 7 days, optionally at least 30 days, optionally at least 90 days, optionally at least 1 year.

In a further aspect, the present invention provides use of the pharmaceutical composition as defined above to modulate the kinetics of release of at least one pharmaceutically active ingredient.

In an additional aspect, the present invention provides a method of producing a pharmaceutical composition as defined above, said method comprising dissolving a multi-branched copolymer as defined above in a pharmaceutically acceptable vehicle, and subsequently adding a pharmaceutically active ingredient to the composition.

In a further aspect, the invention provides a bioresorbable depot which is produced ex vivo or in situ by contacting the composition as defined above with an aqueous medium, water or body fluid.

In a final aspect, provided is a method for the controlled release of a pharmaceutically active ingredient comprising administering the composition as defined above to a subject and allowing an in situ depot to be formed in vivo.

The pharmaceutical composition is preferably suitable for parenteral administration. The term "parenteral administration" encompasses intramuscular, intraperitoneal, intra-abdominal, subcutaneous, intravenous and intraarterial. It also encompasses intradermal, intracavernous, intravitreal, intracerebral, intrathecal, epidural, intra-articular, and intraosseous administration.

The subject may be an animal or a plant. The term "animals" encompasses all members of the Kingdom Animalia. The animal may be a human or non-human animal.

As used herein the term "plant" encompasses all members of the Plant Kingdom.

"Pharmaceutically active ingredient" means a drug or medicine for treating or preventing various medical illnesses. For the purposes of the present application the term "active principle" has the same meaning as "active ingredient". Thus, the terms active ingredient, active principle, drug or medicine are used interchangeably. The term Active Pharmaceutical Ingredient, or "API" is also used. The term drug or active ingredient as used herein includes without limitation physiologically or pharmacologically active substances that act locally or systemically in the body of an animal or plant.

As used herein "disease" means any disorder in a human, animal or plant caused by infection, diet, or by faulty functioning of a process.

The term "spatial formulation" encompasses any formulation that can be applied on or into the animal or plant body and do not necessarily have to be administered through a syringe.

As used herein "repeat units" are the fundamental recurring units of a polymer.

As used herein "polyethylene glycol", as abbreviated PEG throughout the application, is sometimes referred to as poly(ethylene oxide) or poly(oxyethylene) and the terms are used interchangeably in the present invention.

The abbreviation of "PLA" refers to poly(lactic acid).

The abbreviation of "PLGA" refers to poly(lactic-co-glycolic acid).

The abbreviation of "PCLA" refers to poly(ε-caprolactone-co-lactide).

The abbreviation "PE" refers to polyester.

The copolymers have been named as follows:

The linear triblock polymers described herein were labelled PxRy where x represents the molecular weight of the PEG chain in kDa and y is the ester repeat unit/ethylene oxide molar ratio, for example the lactic acid/ethylene oxide (LA/EO) molar ratio and allows the calculation of the PLA chain length within the copolymer.

The linear diblock polymers described herein were labelled dPxRy where x represents the molecular weight of the PEG chain in kDa and y is the ester monomer/ethylene oxide molar ratio, for example the lactic acid/ethylene oxide (LA/EO) molar ratio.

sz-PxRy stands for a star-shaped PEG-PLA copolymer with z arms. x and y provide the same information as in linear copolymers, namely x represents the molecular weight of the polyether core formed from the reaction of a polyol and PEG (often referred to as the "star-shaped PEG") and y is the ester monomer/ethylene oxide molar ratio.

As an example, s4-P2R6 is a 4-arm star-shaped copolymer with a 2 kDa star PEG block with an overall LA/EO molar ratio of 6.

The "injectability" of a formulation, as used herein, is defined by the force needed in Newtons (N) to inject a formulation using pre-determined parameters. These parameters include: injection speed, injection volume, injection duration, syringe type or needle type and the like. These parameters may vary based on at least one pharmaceutically active ingredient used, or the desired method of administration such as subcutaneous, intra-ocular, intra-articular and the like. They may be adjusted based on the at least one pharmaceutically active ingredient present within the formulations, to be able to observe the differences and fluctuations between the formulations. The injectability must be kept low such that the formulation can be easily administered by a qualified healthcare professional in an acceptable timeframe. An acceptable injectability value may be from 0.1 N to 20 N with the measurement method described below, with an injectability of from 0.1 N to 10 N being most preferred. A non-optimal injectability may be greater than 20 N to 30 N. Formulations are hardly injectable from 30 to 40 N and non-injectable above 40 N. Injectability may be measured using a texturometer, preferably a Lloyd Instruments FT plus texturometer, using the following analytical conditions: 500 μL of formulation are injected through a 1 ml syringe, a 23G 1" Terumo needle with a 1 mL/min flow rate as described in example 6.

"Viscosity," by definition and as used herein, is a measure of a fluid's resistance to flow and gradual deformation by shear stress or tensile strength. It describes the internal friction of a moving fluid. For liquids, it corresponds to the informal concept of "thickness". By 'dynamic viscosity" is meant a measure of the resistance to flow of a fluid under an applied force. The dynamic velocity can range from 1 mPa·s. to 3000 mPa·s or 5 mPa·s to 2500 mPa·s or 10 mPa·s to 2000 mPa·s or 20 mPa·s to 1000 mPa·s. Dynamic viscosity is determined using an Anton Paar Rheometer equipped with cone plate measuring system. Typically, 250 µL of studied formulation are placed on the measuring plate. The temperature is controlled at ±25° C. The measuring system used is a cone plate with a diameter of 25 mm and a cone angle of 1 degree (CP25-1).

The working range is from 10 to 1000 $s^{-1}$. After being vortexed for 10 seconds, formulations are placed at the center of the thermo-regulated measuring plate using a spatula. The measuring system is lowered down and a 0.051 mm gap is left between the measuring system and the measuring plate. 21 viscosity measurement points are determined across the 10 to 1000 $s^{-1}$ shear rate range. Given values are the ones obtained at 100 $s^{-1}$.

Representative drugs and biologically active agents to be used in the invention include, without limitation, peptides, proteins, antibodies, fragments of antibodies, desensitizing agents, antigens, vaccines, vaccine antigens, anti-infectives, antidepressants, stimulants, opiates, antipsychotics, atypical antipsychotics, glaucoma medications, antianxiety drugs, antiarrhythmics, antibacterials, anticoagulents, anticonvulsants, antidepressants, antimetics, antifungals, antineoplastics, antivirals, antibiotics, antimicrobials, antiallergenics, anti-diabetics, steroidal anti-inflammatory agents, decongestants, miotics, anticholinergics, sympathomimetics, sedatives, hypnotics, psychic energizers, tranquilizers, hormones, androgenic steroids, estrogens, progestational agents, humoral agents, prostaglandins, analgesics, corticosteroids, antispasmodics, antimalarials, antihistamines, cardioactive agents, non-steroidal anti-inflammatory agents, antiparkinsonian agents, antihypertensive agents, beta-adrenergic blocking agents, nutritional agents, gonadotrophin releasing hormone agonists, insecticides, anti-helminthic agents or combinations thereof.

The pharmaceutically active ingredient may be meloxicam, bupivacaine, tamsulosin, octreotide, tadalafil, empaglifozin, tenofovir, liothyronine, or combinations thereof.

Combinations of drugs can be used in the biodegradable drug delivery composition of this invention. For instance, if one needs to treat Lupus erythematosus, non-steroidal anti-inflammatory agents and corticosteroids can be administered together in the present invention.

Veterinary medicaments such as medicines for the treatment of worms or vaccines for animals are also part of the present invention.

Viral medicaments for plants such as those viruses from Potyviridae, Geminiviridae, the *Tospovirus* genus of Bunyaviridiae and Banana streak virus are also encompassed by the present invention. Also, medicaments for tobacco mosaic virus, turnip crinkle, barley yellow dwarf, ring spot watermelon and cucumber mosaic virus can be used in the biodegradable drug delivery composition of the invention.

To those skilled in the art, other drugs or biologically active agents that can be released in an aqueous environment can be utilized in the described delivery system. Also, various forms of the drugs or biologically active agents may be used. These include without limitation forms such as uncharged molecules, molecular complexes, salts, ethers, esters, amides, etc., which are biologically activated when injected into the animal or plant or used as a spatial formulation such that it can be applied on or inside the body of an animal or plant or as a rod implant.

The pharmaceutically effective amount of an active ingredient may vary depending on the active ingredient, the extent of the animal's or plants medical condition and the time required to deliver the active ingredient. There is no critical upper limit on the amount of active ingredient incorporated into the polymer solution as long as the solution or suspension has a viscosity which is acceptable for injection through a syringe needle and that it can effectively treat the medical condition without subjecting the animal or plant to an overdose. The lower limit of the active ingredient incorporated into the delivery system is dependent simply upon the activity of the active ingredient and the length of time needed for treatment.

In the biodegradable drug delivery composition of the present invention, the pharmaceutically effective amount can be released gradually over an extended period of time. This slow release may be continuous or discontinuous, linear or non-linear and can vary due to the composition of the multi-branched copolymer.

The active ingredient can be released for a duration of between 1 day to 1 year or longer depending upon the type of treatment needed and the biodegradable drug delivery composition used. In one embodiment the biodegradable drug delivery composition can deliver the active ingredient for at least 1 day, optionally at least 3 days, optionally at least 7 days. In another embodiment the biodegradable drug delivery composition can deliver the active ingredient for at least 30 days. In one embodiment the biodegradable drug delivery composition can deliver the active ingredient for at least 90 days. In yet another embodiment the biodegradable drug delivery composition can deliver an active ingredient for 1 year or longer.

The biodegradable drug delivery composition can be an injectable liquid, preferably at room temperature, and can be injected through a syringe without excessive force. These biodegradable drug delivery compositions are also in situ forming and biodegradable and turn into solid depots when injected into the animal or plant.

The composition can further comprise a pharmaceutically acceptable carrier, adjuvant or vehicle.

The adjuvant can be formulated simultaneously when mixing the drug. In this regard the adjuvants that can be used are alum, aluminium phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The vehicle can be any diluent, additional solvent, filler or binder that may alter the delivery of the active ingredient when needed in the biodegradable drug delivery composition. Examples include small amounts of triglycerides such as triacetin or tripropionin.

In one embodiment the composition may comprise an organic solvent. The organic solvent may be selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), 2-pyrrolidone, tetraglycol, triacetin, tributyrin, tripropionin, glycofurol, and mixtures thereof. In one embodiment DMSO, NMP, tripropionin or mixtures thereof can be used as solvents.

LIST OF ABBREVIATIONS

DB Diblock (mPEG-PLA)
DMSO Dimethyl sulfoxide
EO Ethylene oxide
GPC Gel permeation chromatography
UPLC Ultra-performance liquid chromatography
KRT Krebs-Ringer-Tris buffer
LA Lactic acid
mPEG methoxy-poly(ethylene glycol)
mPEG-PLA methoxy-poly(ethylene glycol)-b-poly(lactic acid)
PBS Phosphate buffer saline
PDI Polydispersity index
PEG Poly(ethylene glycol)
PLA-PEG-PLA Poly(lactic acid)-b-poly(ethylene glycol)-b-poly(lactic acid)
Poly(lactic acid) PLA
TB Triblock (PLA-PEG-PLA)

Results indicate that the star-shaped copolymer-based formulation exhibits slower release kinetics compared to the linear copolymer-based formulation with a comparable molecular weight and an identical total copolymer content. Indeed, formulation F397 shows slower release kinetics than formulation F396.

Figure 1:
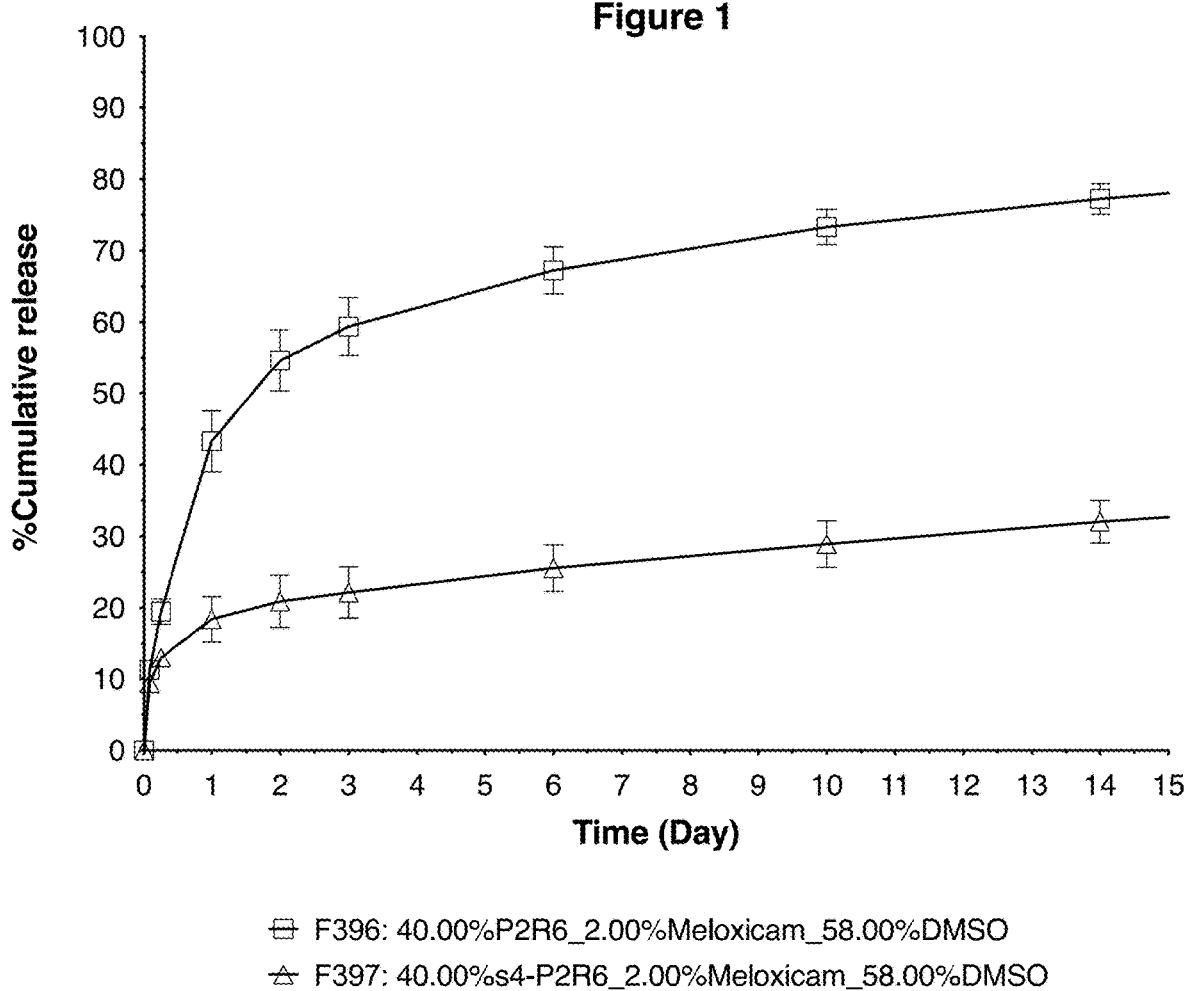
FIG. 1 shows the percentage in vitro cumulative release of meloxicam over time from two different formulations: Formulation F396 (□) containing 40.00% of P2R6 triblock copolymer with 2.00% active ingredient (API) and 58.00% of DMSO and formulation F397 (Δ) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1.
Figure 2:
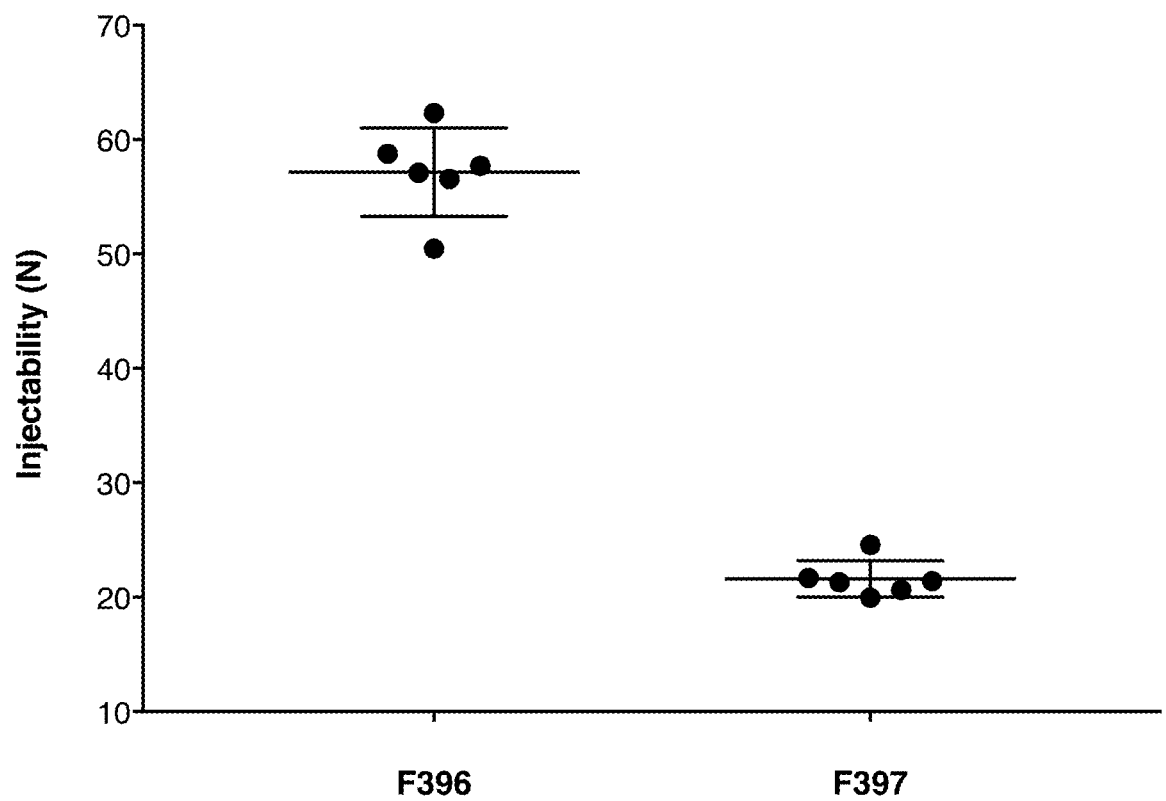

FIG. 2 displays injectability values of formulations F396 and F397. Data demonstrate that for identical loading of copolymer and a comparable molecular weight, the star-shaped copolymer-based formulation has lower injectability than the linear copolymer-based formulation. Thus, injectability values for formulation F397 are below those of F396. Table 3 presents the details of the injectability data.

Figure 3:
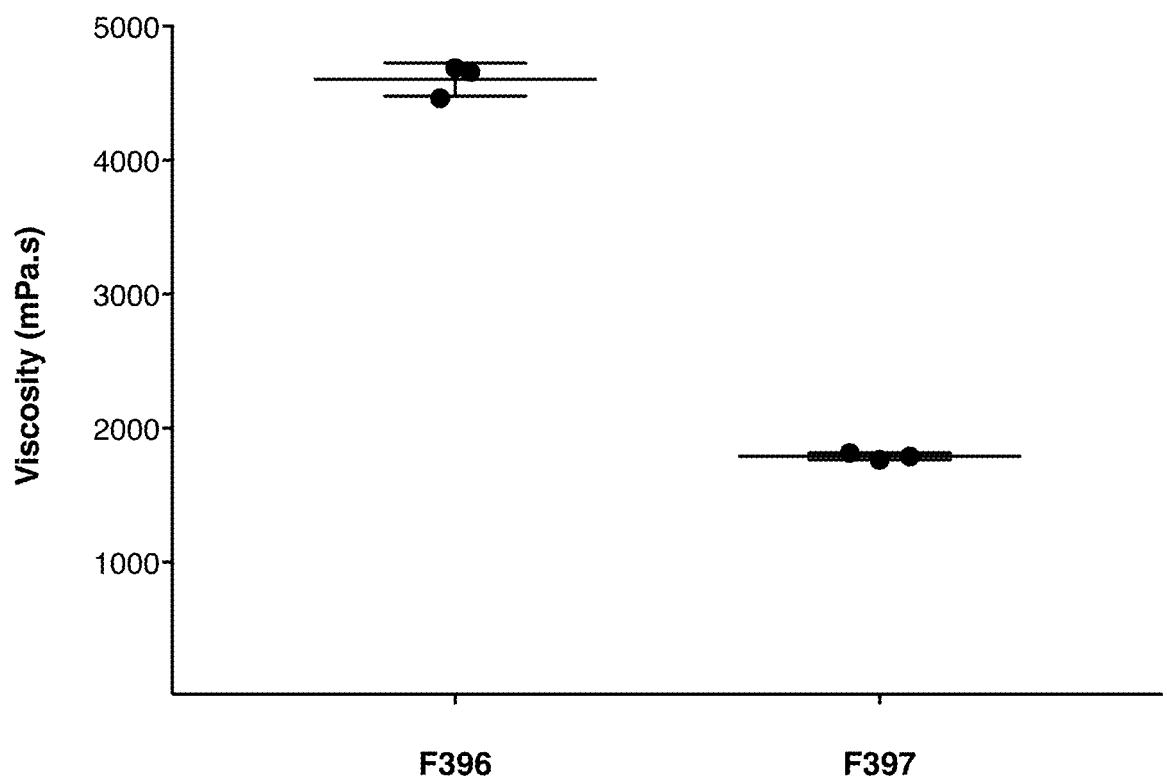

FIG. 3 presents viscosity values of formulations F396 and F397. Data show that for identical loading of copolymer and a comparable molecular weight, the star-shaped copolymer-based formulation has a lower viscosity than the linear copolymer-based formulation. Thus, viscosity values of F397 are below the viscosity values of F396. Table 4 presents the details of the viscosity data.

Figure 4:
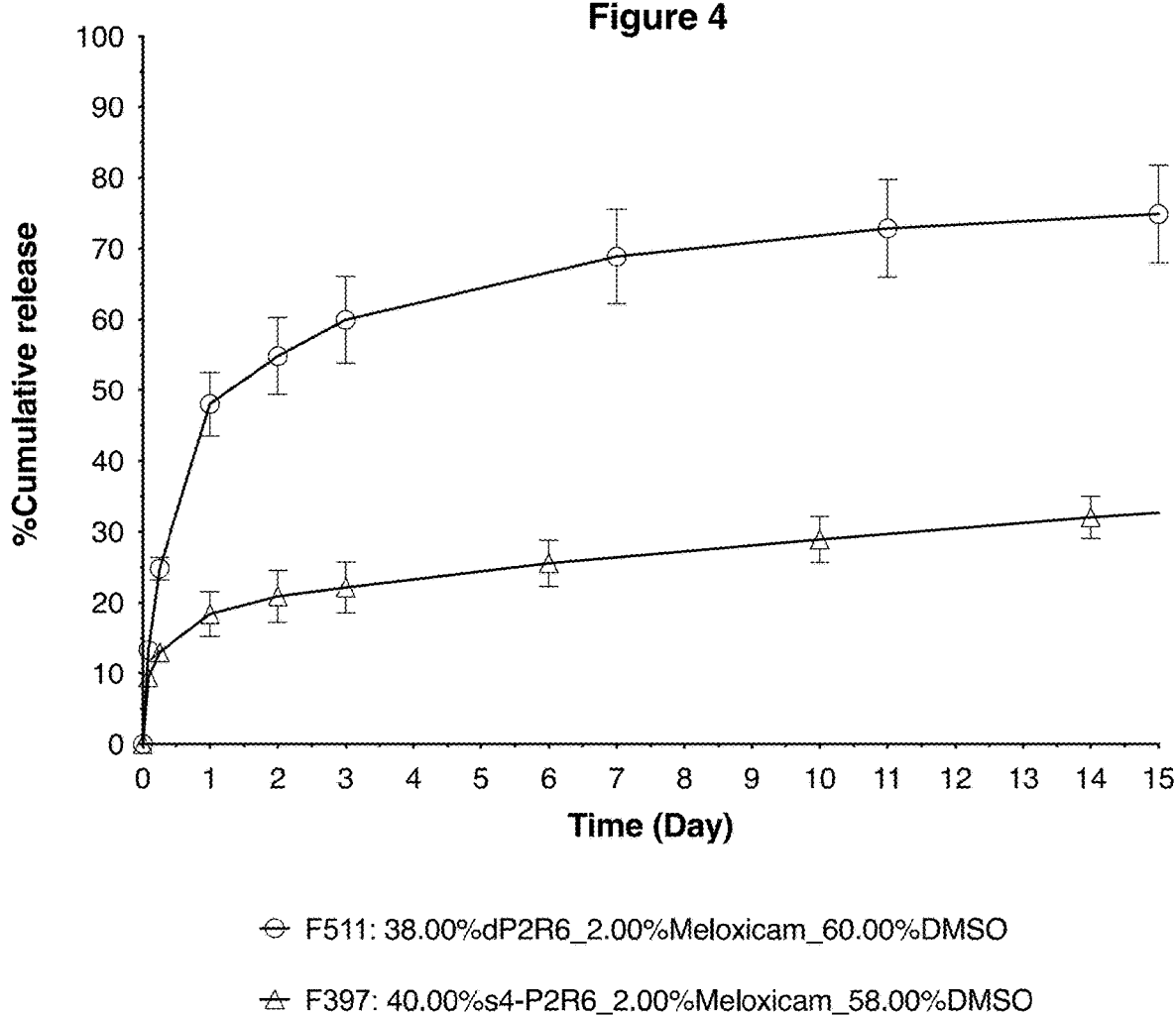

FIG. 4 shows the percentage in vitro cumulative release of meloxicam over time from two different formulations: Formulation F511 (○) containing 38.00% of dP2R6 diblock copolymer with 2.00% active ingredient (API) and 60.00% of DMSO and formulation F397 (Δ) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1.

Results indicate that the star-shaped copolymer-based formulation leads to slower release kinetics compared to the linear copolymer-based formulation with a comparable molecular weight and similar total copolymer content. Indeed, formulation F397 shows slower release kinetics than formulation F511.

Figure 5:
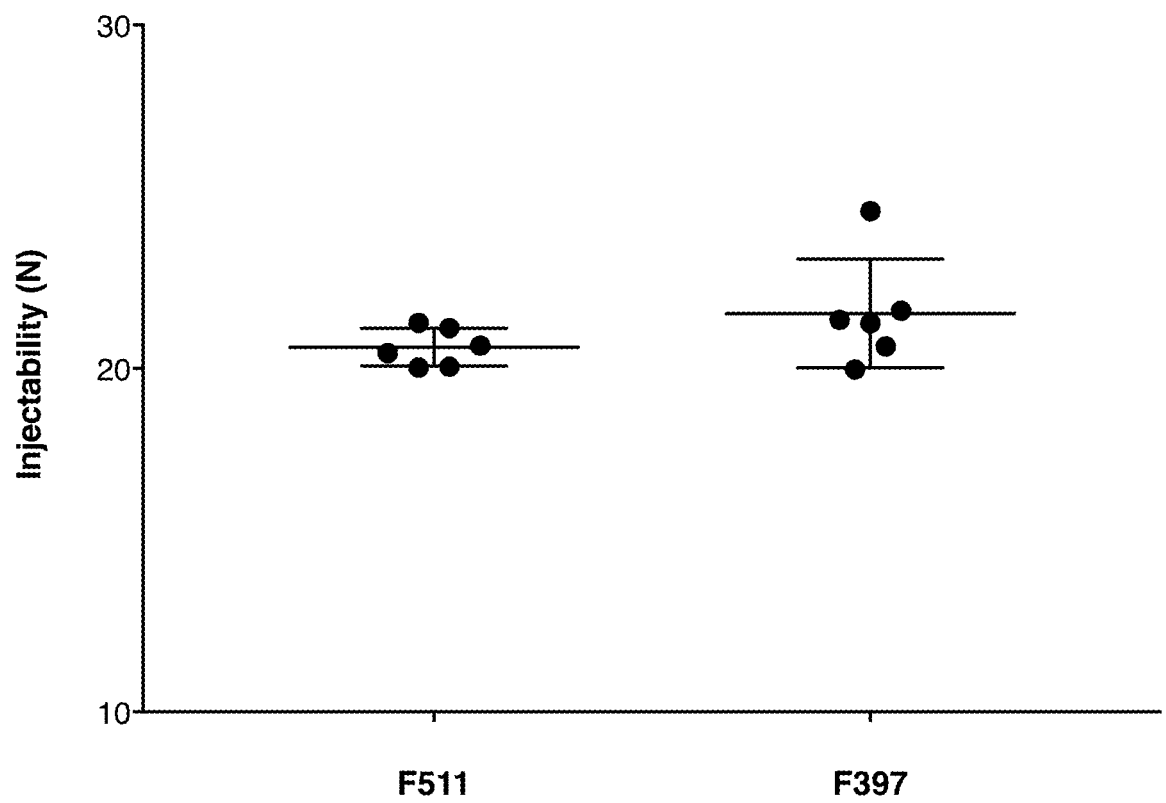

FIG. 5 presents injectability values of formulation F397 and formulation F511. Data demonstrate that for similar loading of copolymer and a comparable molecular weight, both formulations have comparable injectability values. Thus, for similar injectability, the star-shaped copolymer-based formulation shows slower release kinetics. Table 3 presents the details of the injectability data.

Figure 6:
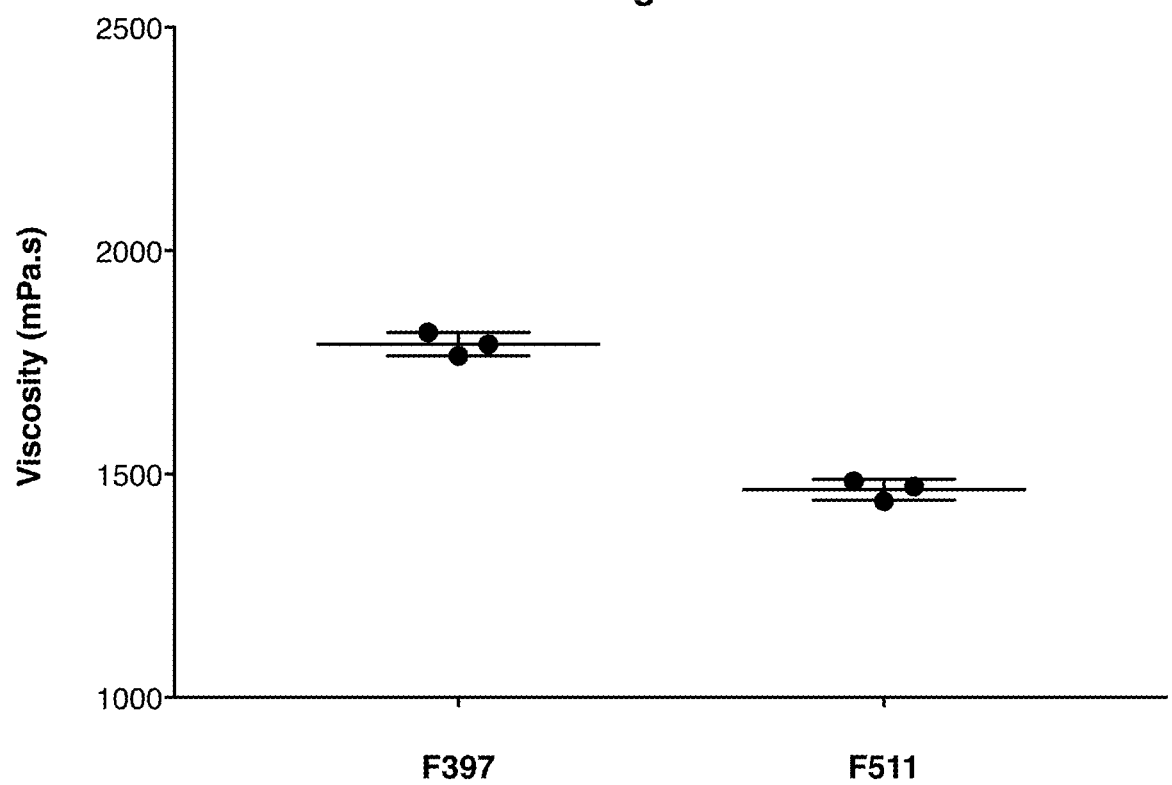

FIG. 6 displays the viscosity values of formulations F397 and F511. Data show that for similar loading of copolymer and a comparable molecular weight, both the star-shaped copolymer-based formulation and linear copolymer-based formulation have similar viscosity values. Thus, for similar viscosity values, the star-shaped copolymer-based formulation shows slower release kinetics. Table 4 presents the details of the viscosity data.

Figure 7:
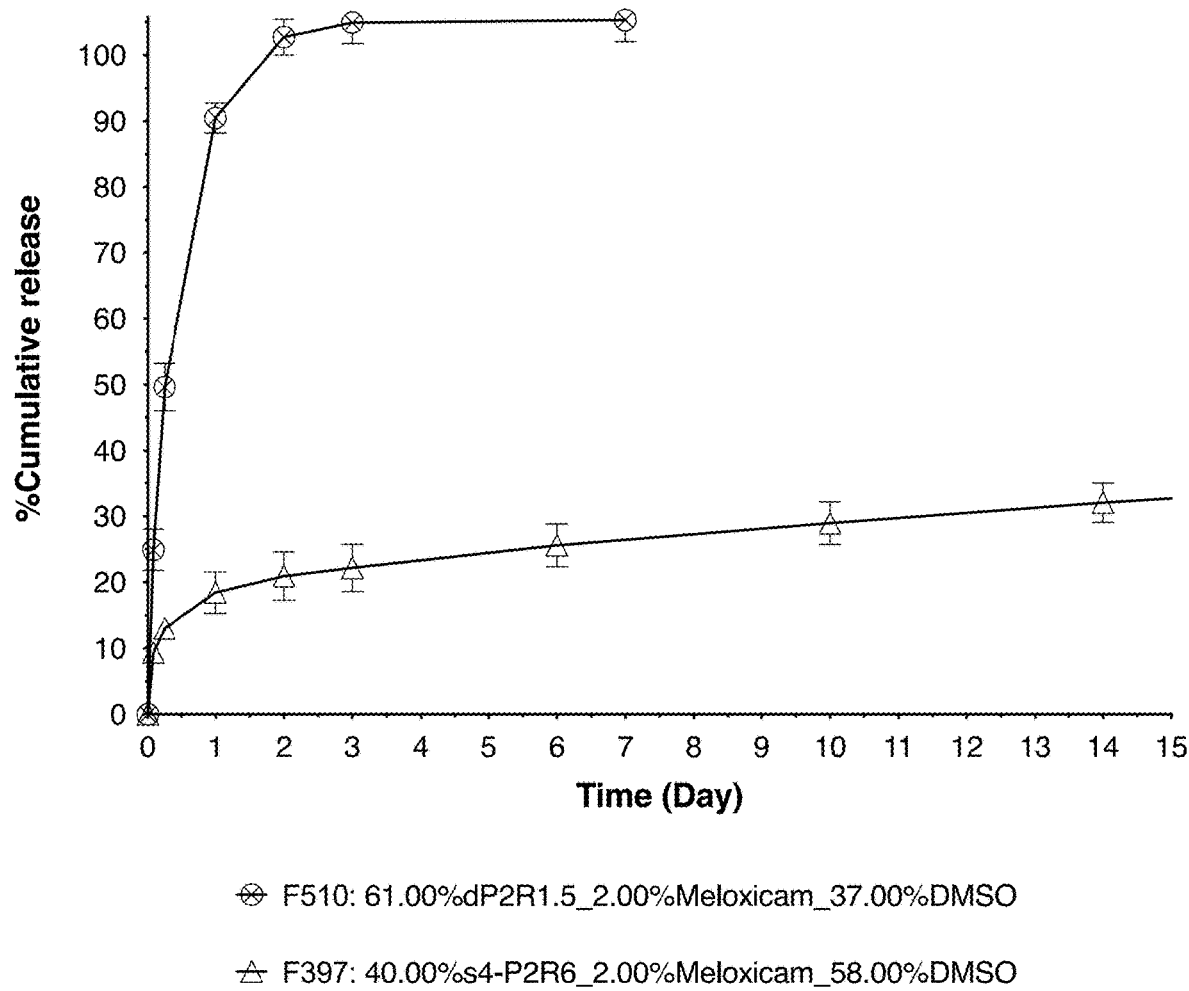

FIG. 7 shows the percentage in vitro cumulative release of meloxicam over time from two different formulations: Formulation F510 (⊗) containing 61.00% of dP2R1.5 diblock copolymer with 2.00% active ingredient (API) and 37.00% of DMSO and formulation F397 (Δ) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1.

Data show that the star-shaped copolymer-based formulation leads to slower release kinetics compared to that of the linear copolymer-based formulation with a comparable polyester chain length per branch. Indeed, formulation F397 shows slower release kinetics compared to formulation F510.

Figure 8:
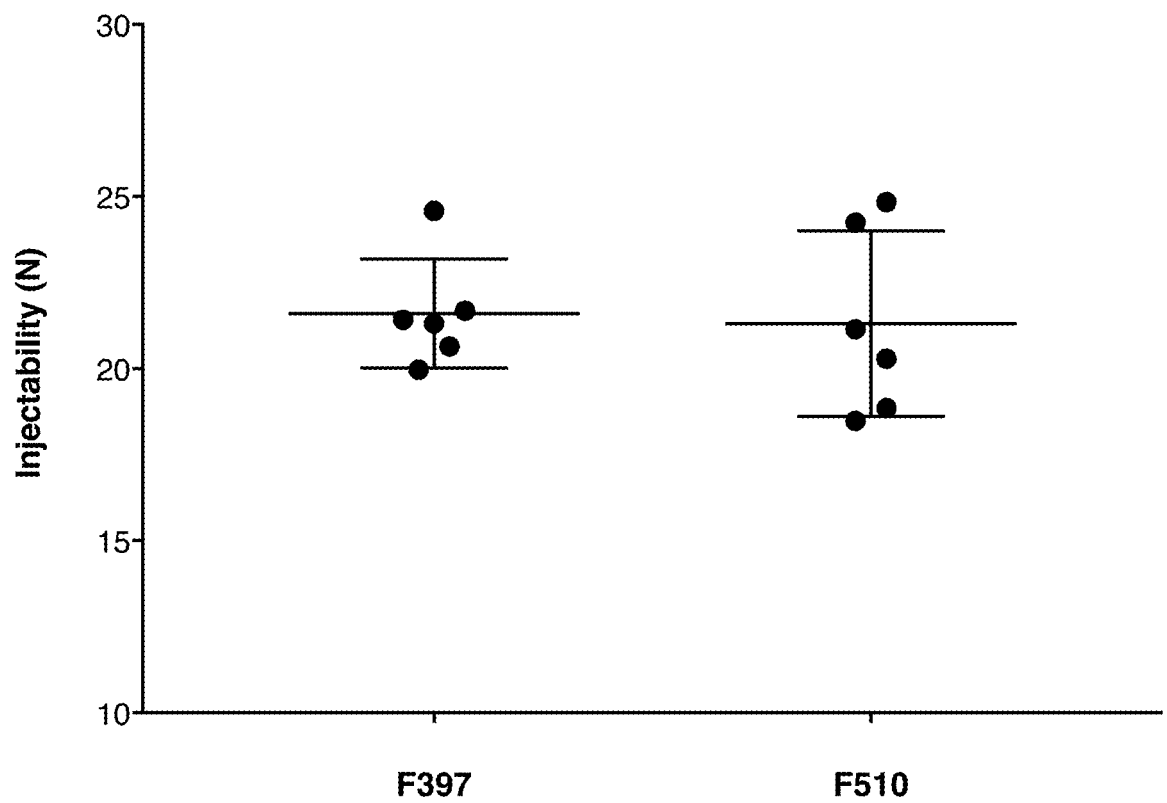

FIG. 8 displays the injectability values of formulations F397 and F510. Data demonstrate that for similar injectability and similar polyester chain length per branch, the star-shaped copolymer-based formulation shows slower release kinetics. Table 3 presents the details of the injectability data.

Figure 9:
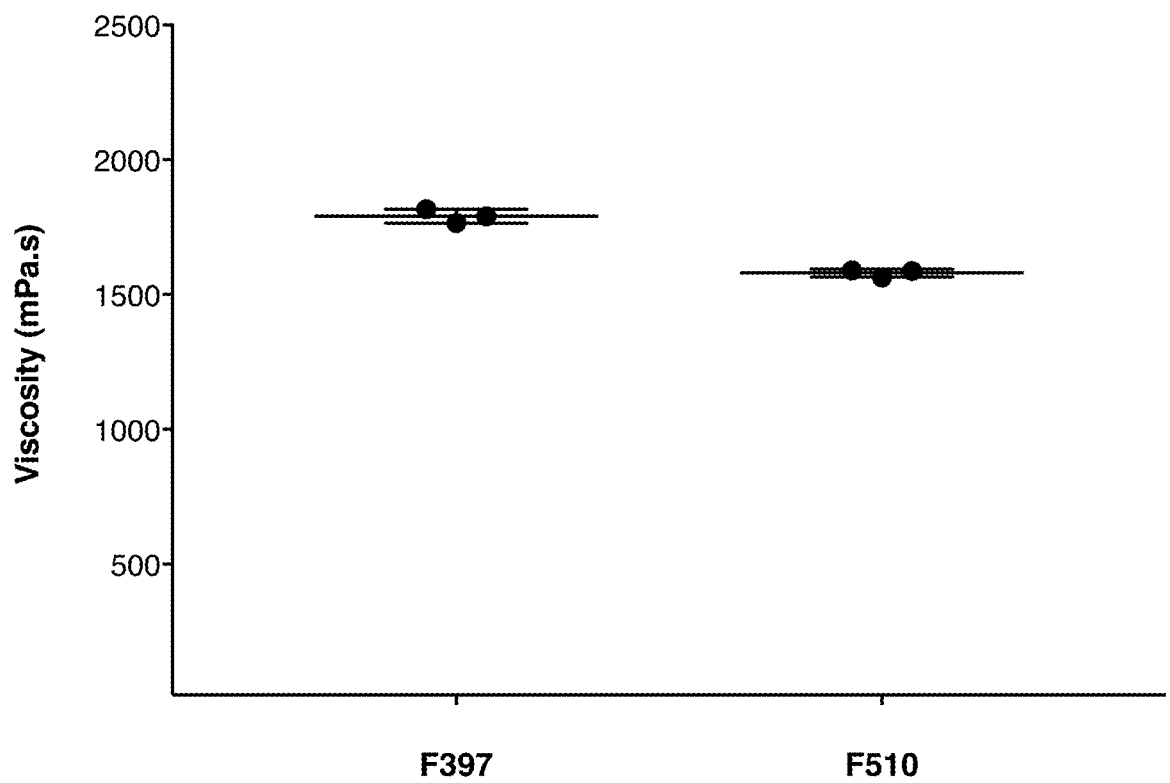

FIG. 9 shows the viscosity values of formulations F397 and F510. Data demonstrate that for similar viscosity and similar polyester chain length per branch, the star-shaped copolymer-based formulation leads to slower release kinetics. Table 4 presents the details of the viscosity data.

Figure 10:
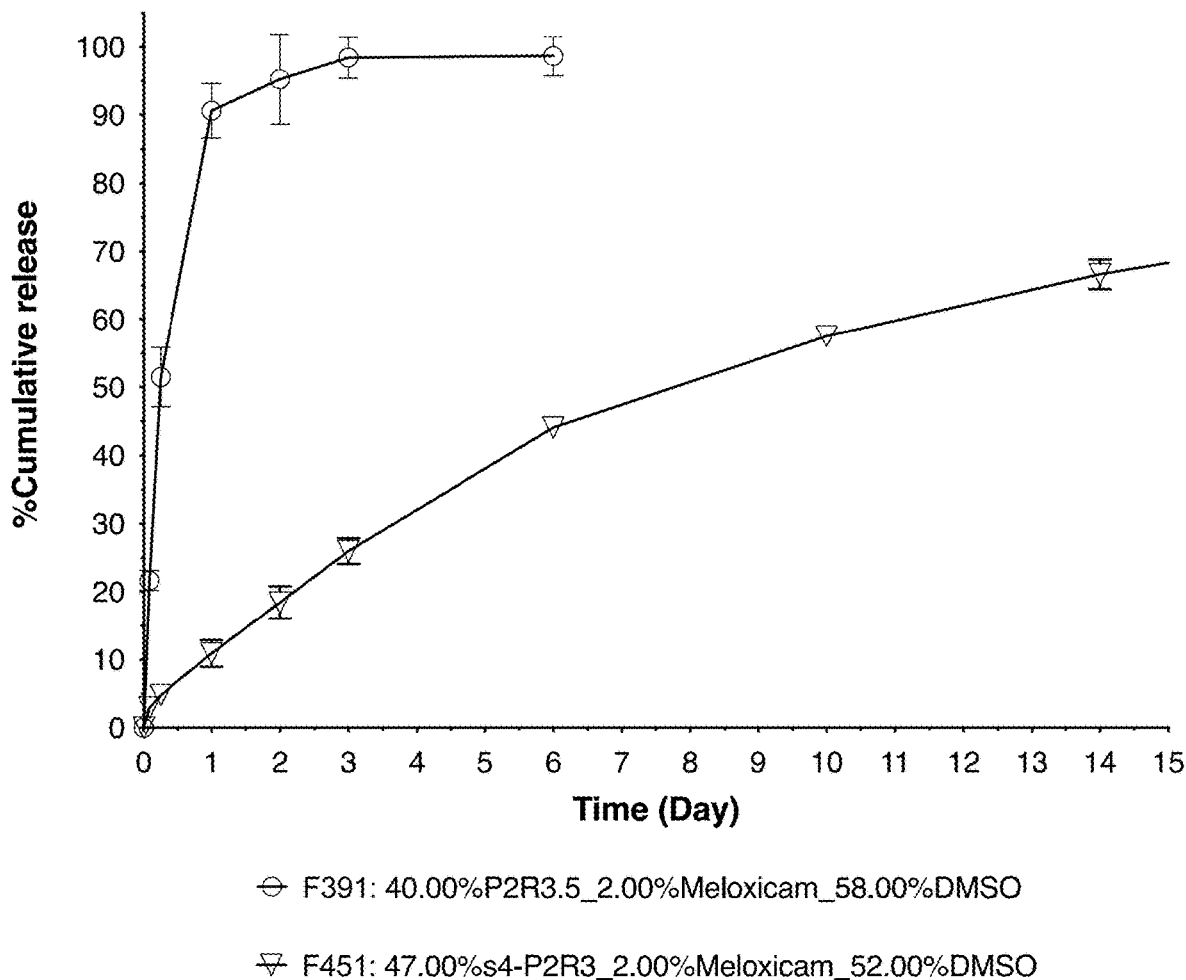

FIG. 10 shows the percentage in vitro cumulative release of meloxicam over time from two different formulations: Formulation F391 (○) containing 40.00% of P2R3.5 triblock copolymer with 2.00% active ingredient (API) and 58.00% of DMSO and formulation F451 (∇) containing 47.00% of s4-P2R3 star-shaped copolymer with 2.00% active ingredient (API) and 51.00% of DMSO. In vitro release tests have been conducted according to set up 1 in table 2, example 3. The specific block copolymer formulations are set forth in Table 1.

The results indicate that the star-shaped copolymer-based formulation leads to slower release kinetics compared to the linear copolymer-based formulation with a comparable molecular weight. Indeed, formulation F451 shows slower release kinetics compared to formulation F391.

Figure 11:
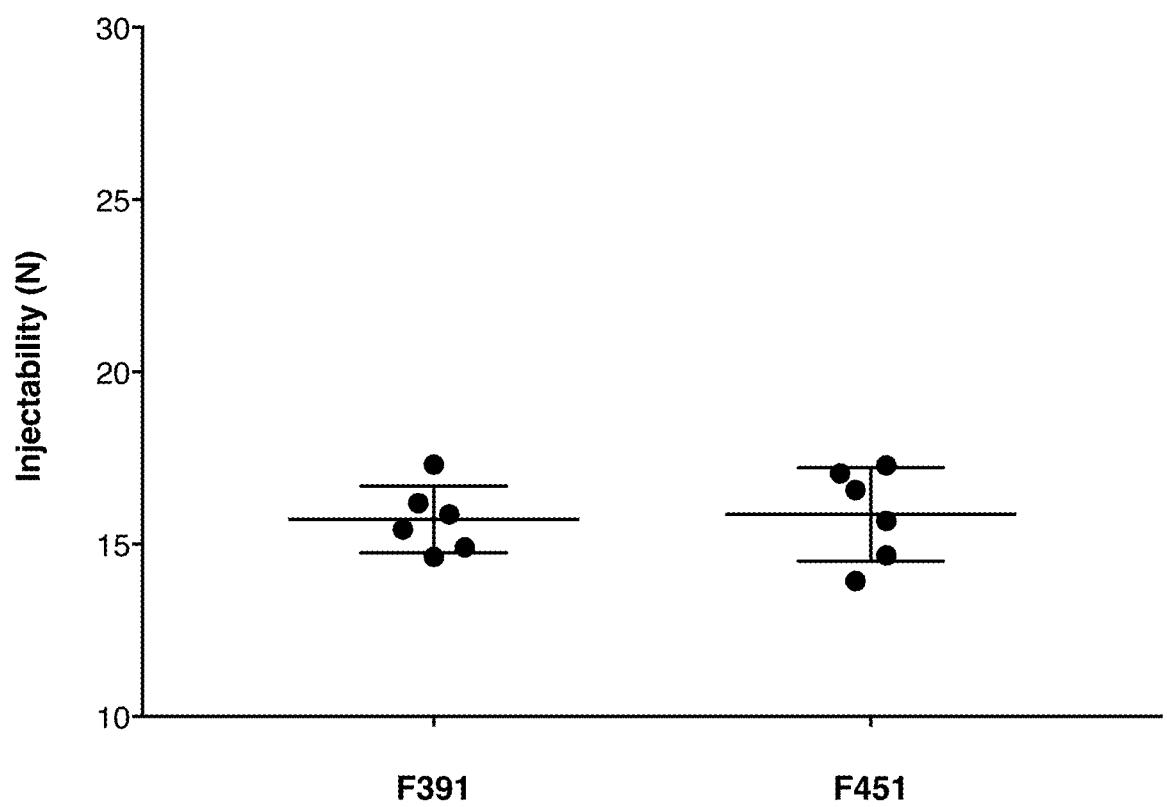

FIG. 11 shows the injectability values of formulations F391 and F451. Data demonstrate that for similar injectability and similar molecular weight, the star-shaped copolymer-based formulation shows slower release kinetics. Table 3 presents the details of the injectability data.

Figure 12:
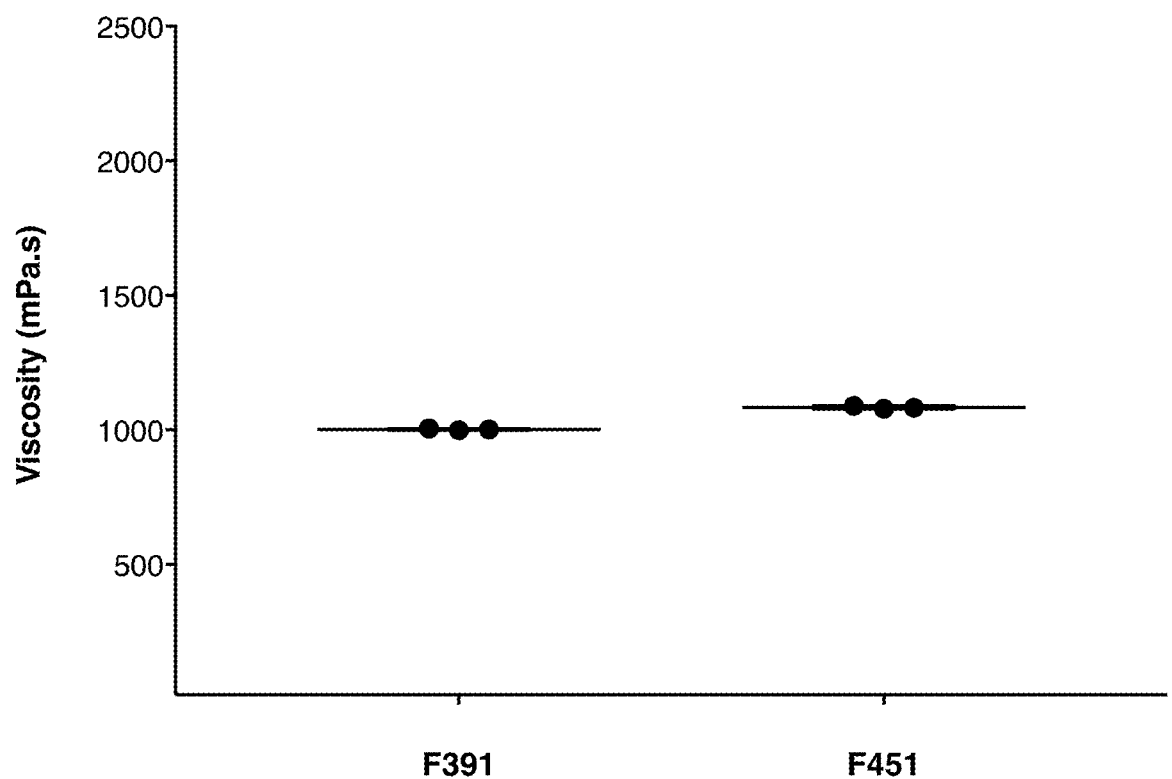

FIG. 12 displays the viscosity values of F391, and F451. Data demonstrate that for similar viscosity and similar molecular weight, the star-shaped copolymer-based formulation shows slower release kinetics than that of the linear copolymer-based formulation. Table 4 presents the details of the viscosity data.

Figure 13:
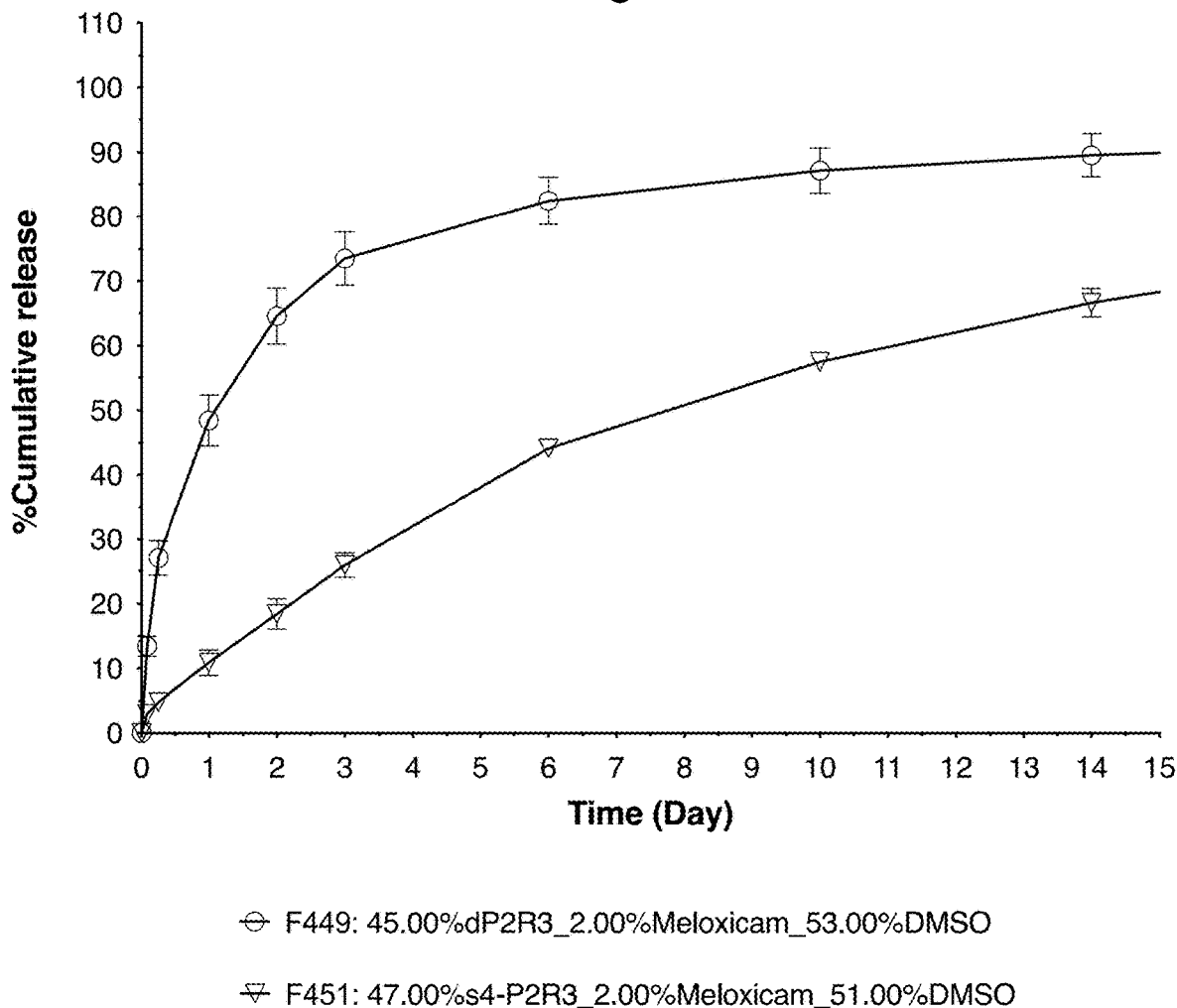

FIG. 13 shows the percentage total in vitro cumulative release of meloxicam over time from two different formulations: Formulation F449 (○) containing 45.00% of dP2R3 diblock copolymer with 2.00% active ingredient (API) and 53.00% of DMSO and formulation F451 (∇) containing 47.00% of s4-P2R3 star-shaped copolymer with 2.00% active ingredient (API) and 51.00% of DMSO. In vitro release tests have been conducted according to set up 1 in table 2, example 3. The specific block copolymer formulations are set forth in Table 1.

Results indicate that the star-shaped copolymer-based formulation leads to slower release kinetics compared to that of the linear copolymer-based formulation with a comparable molecular weight. Indeed, formulation F451 shows slower release kinetics compared to F449.

Figure 14:
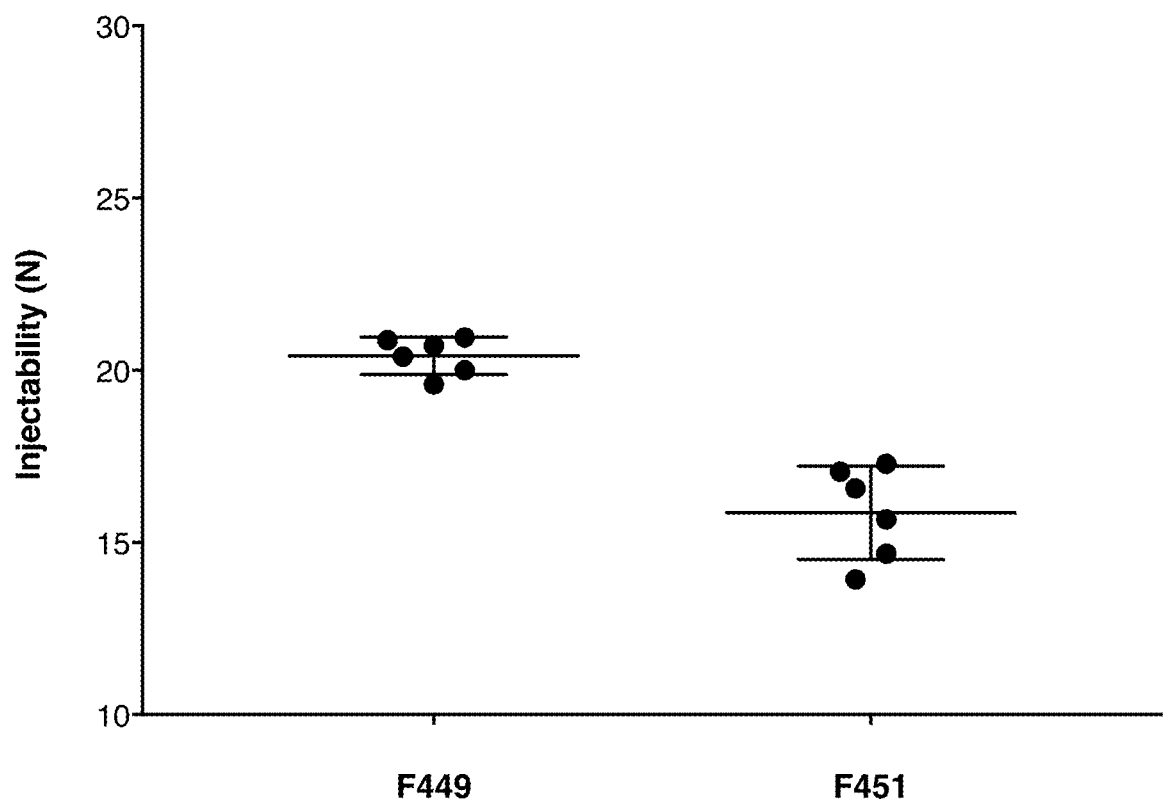

FIG. 14 presents injectability values of formulations F449 and F451. Data demonstrate that for a lower injectability and a similar molecular weight, the star-shaped copolymer-based formulation shows slower release kinetics than that of the linear copolymers-based formulation. Table 3 presents the details of injectability data.

Figure 15:
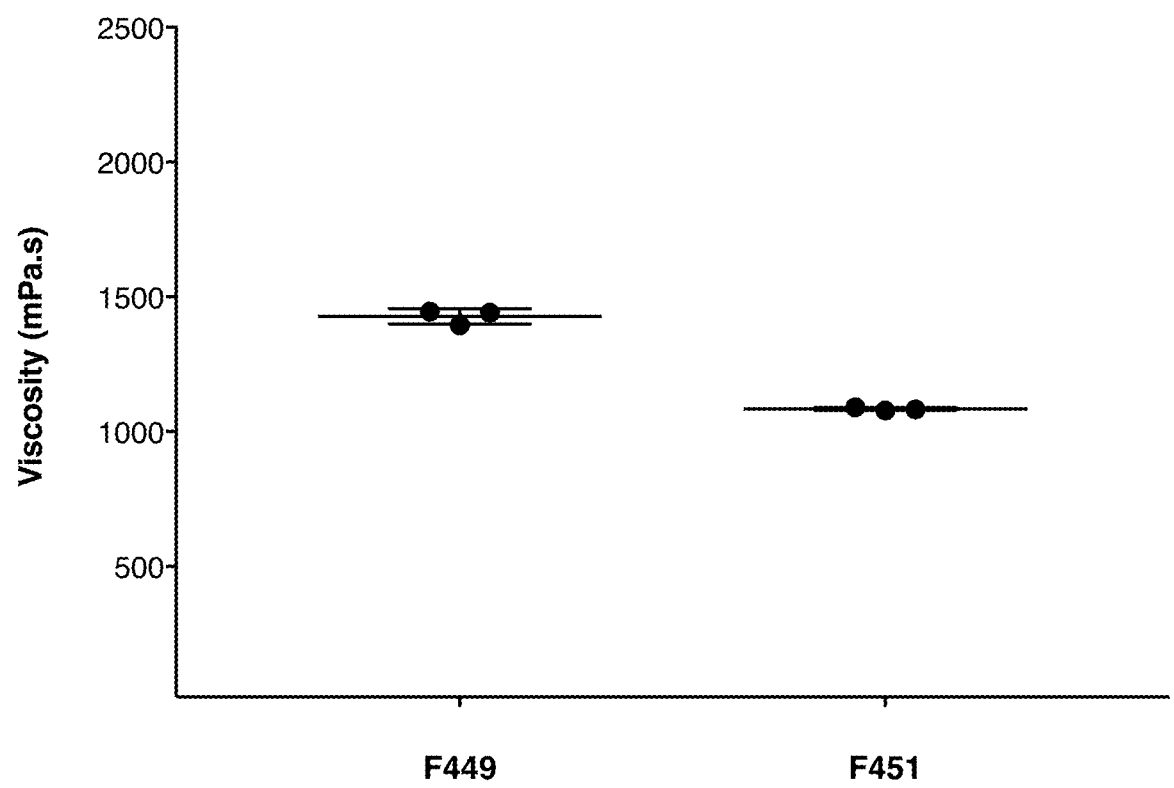

FIG. 15 displays viscosity values of formulations F449 and F451. Data demonstrate that with lower viscosity values and similar molecular weight, the star-shaped copolymer-based formulation leads to slower release kinetics than that of the linear copolymers-based formulation. Table 4 presents the details of viscosity data.

Figure 16:
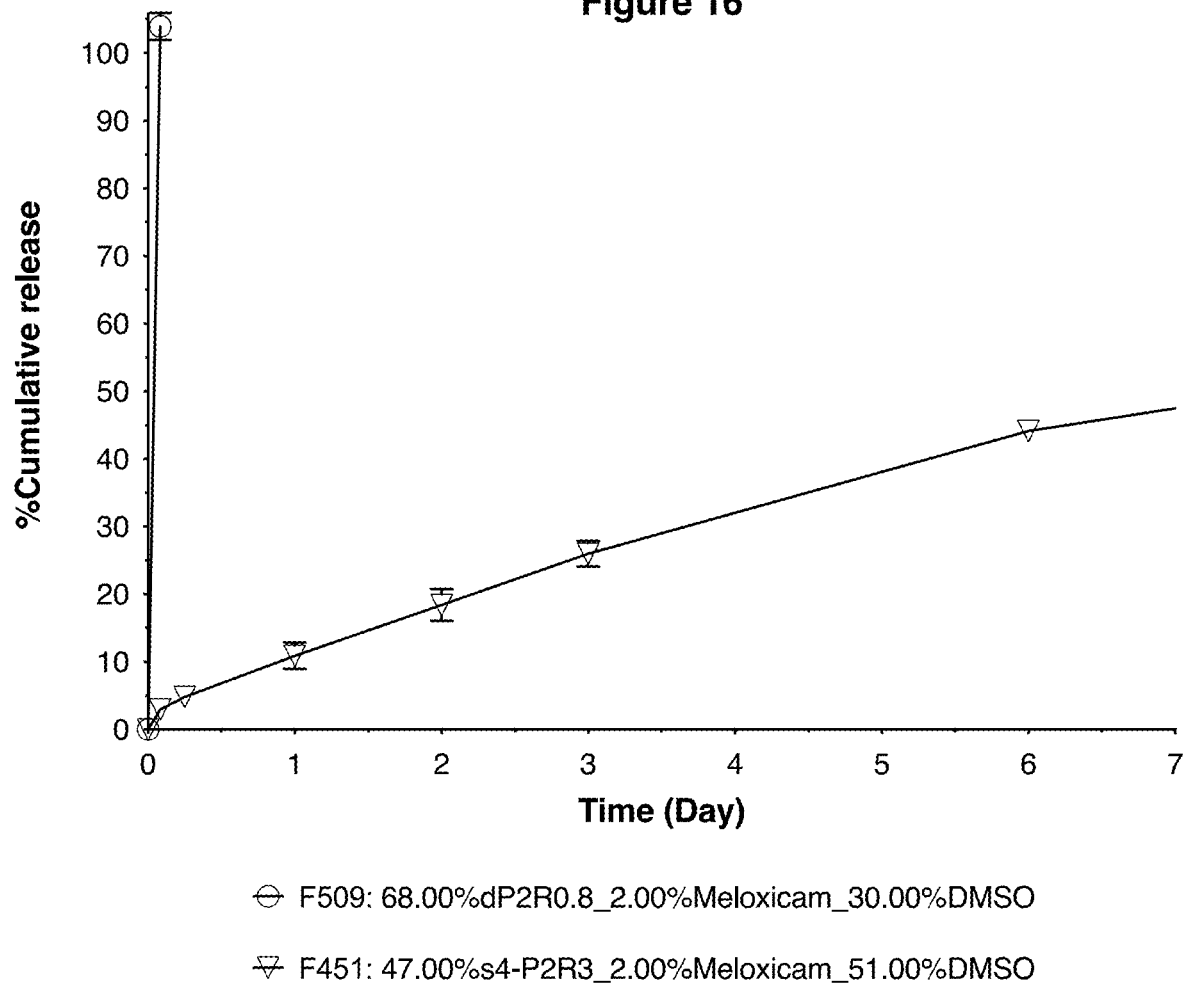

FIG. 16 displays the percentage in vitro cumulative release of meloxicam over time from two different formulations: Formulation F509 (○) containing 68.00% of dP2R0.8 diblock copolymer with 2.00% active ingredient (API) and 30.00% of DMSO and formulation F451 (∇) containing 47.00% of s4-P2R3 star-shaped copolymer with 2.00% active ingredient (API) and 51.00% of DMSO. In vitro release tests have been conducted according to set up 1 in table 2, example 3. The specific block copolymer formulations are set forth in Table 1.

Data show that the star-shaped copolymer-based formulation leads to a slower release kinetics compared to the linear copolymers-based formulation with a comparable polyester chain length per branch. Indeed, formulation F451 shows slower release kinetics compared to F509.

Figure 17:
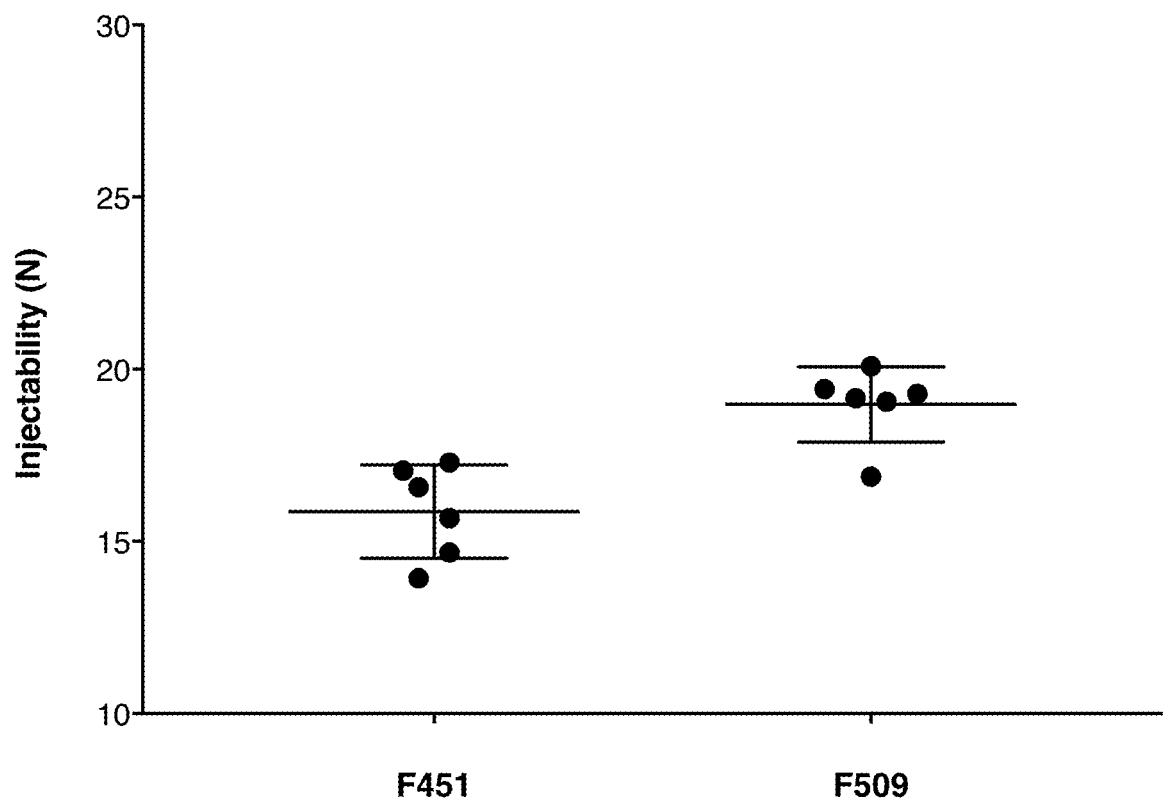

FIG. 17 shows injectability values of formulations F451 and F509. Data demonstrate that for comparable injectability values and a similar polyester chain length per arm, the star-shaped copolymer-based formulation shows slower release kinetics compared to that of the linear copolymer-based formulation. Table 3 presents the details of the injectability data.

Figure 18:
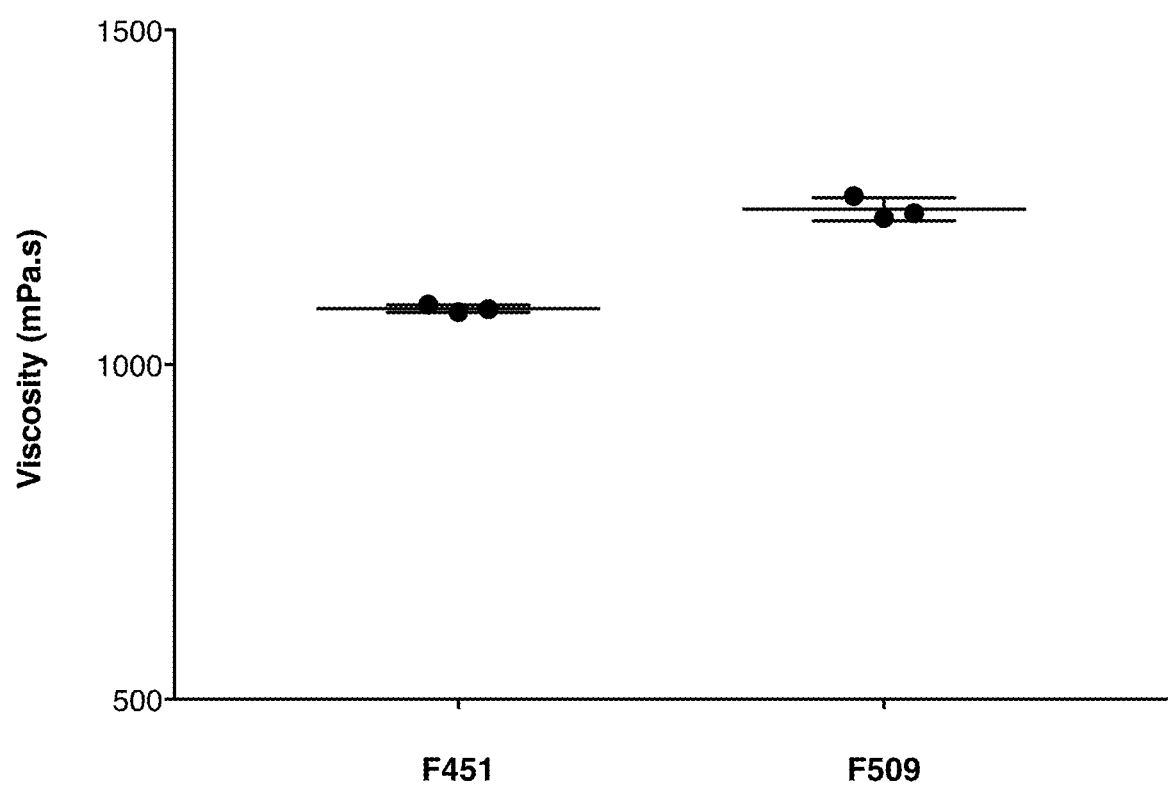

FIG. 18 presents the viscosity values of formulations F451 and F509. Data demonstrate that for a comparable viscosity and similar polyester chain length per arm, the star-shaped copolymer-based formulation shows slower release kinetics compared to that of the linear copolymer-based formulation. Table 4 presents the details of viscosity data.

Figure 19:
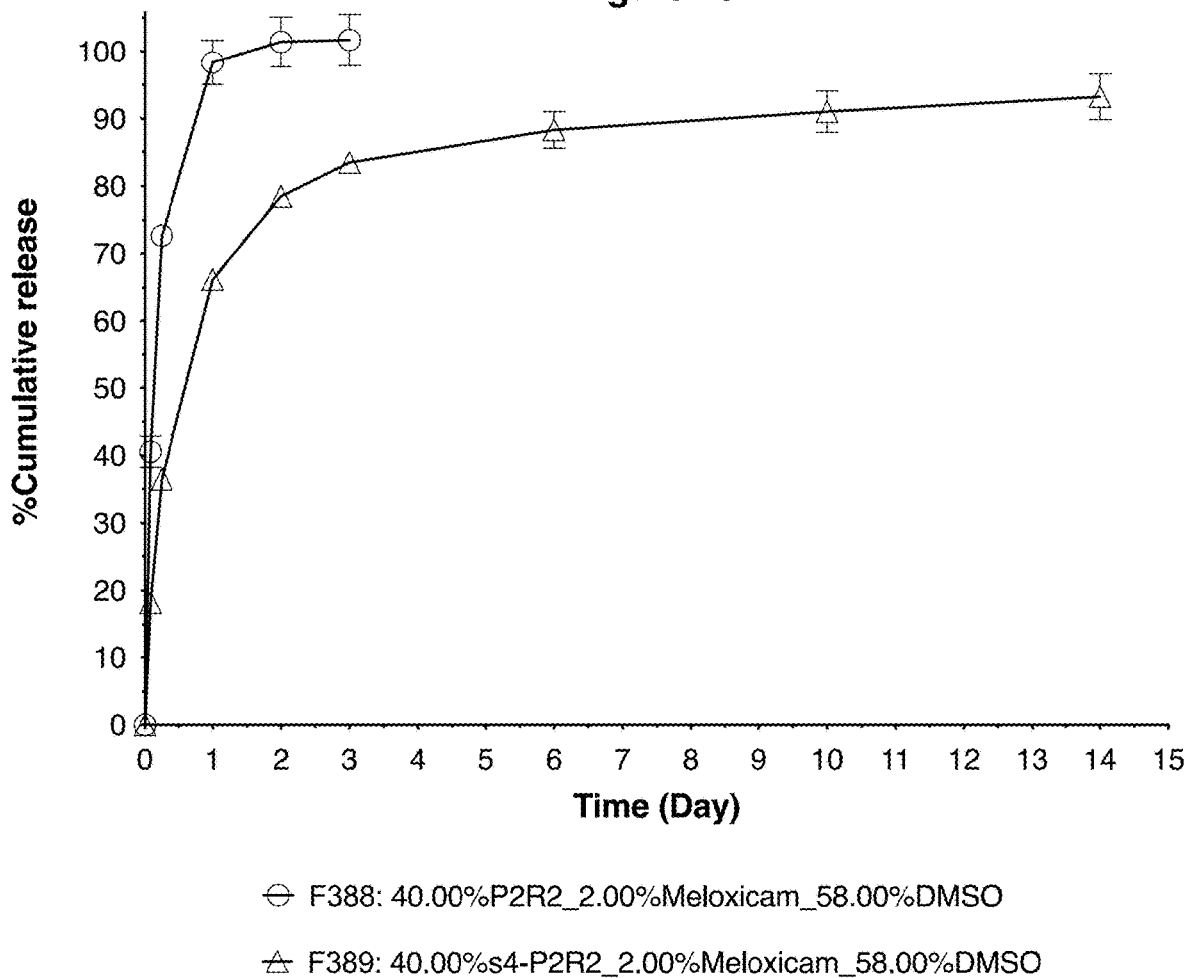

FIG. 19 displays the percentage in vitro cumulative release of meloxicam over time from two different formulations: Formulation F388 (○) containing 40.00% of P2R2 triblock copolymer with 2.00% active ingredient (API) and 58.00% of DMSO and formulation F389 (Δ) containing 40.00% of s4-P2R2 star-shaped copolymer with 2.00% active ingredient (API) and 58.00% of DMSO. In vitro release tests have been conducted according to set up 1 in table 2, example 3. The specific block copolymer formulations are set forth in Table 1.

Results indicate that the star-shaped copolymer-based formulation exhibits slower release kinetics compared to that of the linear copolymer-based formulation with a comparable molecular weight. Formulation F389 shows slower release kinetics than formulation F388.

Figure 20:
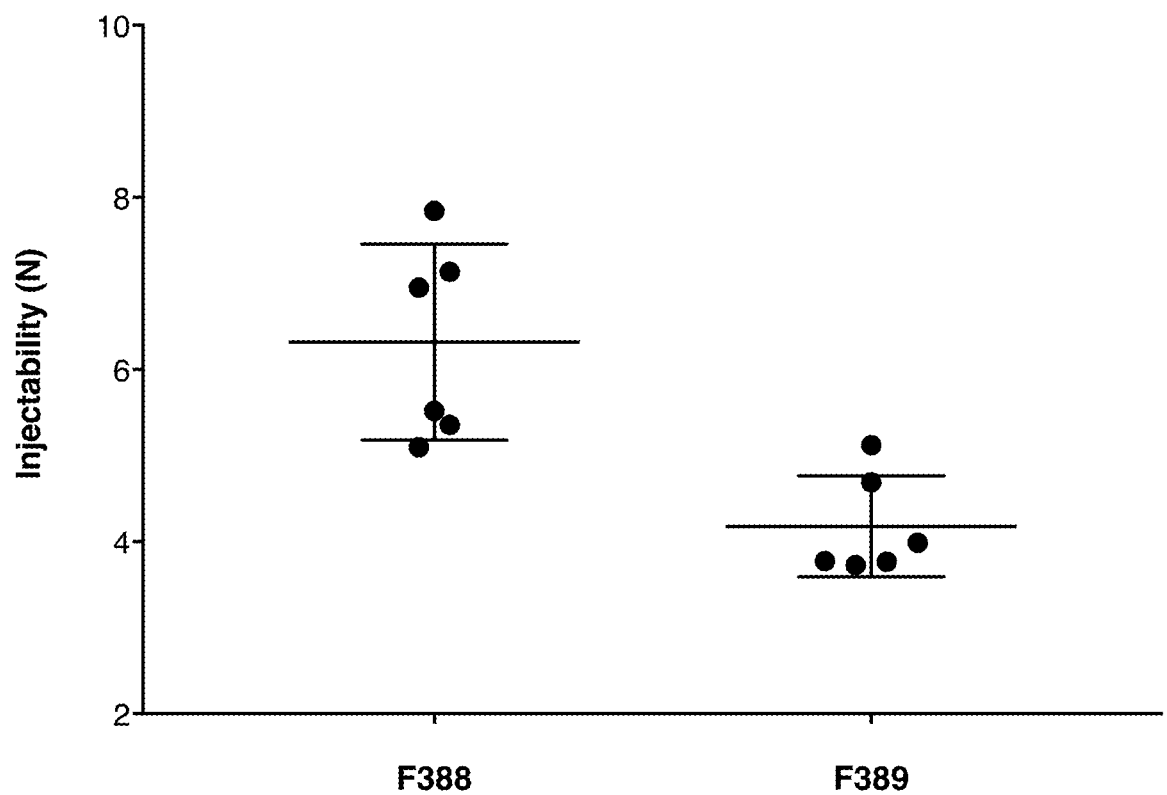

FIG. 20 presents injectability values of formulations F388 and F389. Data demonstrate that for an identical copolymer content and a comparable molecular weight the star-shaped copolymer-based formulation shows a lower injectability and a slower release kinetics compared to those of the linear copolymer-based formulation. Table 3 presents the details of injectability data.

Figure 21:
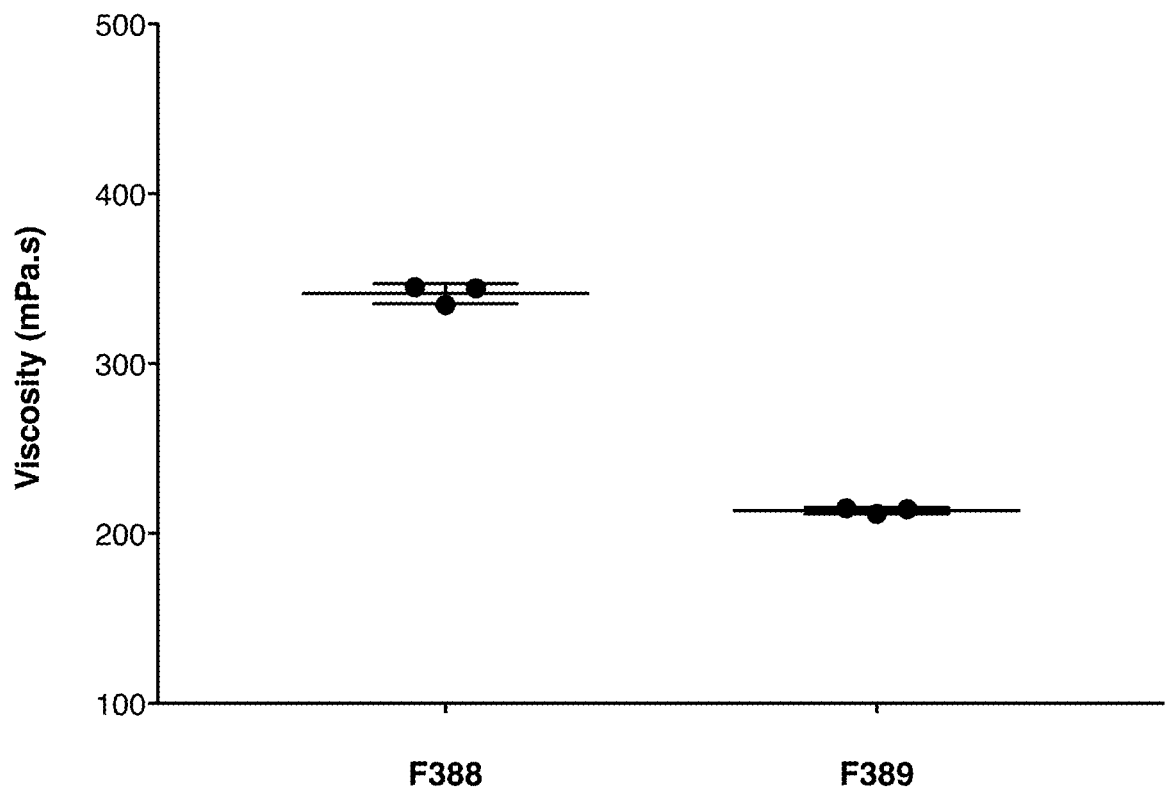

FIG. 21 presents viscosity values of formulations F388 and F389. Data demonstrate that for the same copolymer content and a comparable molecular weight the star-shaped copolymer-based formulation shows a lower viscosity and a slower release kinetics compared to those of the linear copolymer-based formulation. Table 4 presents the details of viscosity data.

Figure 22:
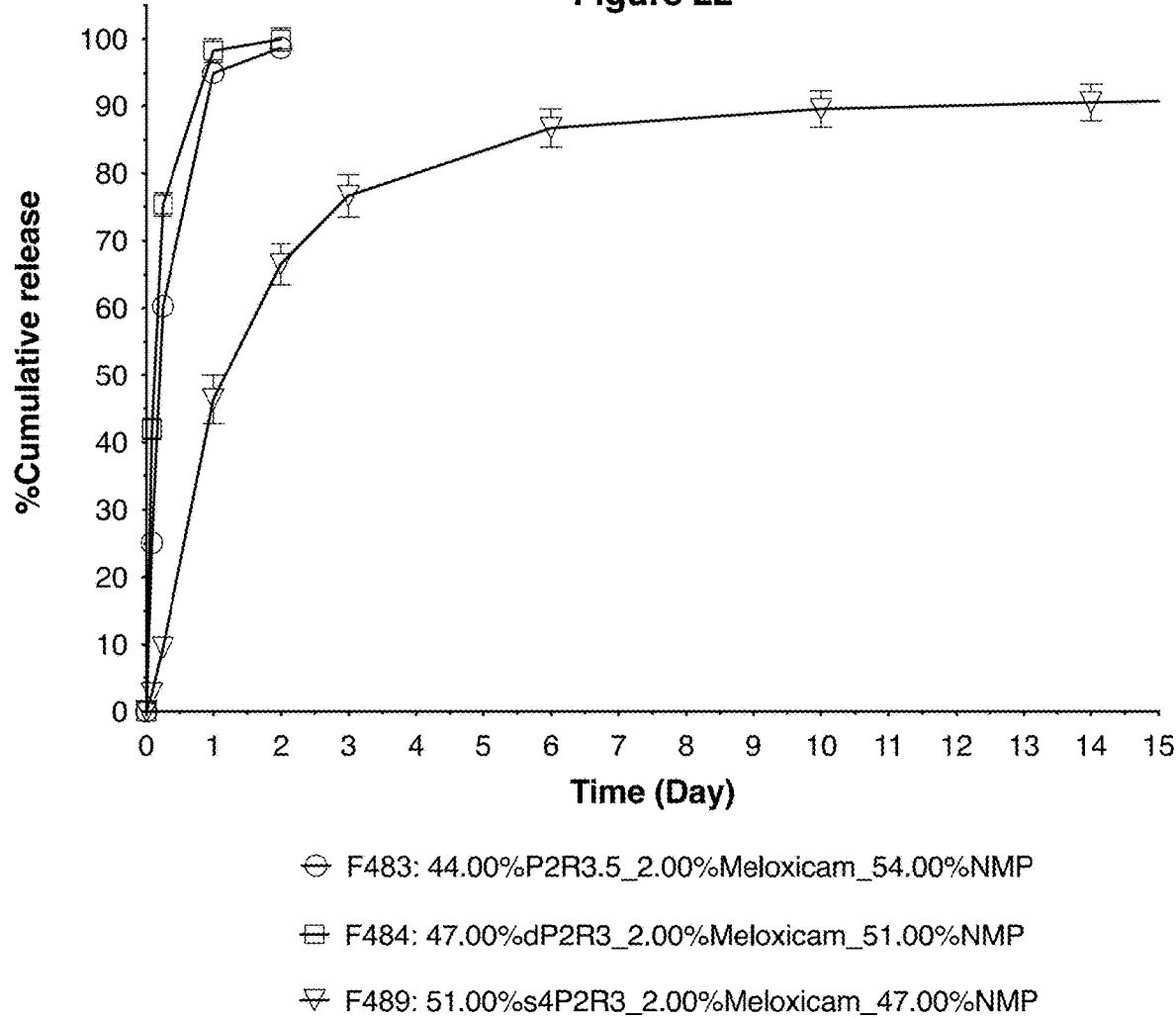

FIG. 22 shows the percentage in vitro cumulative release of meloxicam over time from three different formulations: Formulation F483 (○) containing 44.00% of P2R3.5 triblock copolymer with 2.00% active ingredient (API) and 54.00% of NMP; formulation F484 (□) containing 47.00% of dP2R3 diblock copolymer with 2.00% active ingredient (API) and 51.00% of NMP and formulation F489 (∇) containing 51.00% of s4-P2R3 star-shaped copolymer with 2.00% active ingredient (API) and 47.00% of NMP. In vitro release tests have been conducted according to set up 1 in table 2, example 3. The specific block copolymer formulations are set forth in Table 1.

Results indicate that the star-shaped copolymers-based formulation leads to a slower release kinetics compared to those of linear copolymer-based formulations with a comparable molecular weight. Indeed, formulation F489 shows slower release kinetics compared to F483 and F484.

Figure 23:
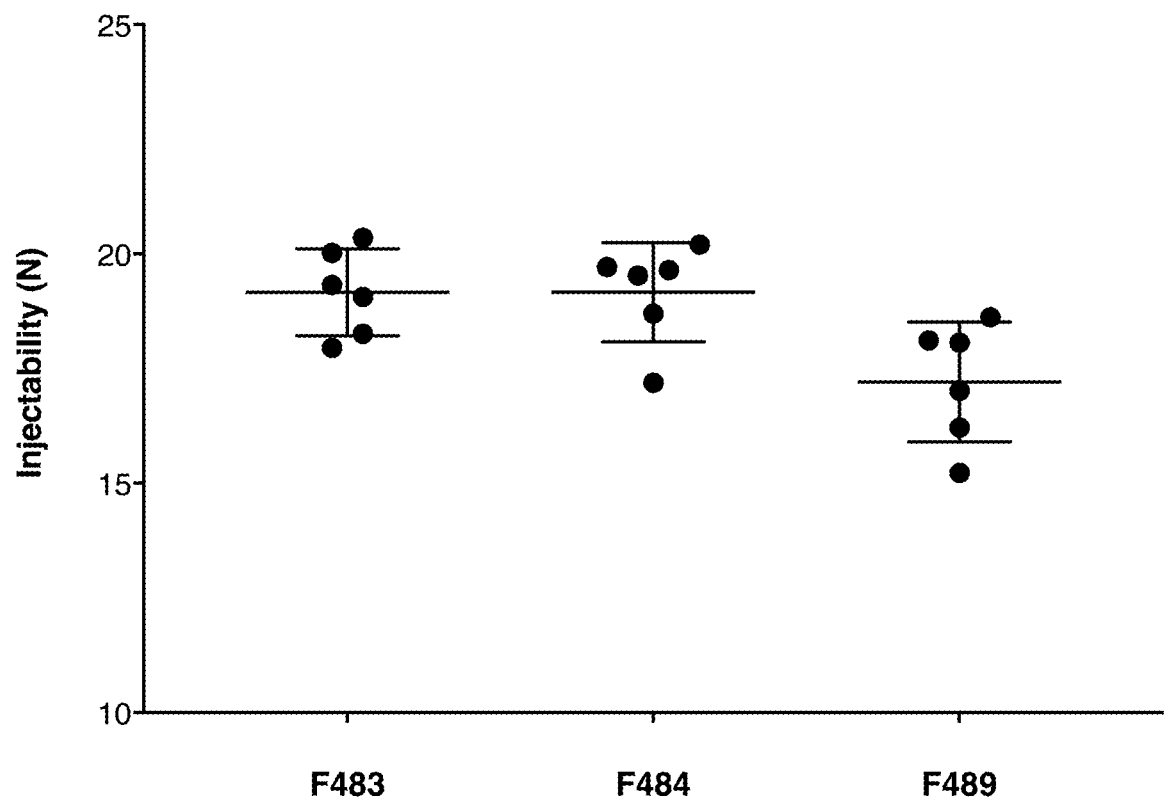

FIG. 23 presents injectability values of formulations F483, F484 and F489. Data demonstrate that for an identical injectability and comparable molecular weight, the star-shaped copolymer-based formulation shows slower release kinetics compared to those of linear copolymer-based formulations. Table 3 presents the details of injectability data.

Figure 24:
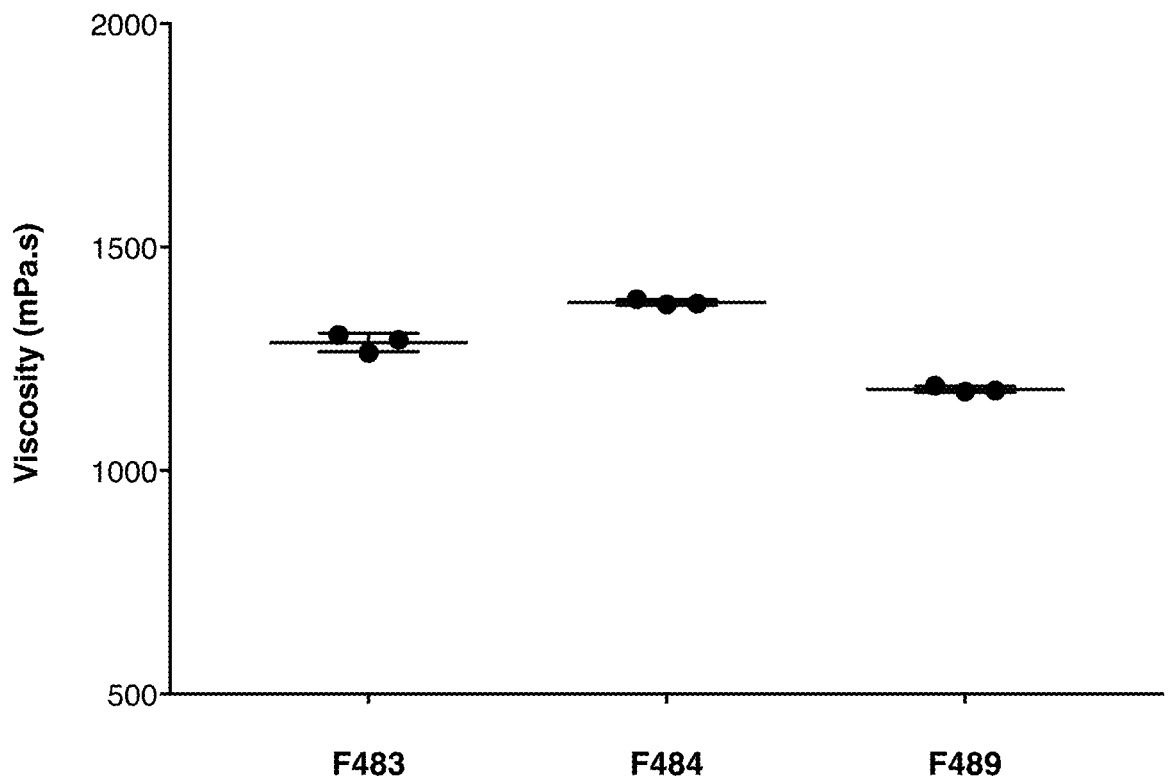

FIG. 24 presents viscosity values of F483, F484 and F489. Data demonstrate that for a similar viscosity and comparable molecular weight, the star-shaped copolymer-based formulation shows slower release kinetics compared to those of linear copolymer-based formulations. Table 4 presents the details of viscosity data.

Figure 25:
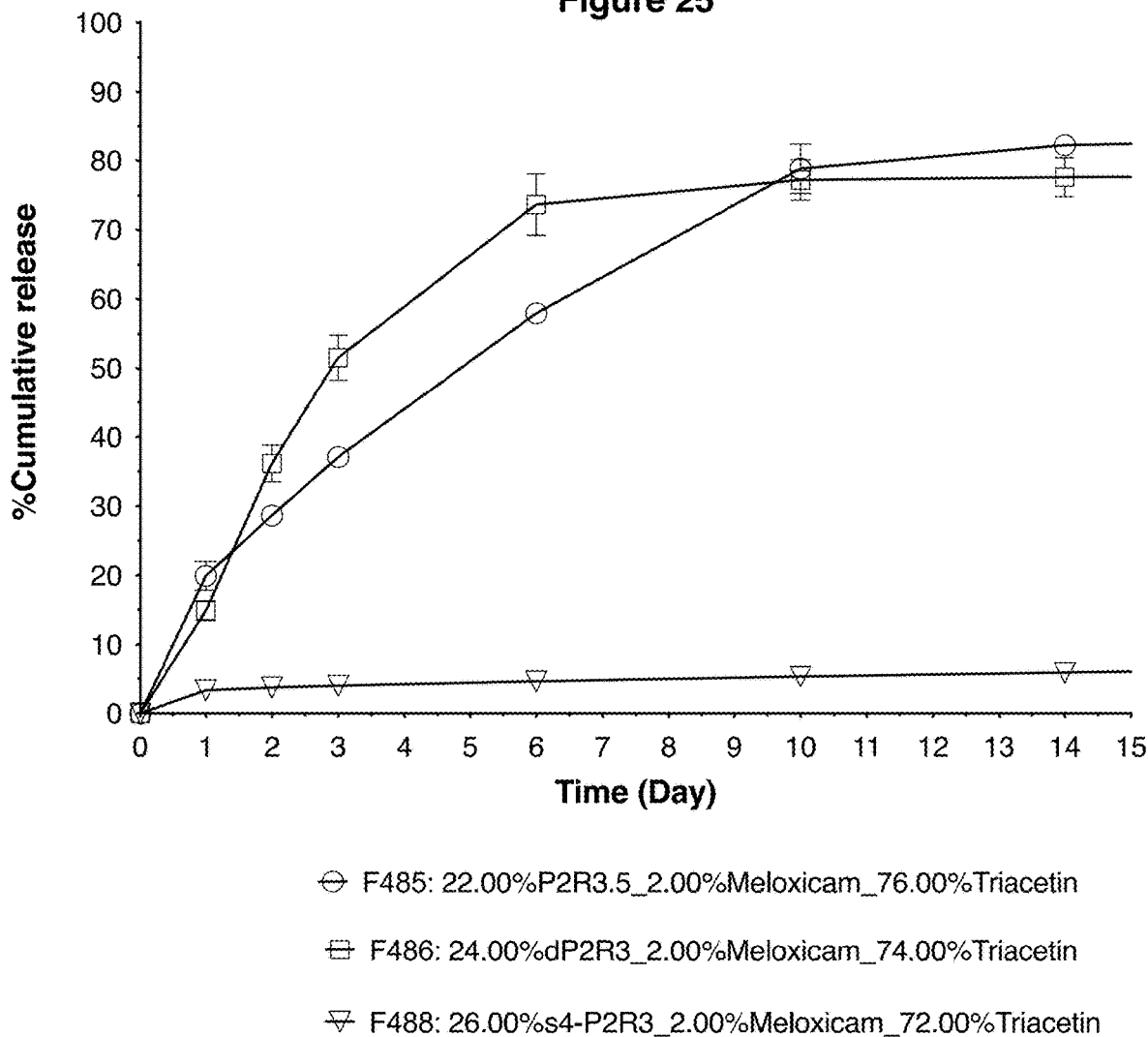

FIG. 25 is a graph showing the percentage in vitro cumulative release of meloxicam over time from three different formulation: Formulation F485 (○) containing 22.00% of P2R3.5 triblock copolymer with 2.00% active ingredient (API) and 76.00% of triacetin; formulation F486 (□) containing 24.00% of dP2R3 diblock copolymer with 2.00% active ingredient (API) and 74.00% of triacetin and formulation F488 (∇) containing 26.00% of s4-P2R3 star-shaped copolymer with 2.00% active ingredient (API) and 72.00% of triacetin. In vitro release tests have been conducted according to set up 1 in table 2, example 3. The specific block copolymer formulations are set forth in Table 1.

Results indicate that the star-shaped copolymer-based formulation leads to slower release kinetics compared of those of linear copolymer-based formulations with a comparable molecular weight. Formulation F488 shows slower release kinetics than F485 and F486.

Figure 26:
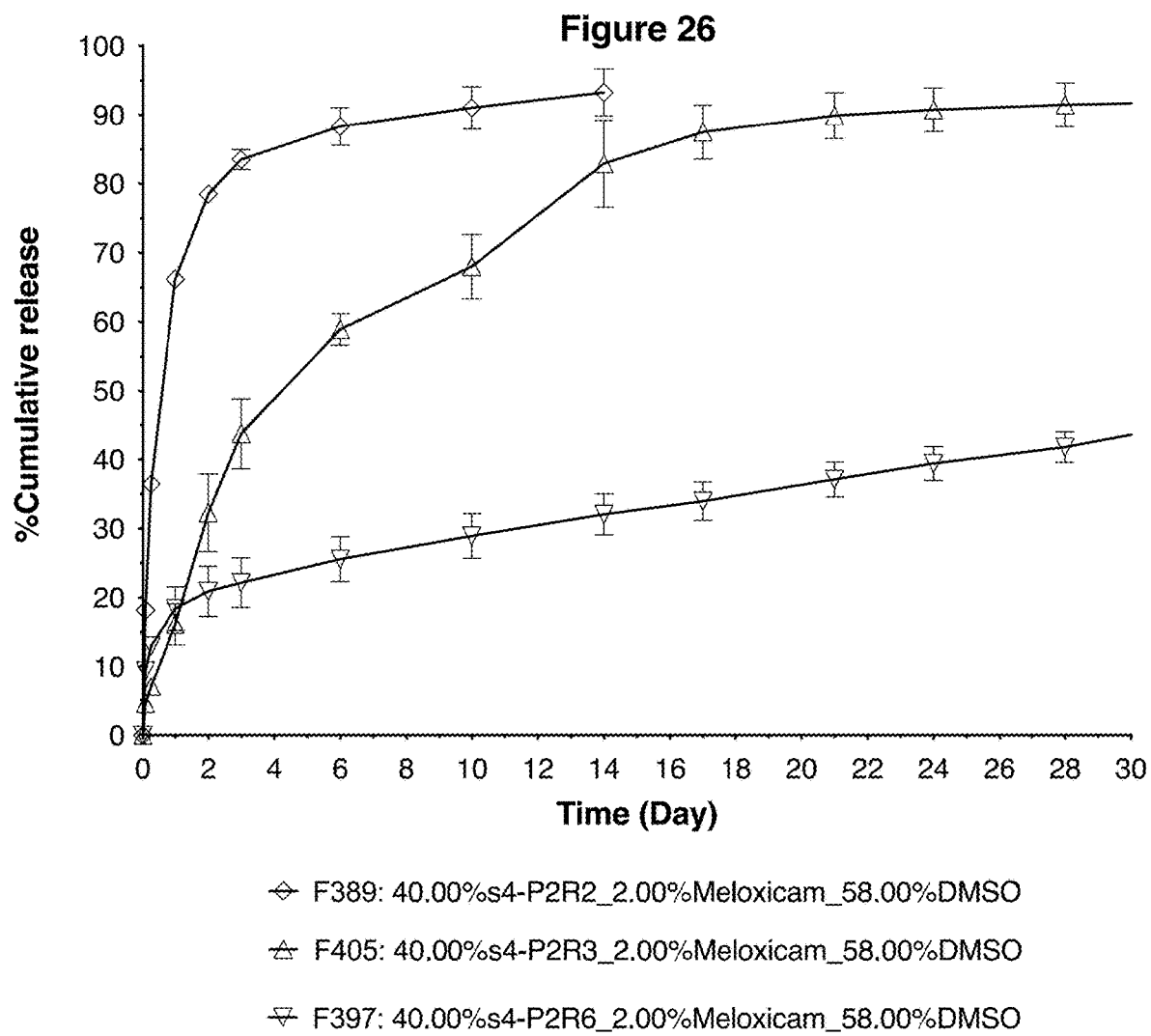

FIG. 26 shows the percentage total in vitro cumulative release of meloxicam over time from three different formulations. Formulation F389 (◊) containing 40.00% of s4-P2R2 star-shaped copolymer with 2.00% active ingredient (API) and 58.00% of DMSO; formulation F405 (4) containing 40.00% of s4-P2R3 star-shaped copolymer with 2.00% active ingredient (API) and 58.00% of DMSO and formulation F397 (∇) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1.

Data show that an increase of the PLA chain length within the star-shaped copolymer leads to a modulation of release kinetics in formulations with the same copolymer content. Formulation F397 shows slower release kinetics than F405 and F389. Similarly, formulation F405 shows slower release kinetics than F389.

Figure 27:
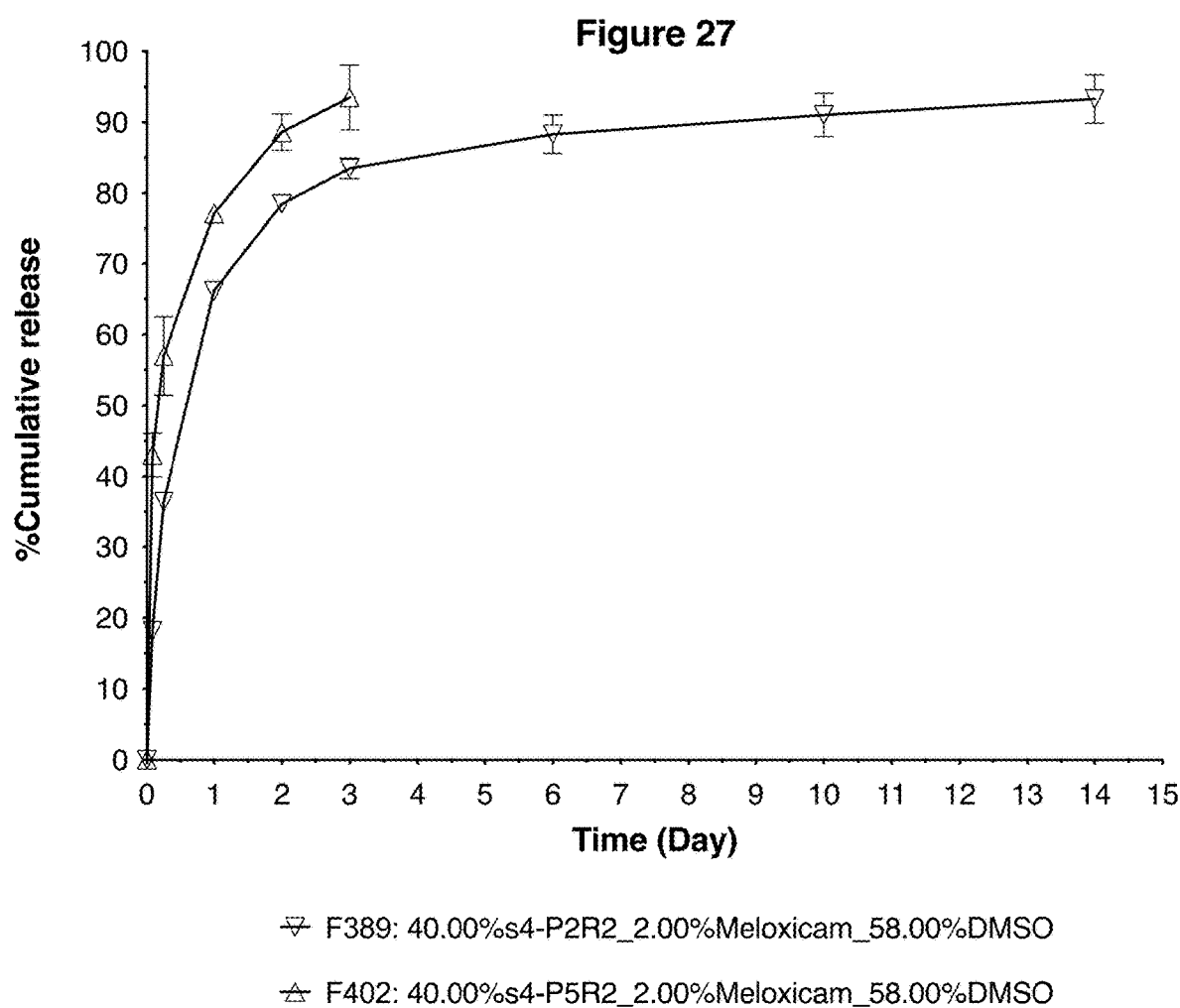

FIG. 27 displays the percentage in vitro cumulative release of meloxicam over time from two different formulations: formulation F389 (∇) containing 40.00% of s4-P2R2 star-shaped copolymer with 2.00% active ingredient (API) and 58.00% of DMSO and formulation F402 (Δ) containing 40.00% of s4-P5R2 star-shaped copolymer with 2.00% active ingredient (API) and 58.00% of DMSO. In vitro release tests have been conducted according to set up 1 in table 2, example 3. The specific block copolymer formulations are set forth in Table 1 below.

Data show that the increase of the PEG chain length within the star-shaped copolymer with a fixed LA/EO ratio leads to an increase of the release rate for formulations with the same copolymer content. Formulation F389 shows slower release kinetics compared to F402.

Figure 28:
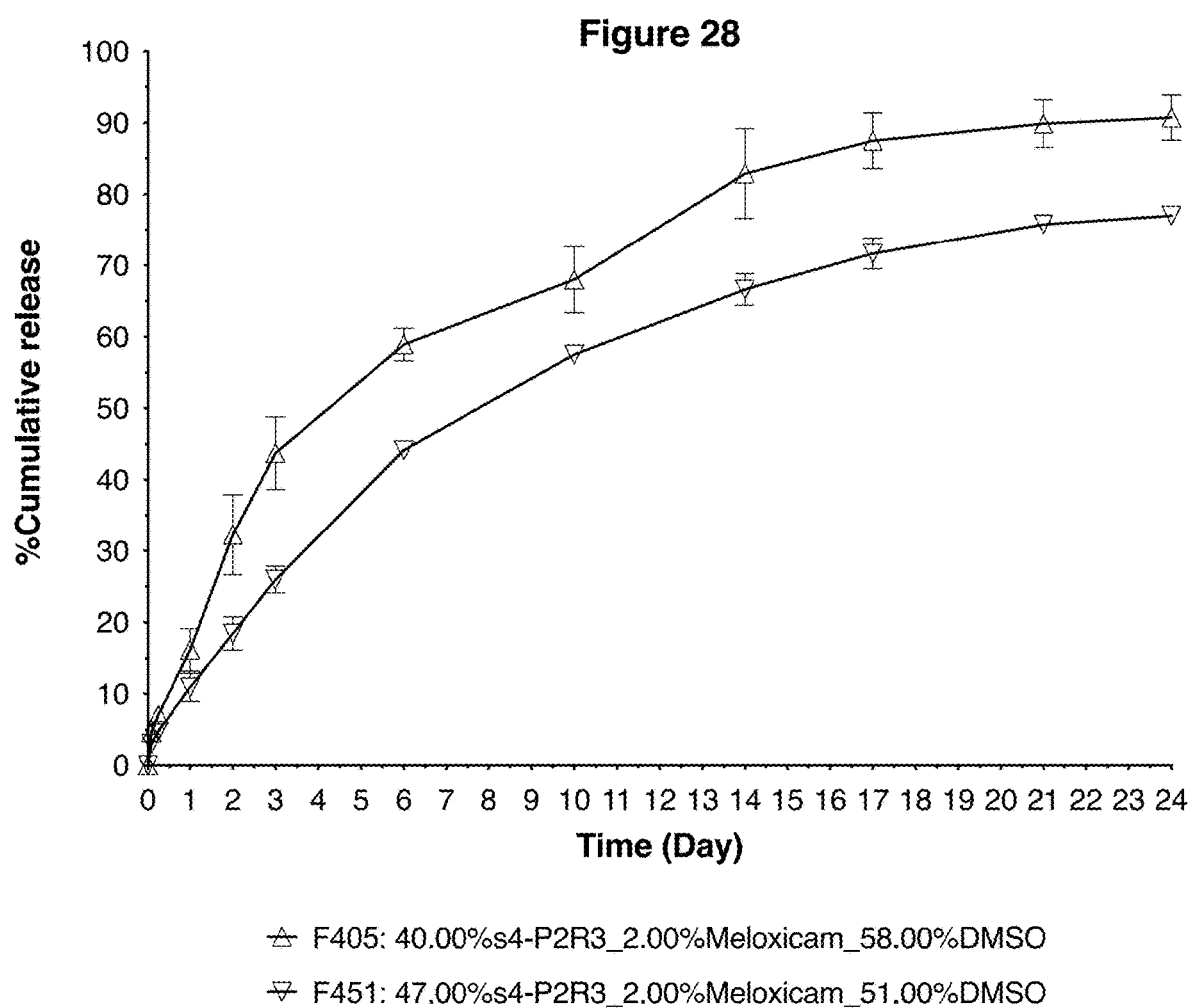

FIG. 28 presents the percentage in vitro cumulative release of meloxicam over time from two different formulations. Formulation F405 (Δ) containing 40.00% of s4-P2R3 star-shaped copolymer with 2.00% active ingredient (API) and 58.00% of DMSO and formulation F451 (∇) containing 47.00% of s4-P2R3 star-shaped copolymer with 2.00% active ingredient (API) and 51.00% of DMSO. In vitro release tests have been conducted according to set up 1 in table 2, example 3. The specific block copolymer formulations are set forth in Table 1 below.

Data show that an increase of the star-shaped copolymer content leads to a decrease of the release rate. Indeed, formulation F451 shows slower release kinetics compared to F405.

Figure 29:
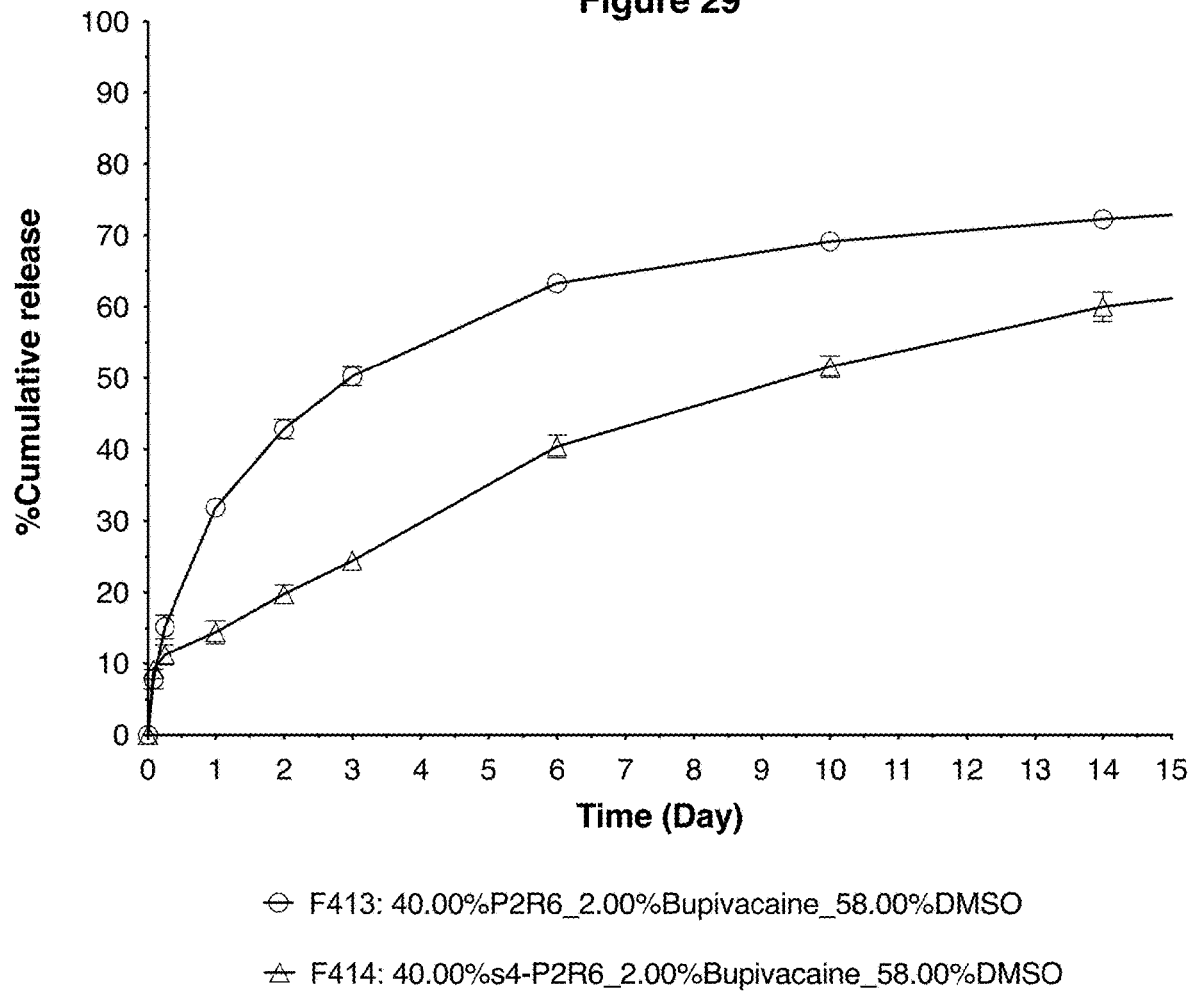

FIG. 29 presents the percentage in vitro cumulative release of bupivacaine over time from two different formulations: Formulation F413 (○) containing 40.00% of P2R6 triblock copolymer with 2.00% active ingredient (API) and 58.00% of DMSO and formulation F414 (Δ) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1 below.

Results indicate that the star-shaped copolymer-based formulation exhibits slower release kinetics compared to that of linear copolymer-based formulations having a comparable molecular weight. Indeed, formulation F414 shows slower release kinetics compared to formulation F413.

Figure 30:
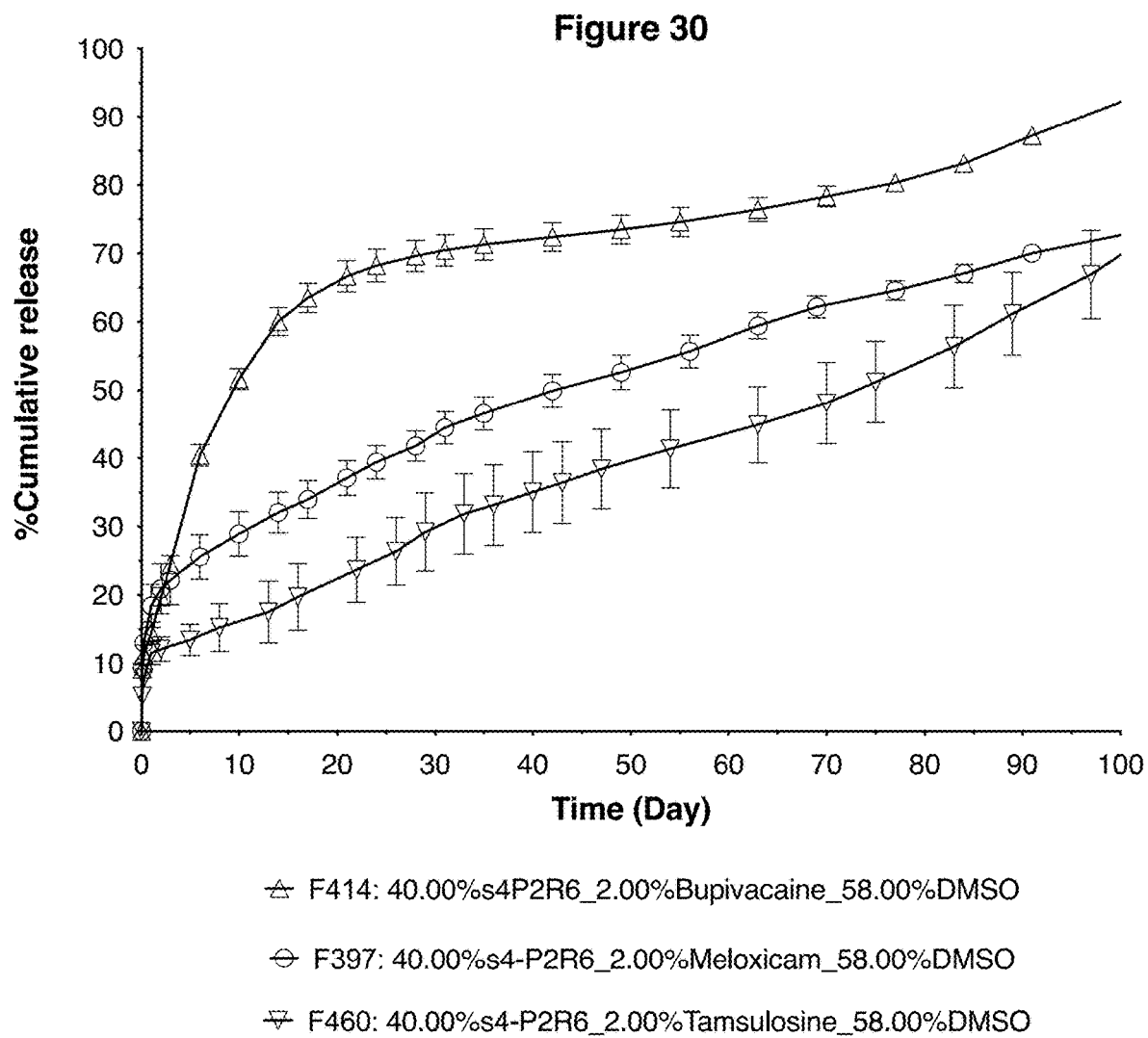

FIG. 30 shows the percentage in vitro cumulative release of meloxicam, bupivacaine and tamsulosin over time from three different formulations: formulation F414 (Δ) containing 40.00% of s4-P2R6 star-shaped copolymer with 2.00% bupivacaine and 58.00% of DMSO; formulation F397 (○) containing 40.00% of s4-P2R6 star-shaped copolymer with 2.00% meloxicam and 58.00% of DMSO and formulation F460 (∇) containing 40.00% of s4-P2R6 star-shaped copolymer with 2.00% tamsulosin and 58.00% of DMSO. In vitro release tests have been conducted according to set up 1 in table 2, example 3. The specific block copolymer formulations are set forth in Table 1 below.

Data show that it is possible to achieve a long-term sustained release of different APIs using the star-shaped copolymer-based formulations described in the present invention.

Figure 31:
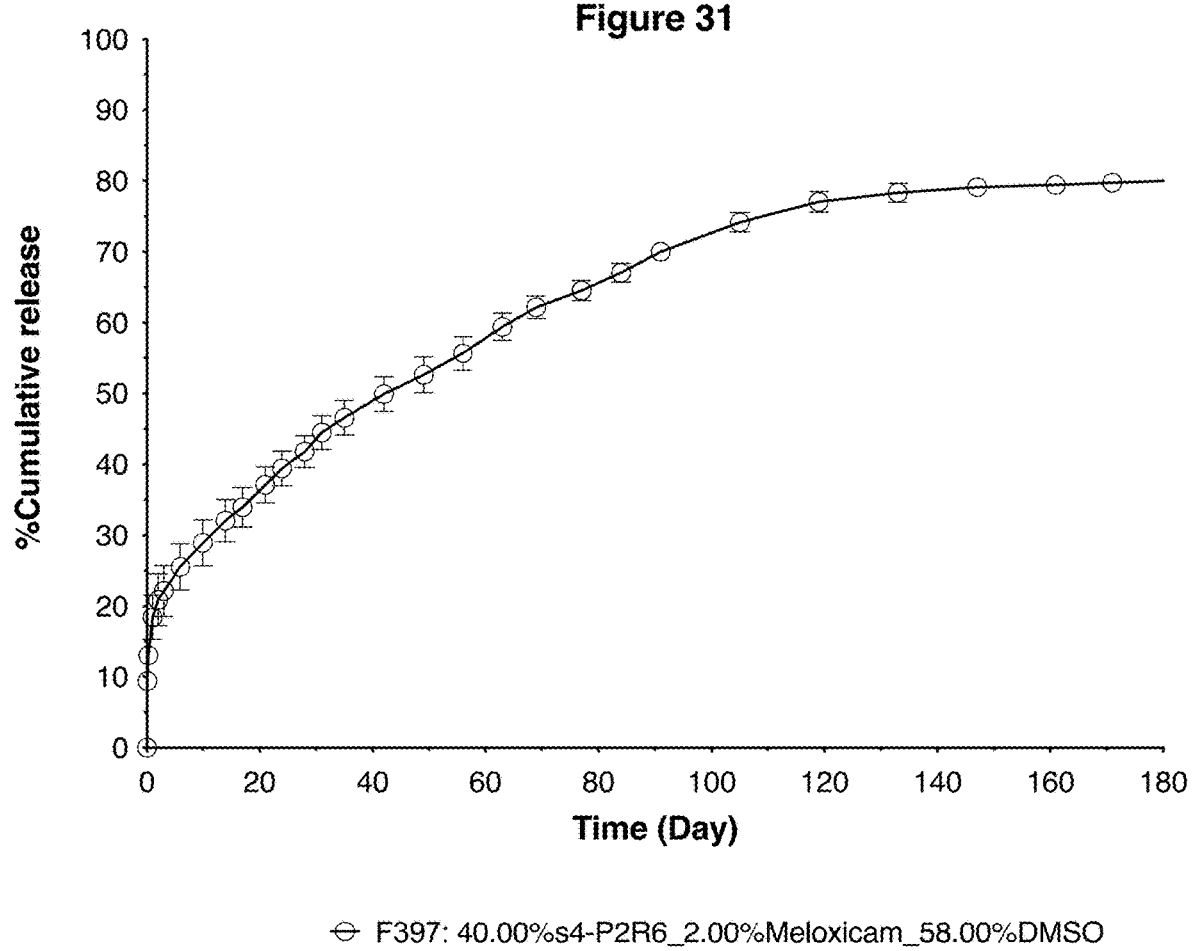

FIG. 31 is a graph showing the percentage total in vitro cumulative release of meloxicam over time from F397. Formulation F397 (○) contains 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1 below.

Results demonstrate that star-shaped copolymer-based formulation leads to a sustained release of the drug up to at least 6 months.

Figure 32:
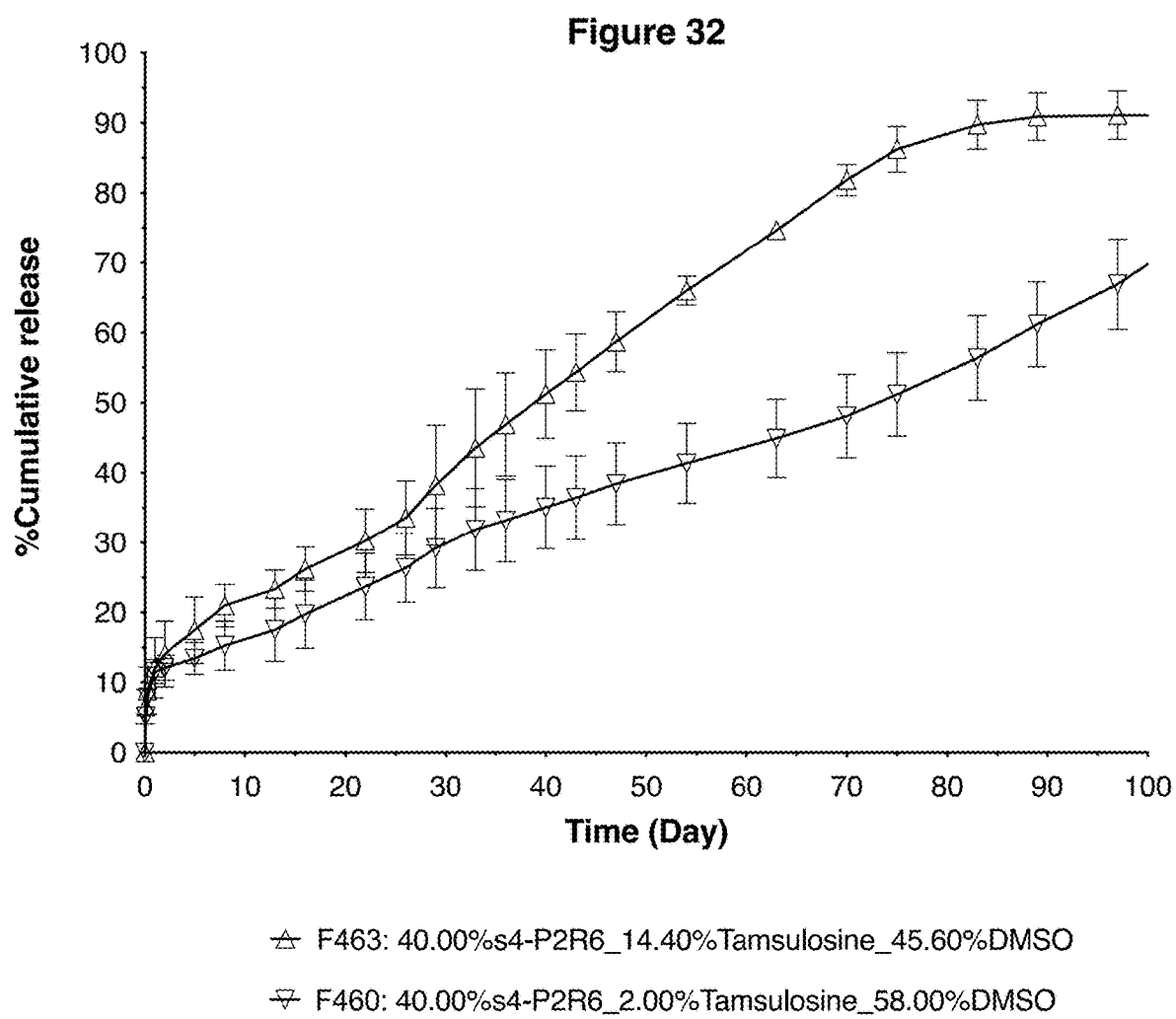

FIG. 32 shows the percentage in vitro cumulative release of tamsulosin over time from two different formulations: Formulation F463 (Δ) containing 40.00% of s4-P2R6 star-shaped copolymer with 14.40% active ingredient (API) and 45.60% of DMSO and formulation F460 (∇) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1 below.

Results demonstrate that the star-shaped copolymer-based formulations allow sustained release with two different API loadings.

Figure 33:
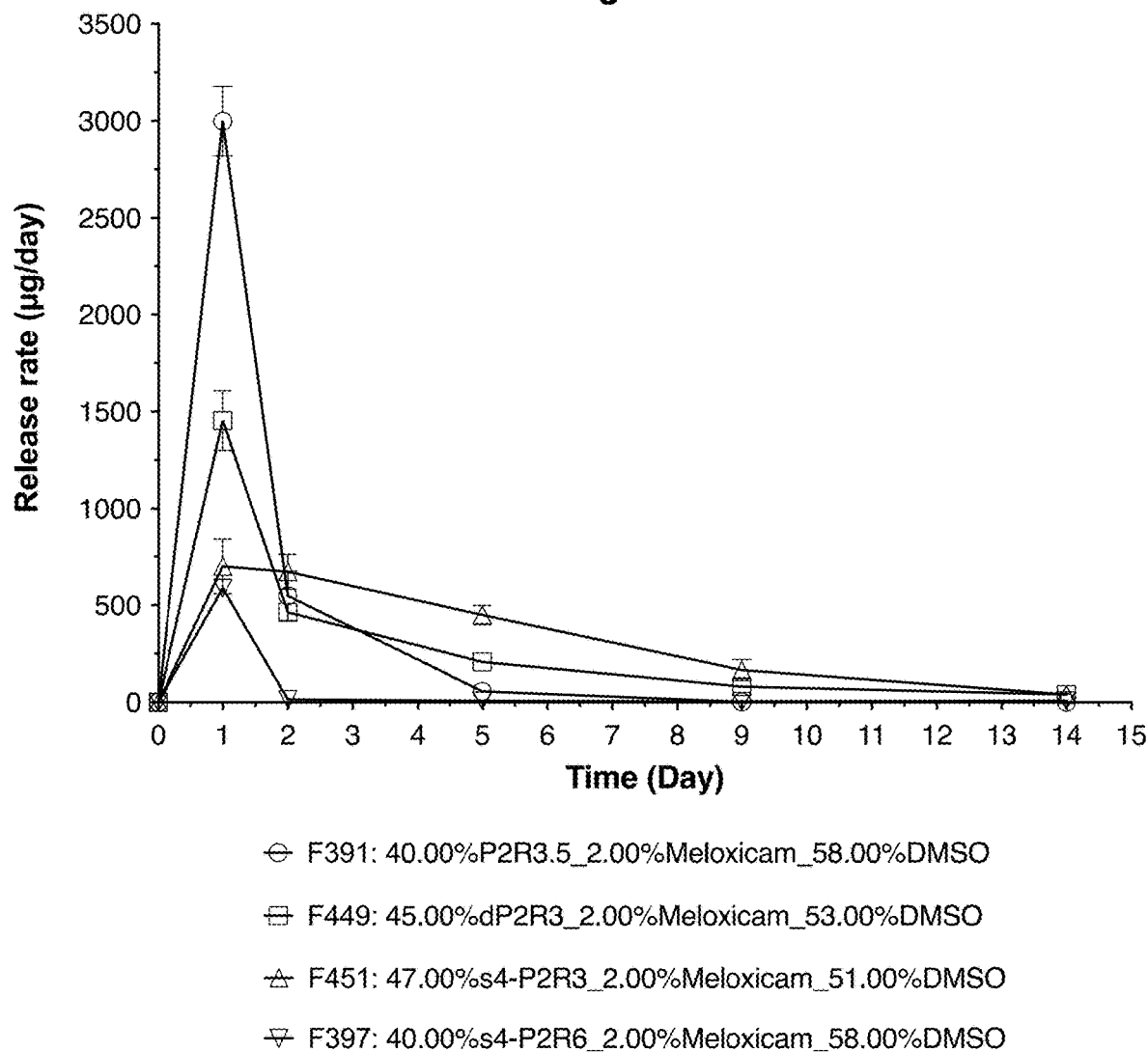

FIG. 33 shows the release rate on micrograms per day of meloxicam over time from four different formulations: Formulation F391 (○) containing 40.00% of P2R3.5 triblock copolymer with 2.00% active ingredient (API) and 58.00% of DMSO; formulation F449 (□) containing 45.00% of dP2R3 diblock copolymer with 2.00% active ingredient (API) and 53.00% of DMSO; formulation F451 (Δ) containing 47.00% of s4-P2R3 star-shaped copolymer with 2.00% active ingredient (API) and 51.00% of DMSO and formulation F397 (∇) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1.

Results indicate that the star-shaped copolymer-based formulations lead to slower release kinetics compared to those of linear copolymer-based formulation having a comparable molecular weight. Indeed, formulations F451 and F397 show slower release kinetics compared to F391 and F449.

It can be seen that star-shaped based formulation F397 leads to the slowest release rate.

Figure 34:
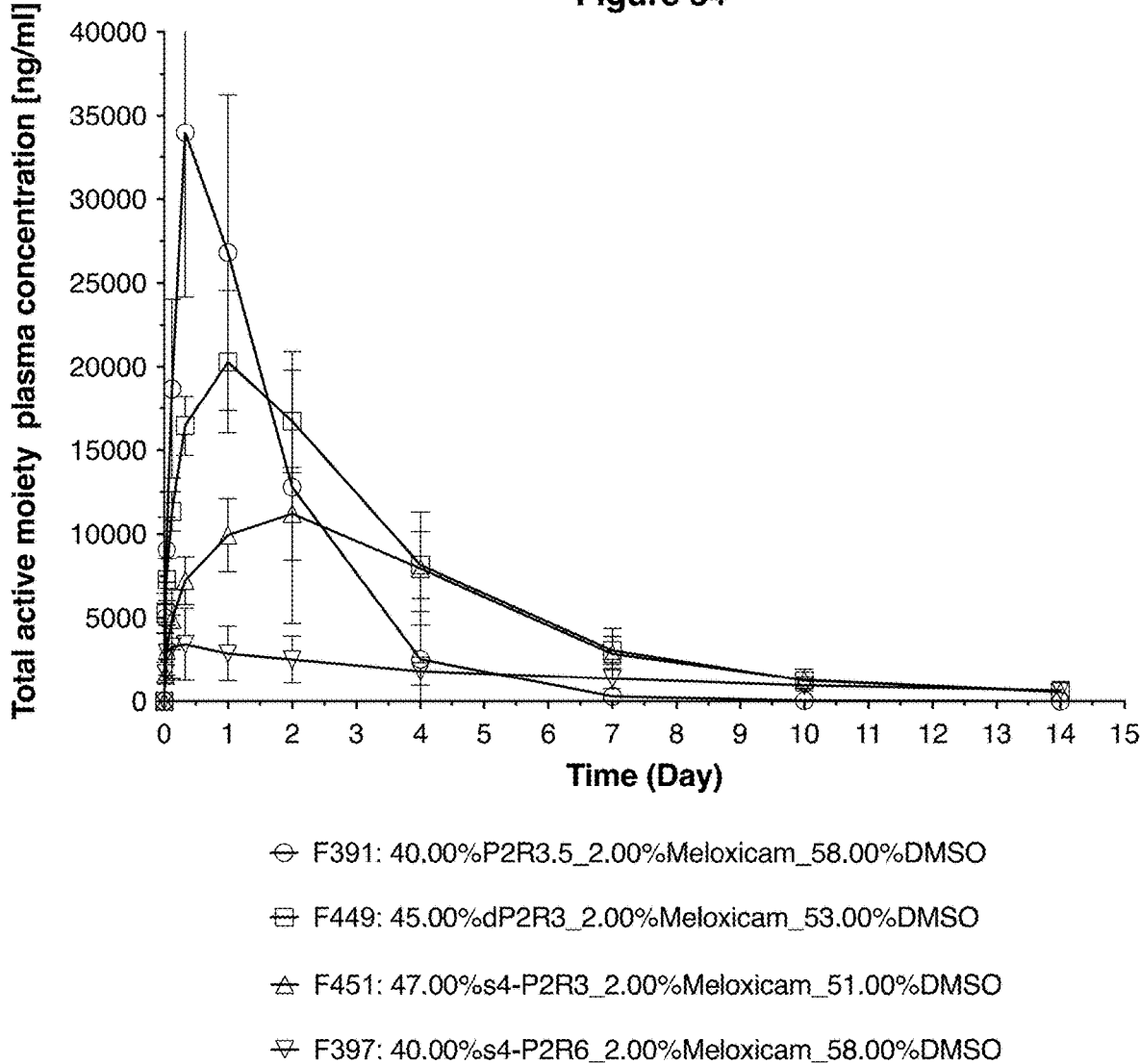

FIG. 34 is a graph showing the total active moiety plasma concentration expressed in nanogram per milliliter of meloxicam over time from the four different formulations displayed in FIG. 33. In vivo release tests have been conducted according to set up 1 in table 5, example 7.

Results indicate that, accordingly to the observations in vitro, the star-shaped copolymer based-formulations exhibit slower release kinetics in vivo compared to those of a linear copolymer-based formulation with a comparable molecular weight. Indeed, formulations F451 and F397 show slower release kinetics compared to F391 and F449.

Similarly to the in vitro results, it was observed that star-shaped based formulation F397 leads to the slowest release rate.

Figure 35:
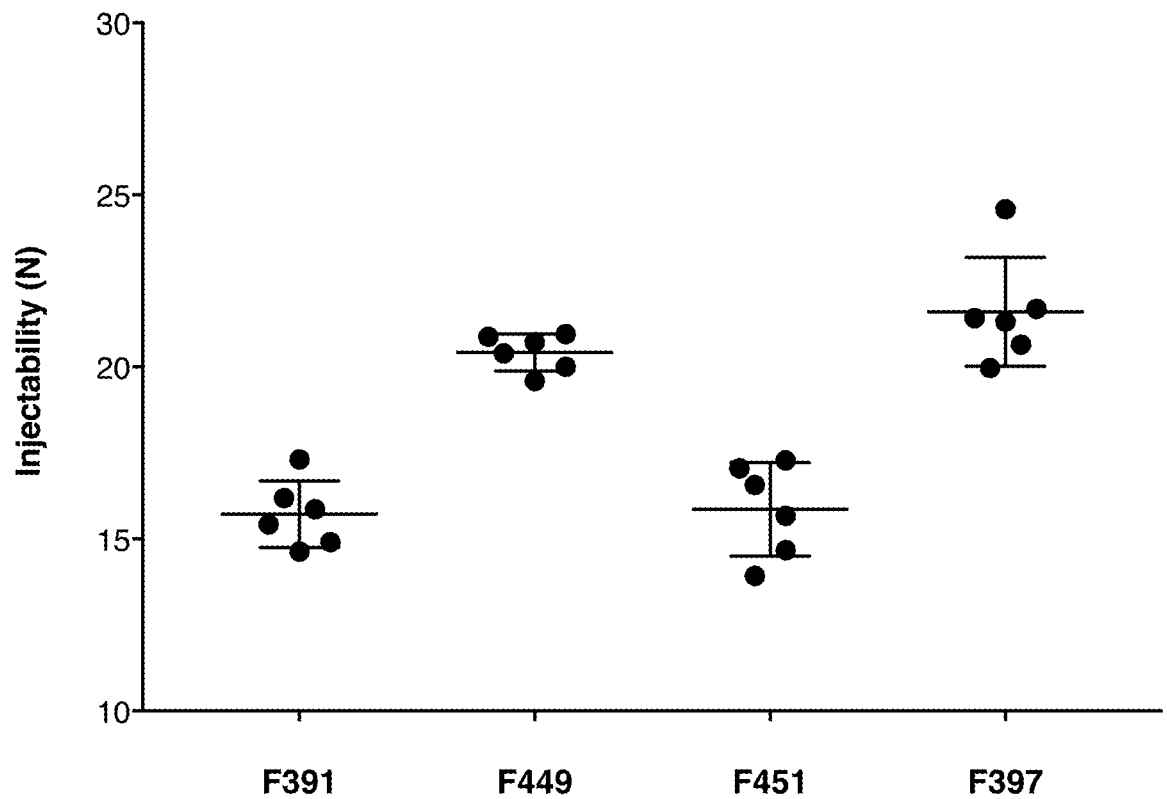

FIG. 35 presents injectability values of formulations F391, F449, F451 and F397. Data demonstrate that for a similar injectability (ca. 20N), star-shaped copolymer-based formulations show slower release kinetics compared to those of linear copolymer-based formulations. Table 3 presents the details of injectability data.

Figure 36:
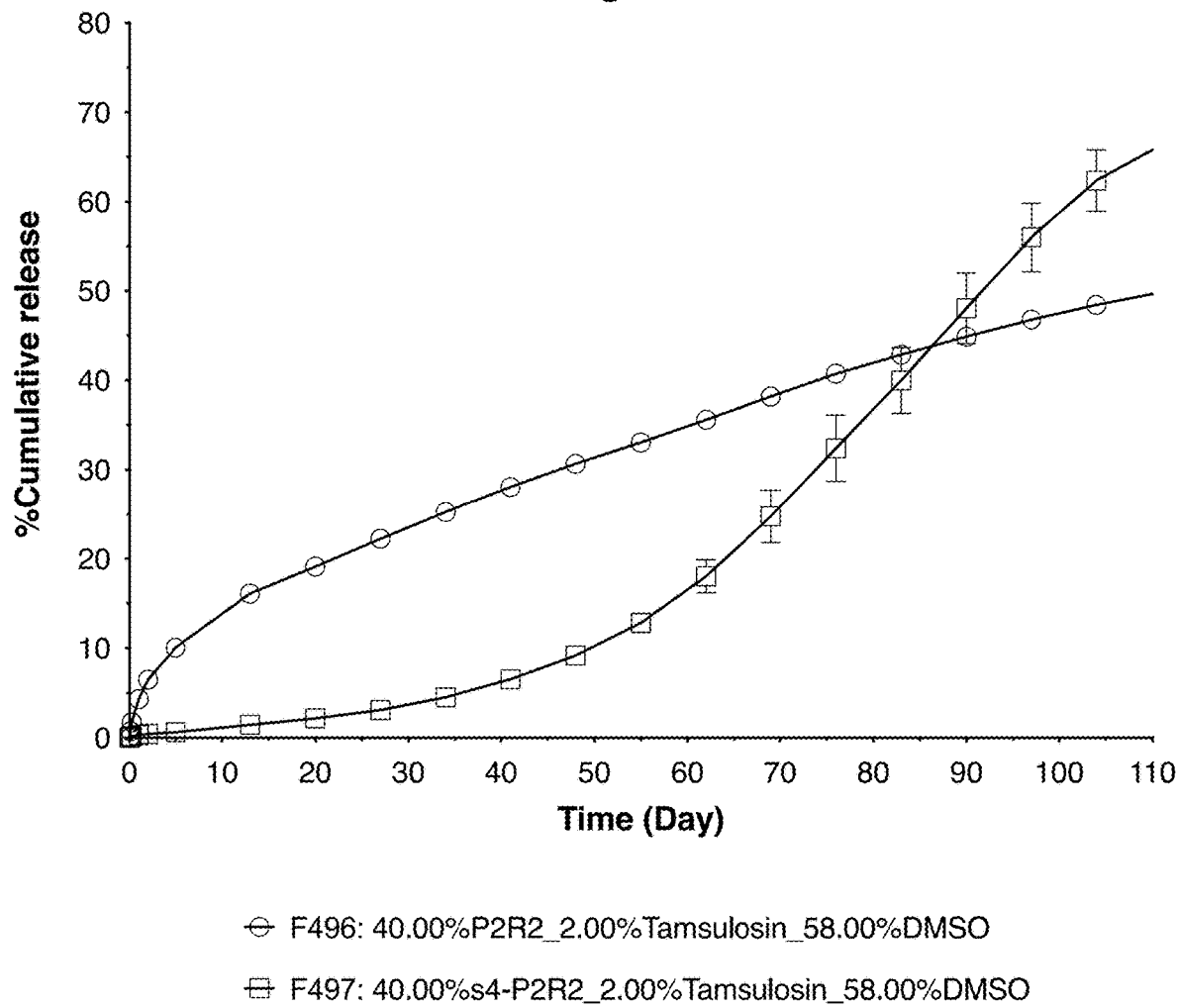

FIG. 36 displays the percentage in vitro cumulative release of lactic acid over time from two different formulations, as a measure of PEG-PLA copolymer degradation. Formulation F496 (○) containing 40.00% of P2R2 triblock copolymer with 2.00% tamsulosin and 58.00% of DMSO and formulation F497 (□) containing 40.00% of s4-P2R2 star-shaped copolymer with 2.00% tamsulosin and 58.00% of DMSO. Lactic acid quantification has been conducted according to example 4. The specific block copolymer formulations are set forth in Table 1 below.

Data shows that linear copolymer-based formulation F496 leads to a constant lactic acid release over the time period. F497 star-shaped copolymer-based formulation leads to slower release kinetics of lactic acid than F496 for the 50 first days and then the release accelerates until the end of the studied period.

Thus, surprisingly the star-shaped copolymer-based formulation leads to an accelerated depot degradation compared to the linear copolymer-based formulation.

Figure 37:
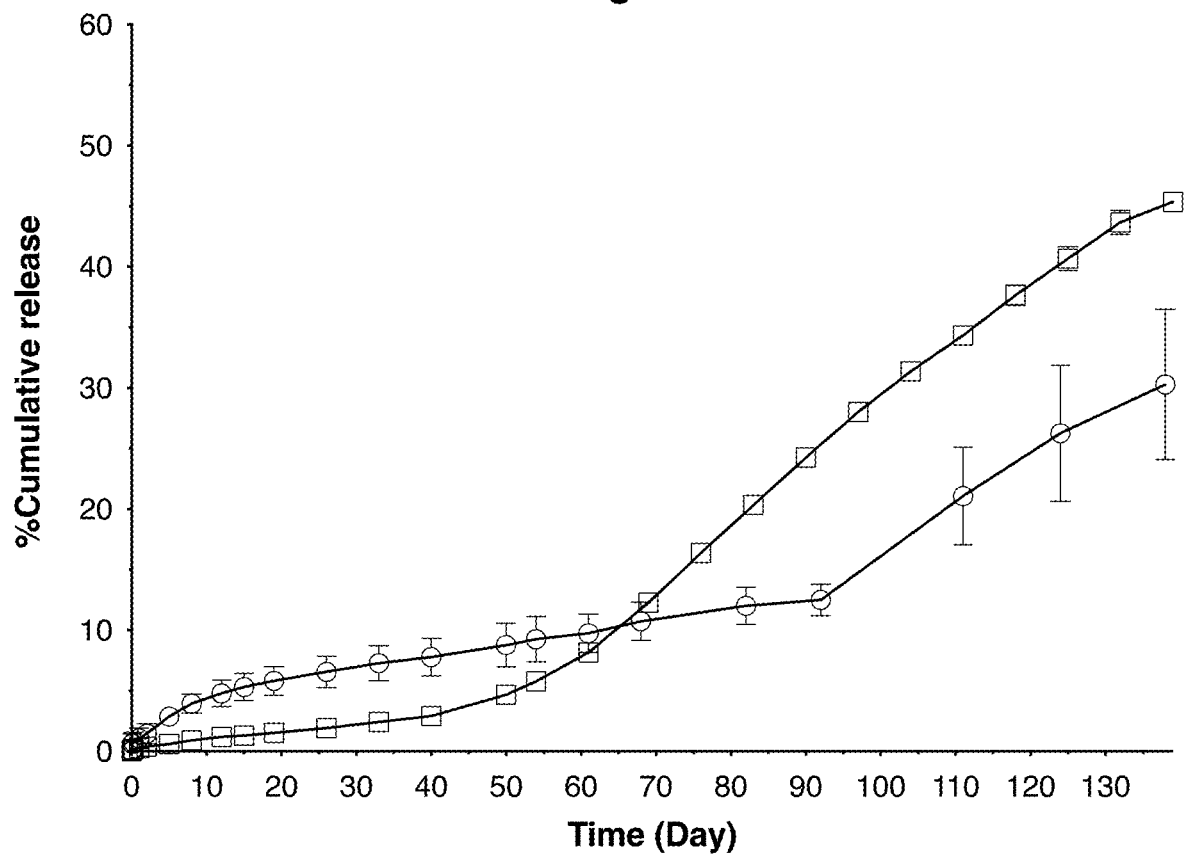

FIG. 37 is a graph showing the percentage total in vitro cumulative release of lactic acid over time from two different formulations: Formulation F498 (○) containing 40.00% of dP2R3 diblock copolymer with 2.00% tamsulosin and 58.00% of DMSO and formulation F499 (□) containing 40.00% of s4-P2R3 star-shaped copolymer with 2.00% tamsulosin and 58.00% of DMSO. Lactic acid quantification has been conducted according to example 4. The specific block copolymer formulations are set forth in Table 1 below.

Data show that linear copolymer-based formulation F498 leads to a slow, quasi-constant lactic acid release for the 90 first days and then the release accelerates until the end of the studied period. Star-shaped copolymer-based formulation F499 leads to slower release kinetics of lactic acid than F498 for the 50 first days and then release accelerates until the end of the studied period. Thus, depots of star-shaped copolymer-based formulations undergo an accelerated depot degradation compared to depots made of linear-copolymer based-formulations.

Figure 38:
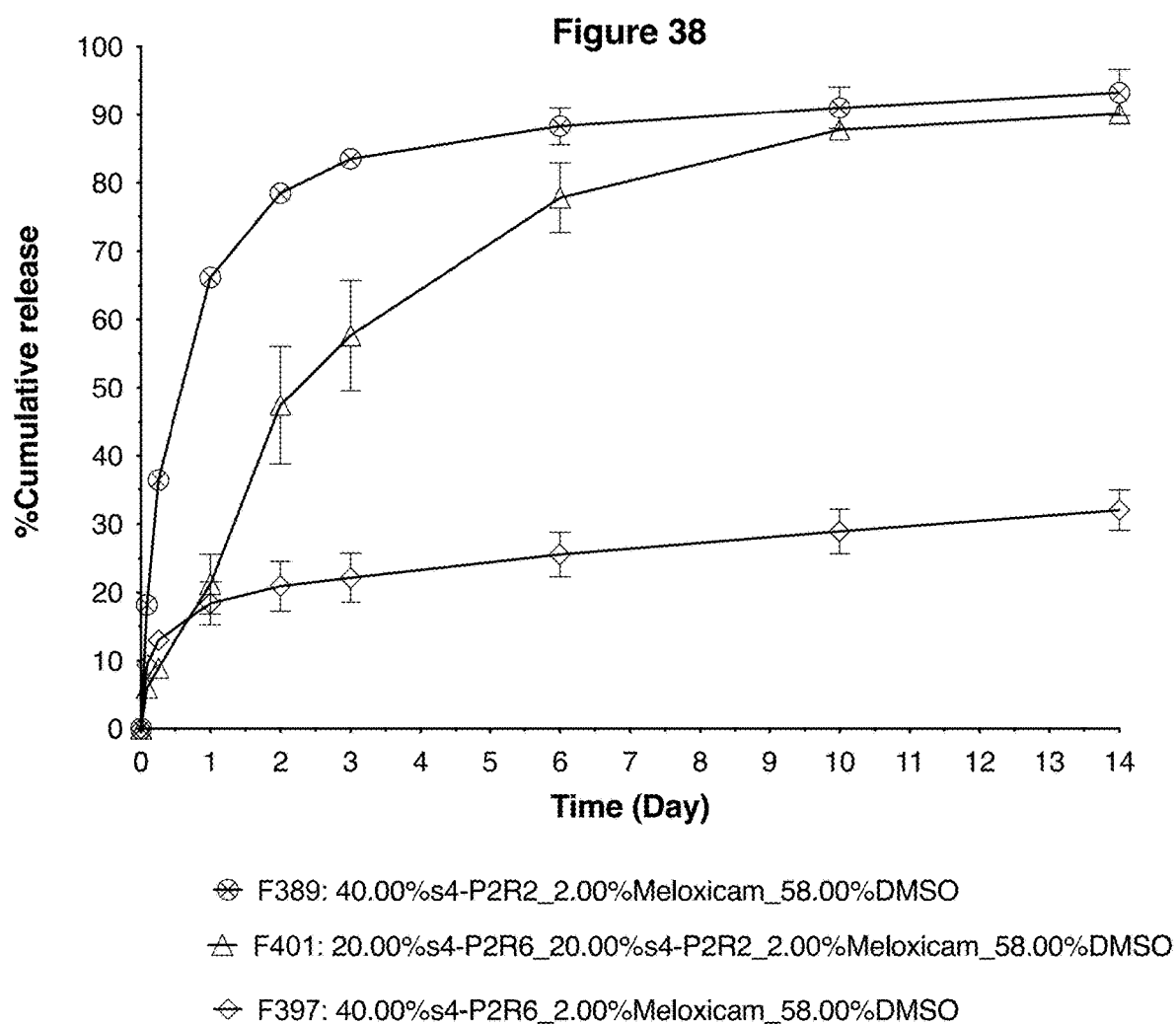

FIG. 38 shows the percentage in vitro cumulative release of meloxicam over time from three different formulations: Formulation F389 (⊗) containing 40.00% of s4-P2R2 star-shaped copolymer with 2.00% active ingredient (API) and 58.00% of DMSO, formulation F401 (Δ) containing 20.00% of s4-P2R6 star-shaped copolymer and 20.00% of s4-P2R2 star-shaped copolymer with 2.00% active ingredient (API) and 58.00% of DMSO and formulation F397 (◇) containing 40.00% of s4-P2R6 star-shaped copolymer with 2.00% active ingredient (API) and 58.00% of DMSO. In vitro release tests have been conducted according to set up 1 in table 2, example 3. The specific block copolymer formulations are set forth in Table 1 below.

Results demonstrate that the mixture of two star-shaped copolymers in a formulation composition lead to a modulated or improved release profile.

Figure 39:
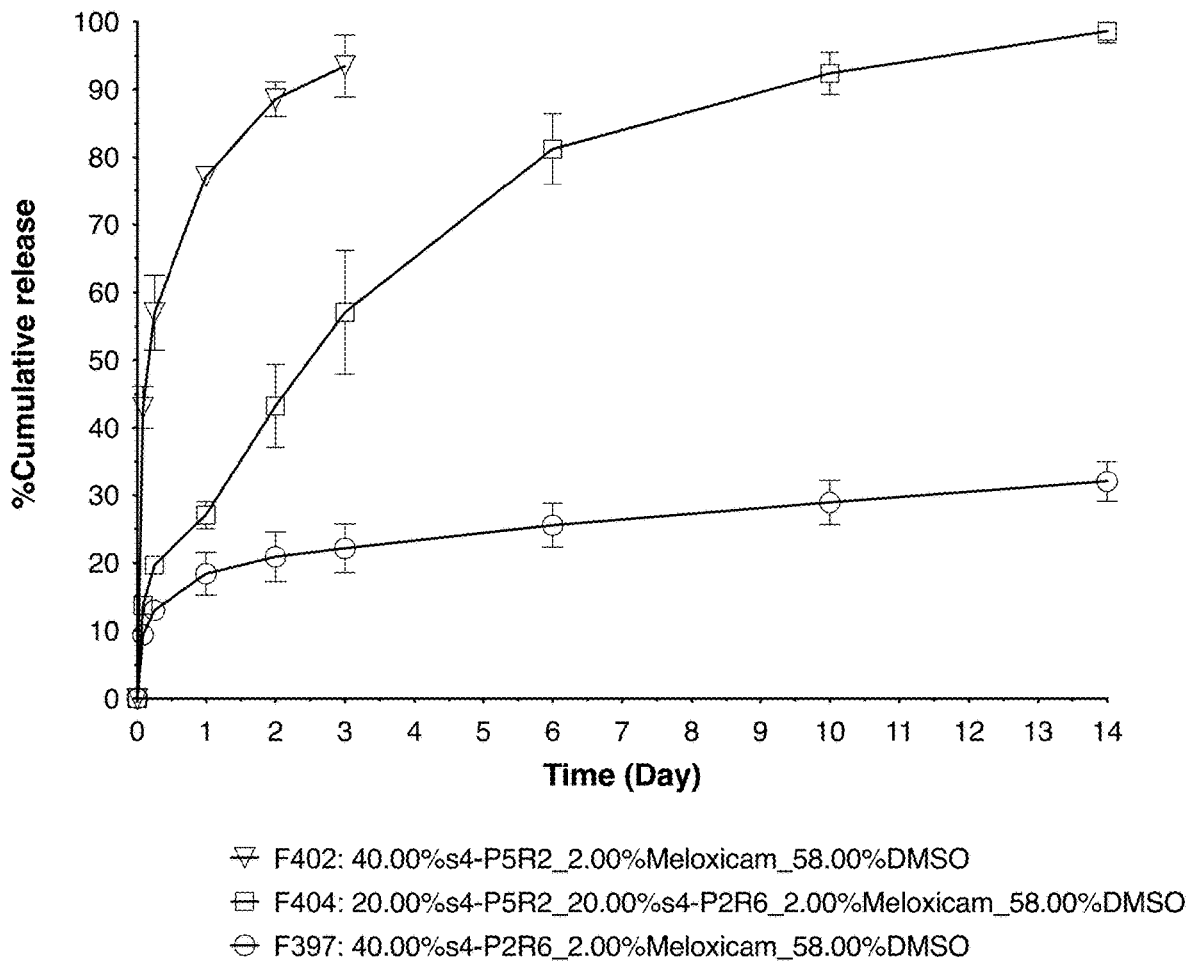

FIG. 39 shows the percentage in vitro cumulative release of meloxicam over time from three different formulations: formulation F397 (○) containing 40.00% of s4-P2R6 star-shaped copolymer with 2.00% active ingredient (API) and 58.00% of DMSO, formulation F402 (▽) containing 40.00% of s4-P5R2 star-shaped copolymer with 2.00% active ingredient (API) and 58.00% of DMSO and formulation F404 (□) containing 20.00% of s4-P2R6 star-shaped copolymer and 20.00% of s4-P5R2 star-shaped copolymer with 2.00% active ingredient (API) and 58.00% of DMSO. In vitro release tests have been conducted according to set up 1 in table 2, example 3. The specific block copolymer formulations are set forth in Table 1.

Results demonstrate that the mixture of two star-shaped copolymers in a formulation composition lead to a modulated release profile.

Figure 40:
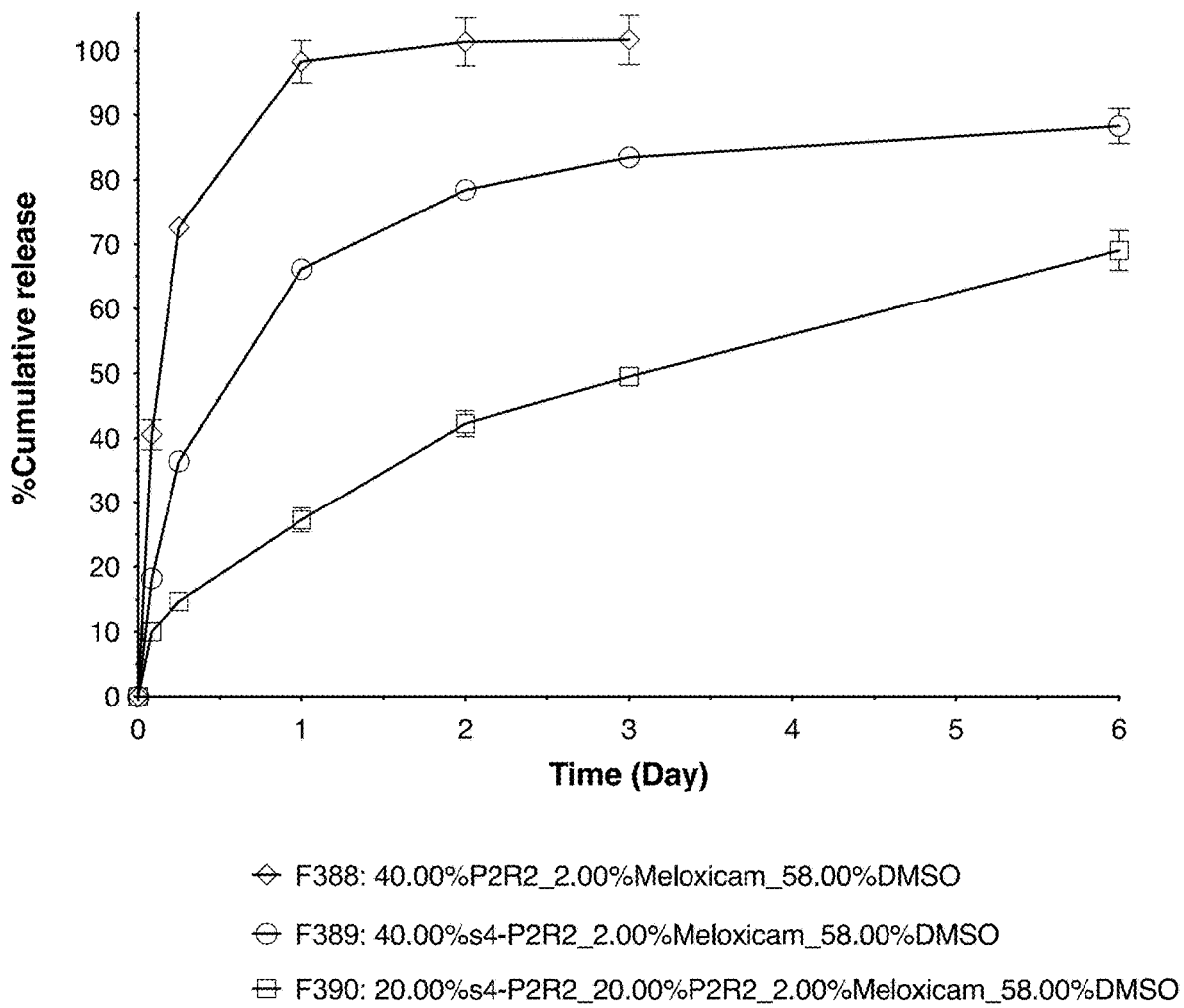

FIG. 40 shows the percentage in vitro cumulative release of meloxicam over time from three different formulations: Formulation F388 (◇) containing 40.00% of P2R2 linear copolymer with 2.00% active ingredient (API) and 58.00% of DMSO, formulation F389 (○) containing 40.00% of s4-P2R2 star-shaped copolymer with 2.00% active ingredient (API) and 58.00% of DMSO and formulation F390 (□) containing 20.00% of s4-P2R2 star-shaped copolymer and 20.00% of P2R2 linear copolymer with 2.00% active ingredient (API) and 58.00% of DMSO. In vitro release tests have been conducted according to set up 1 in table 2, example 3. The specific block copolymer formulations are set forth in Table 1 below.

Data shows that the mixture of linear and star-shaped copolymers in a formulation composition can lead to a modulated release profile. Surprisingly the mixed star-shaped and linear copolymer-based formulation leads to an optimized release profile compared to the star-shaped or the linear copolymer-based formulation.

Figure 41:
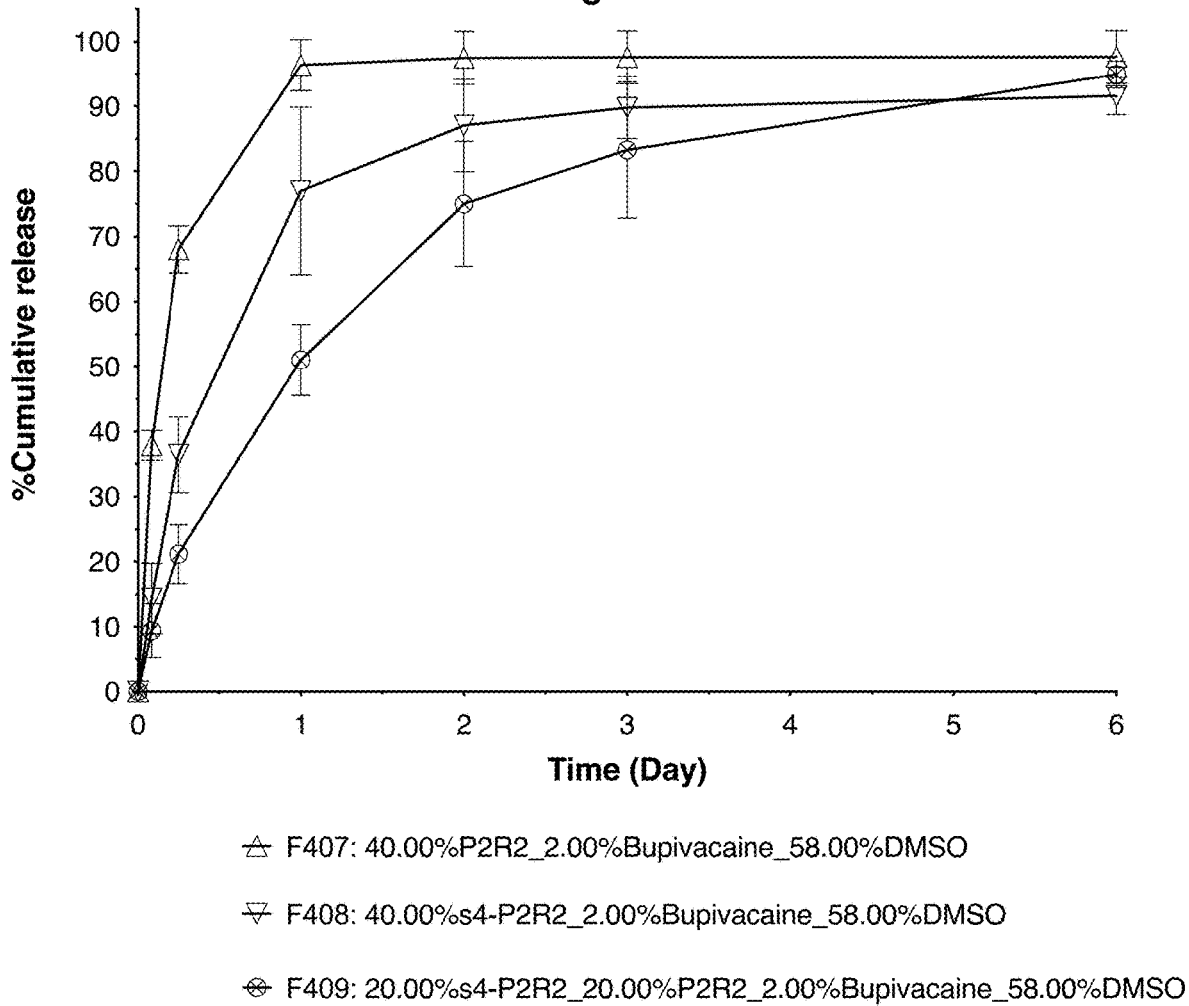

FIG. 41 shows the percentage in vitro cumulative release of bupivacaine over time from three different formulations: formulation F407 (Δ) containing 40.00% of P2R2 linear copolymer with 2.00% active ingredient (API) and 58.00% of DMSO, formulation F408 (▽) containing 40.00% of s4-P2R2 star-shaped copolymer with 2.00% active ingredient (API) and 58.00% of DMSO and formulation F409 (⊗) containing 20.00% of s4-P2R2 star-shaped copolymer and 20.00% of P2R2 linear copolymer with 2.00% active ingredient (API) and 58.00% of DMSO. In vitro release tests have been conducted according to set up 1 in table 2, example 3. The specific block copolymer formulations are set forth in Table 1 below.

Data shows that the mixture of linear and star-shaped copolymers in a formulation composition might lead to a modulated release profile. Thus, surprisingly the mixed star-shaped and linear copolymer-based formulation leads to an optimized release profile compared to the star-shaped or the linear copolymer-based formulation.

Figure 42:
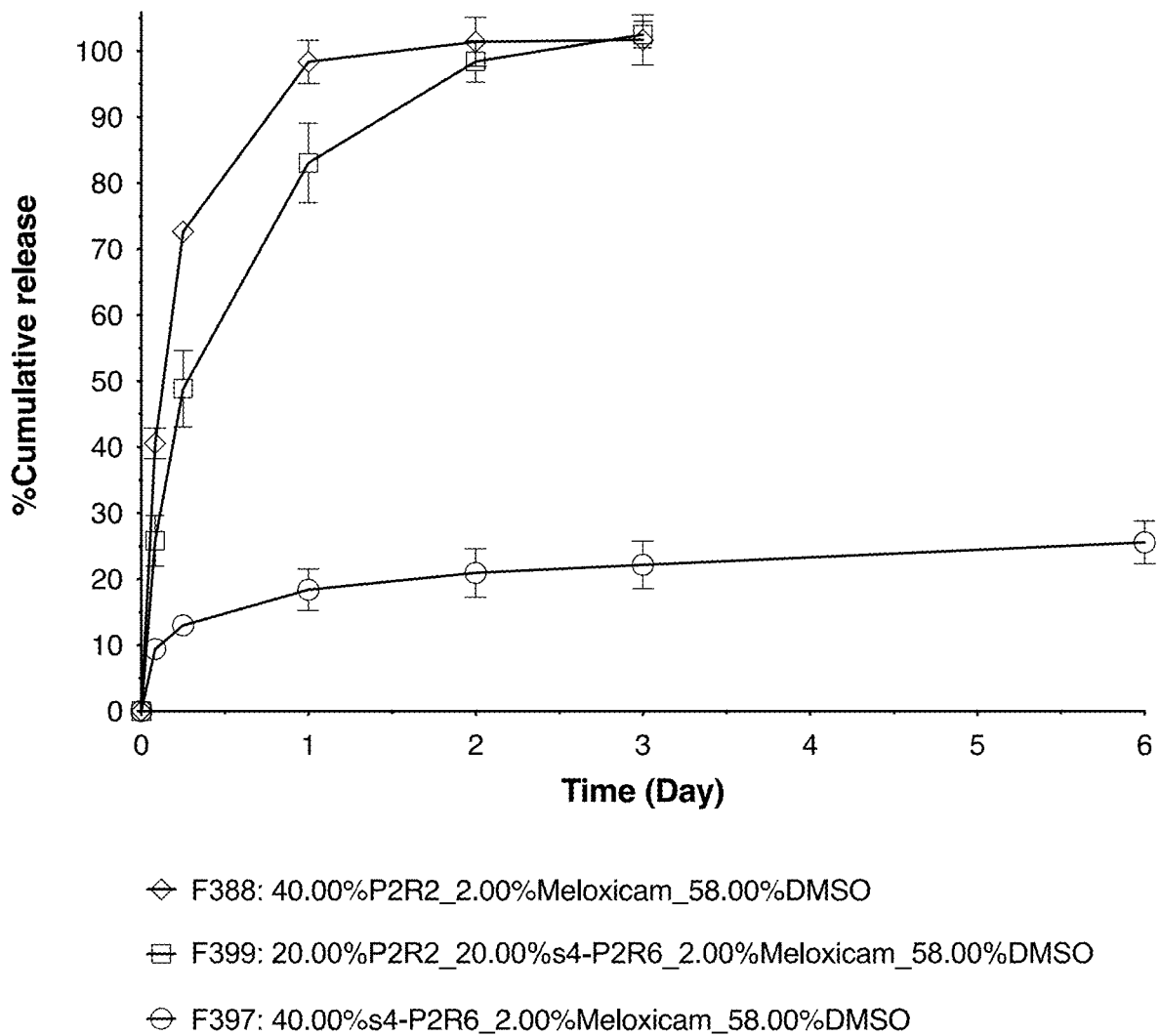

FIG. 42 displays the percentage in vitro cumulative release of meloxicam over time from three different formulations: Formulation F388 (◇) containing 40.00% of P2R2 linear copolymer with 2.00% active ingredient (API) and 58.00% of DMSO, formulation F397 (○) containing 40.00% of s4-P2R6 star-shaped copolymer with 2.00% active ingredient (API) and 58.00% of DMSO and formulation F399 (□) containing 20.00% of s4-P2R6 star-shaped copolymer and 20.00% of P2R2 linear copolymer with 2.00% active ingredient (API) and 58.00% of DMSO. In vitro release tests have been conducted according to set up 1 in table 2, example 3. The specific block copolymer formulations are set forth in Table 1.

Data shows that the mixture of linear and star-shaped copolymers in a formulation composition can lead to a modulated release profile.

Figure 43:
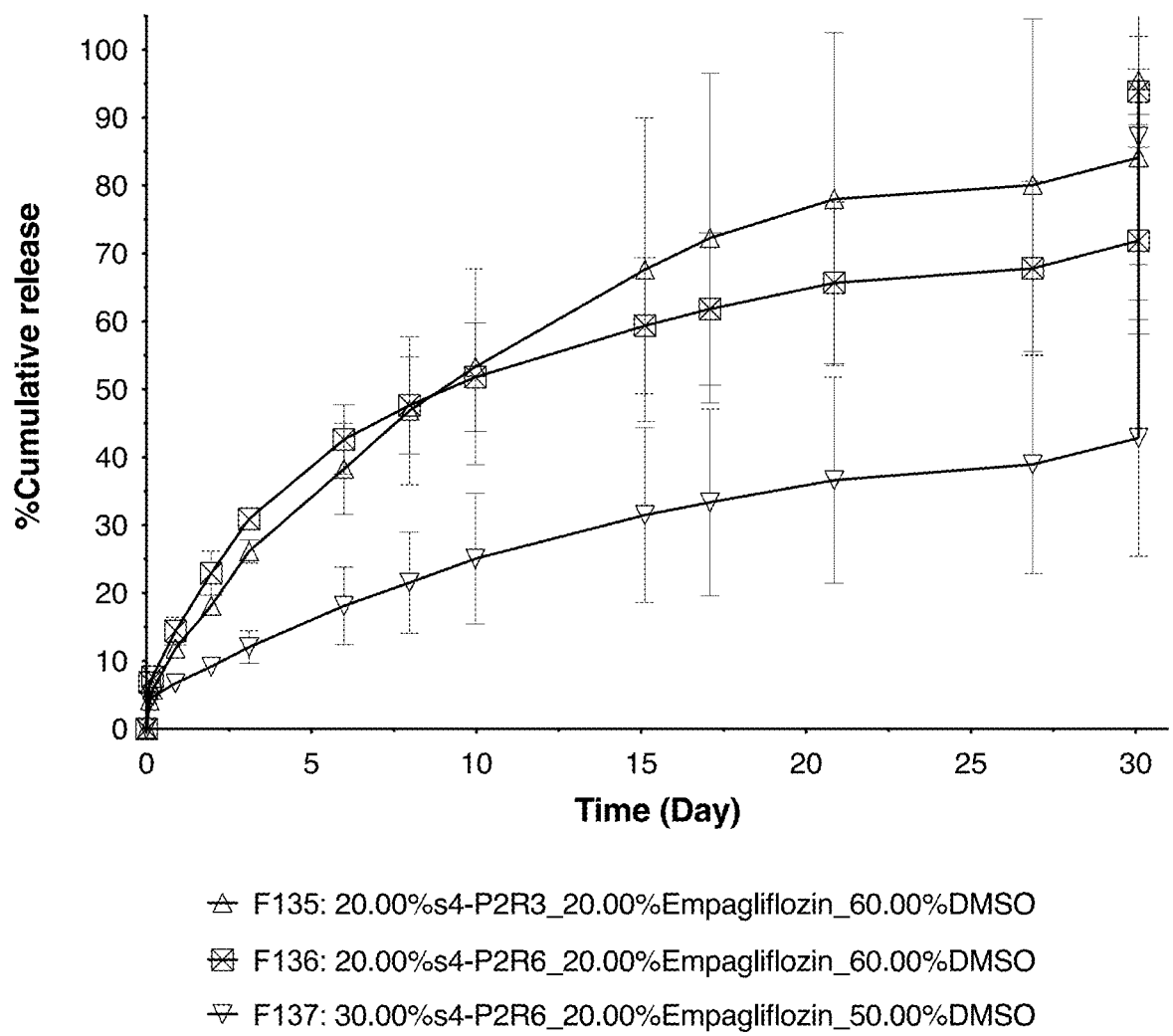

FIG. 43 shows the percentage in vitro cumulative release of empagliflozin over time from three different formulations: formulation F135 (Δ) containing 20.00% of s4-P2R3 star-shaped copolymer with 20.00% active ingredient (API) and 60.00% of DMSO, formulation F136 (□) containing 20.00% of s4-P2R6 star-shaped copolymer with 20.00% active ingredient (API) and 60.00% of DMSO and formulation F137 (∇) containing 30.00% of s4-P2R6 star-shaped copolymer with 20.00% active ingredient (API) and 50.00% of DMSO. In vitro release tests have been conducted according to set up 2 in table 2, example 3. The specific block copolymer formulations are set forth in Table 1 below.

Results demonstrate that star-shaped copolymer-based formulations exhibit sustained release kinetics of empagliflozin over time. Data demonstrate that the modification of the R ratio induces a modulation of obtained release profiles. Indeed, formulation F136 shows slower release kinetics than formulation F135. Data shows that the increase of the total copolymer content leads to a modulation of the release profile. F137 shows slower release kinetics than formulation F136.

Figure 44:
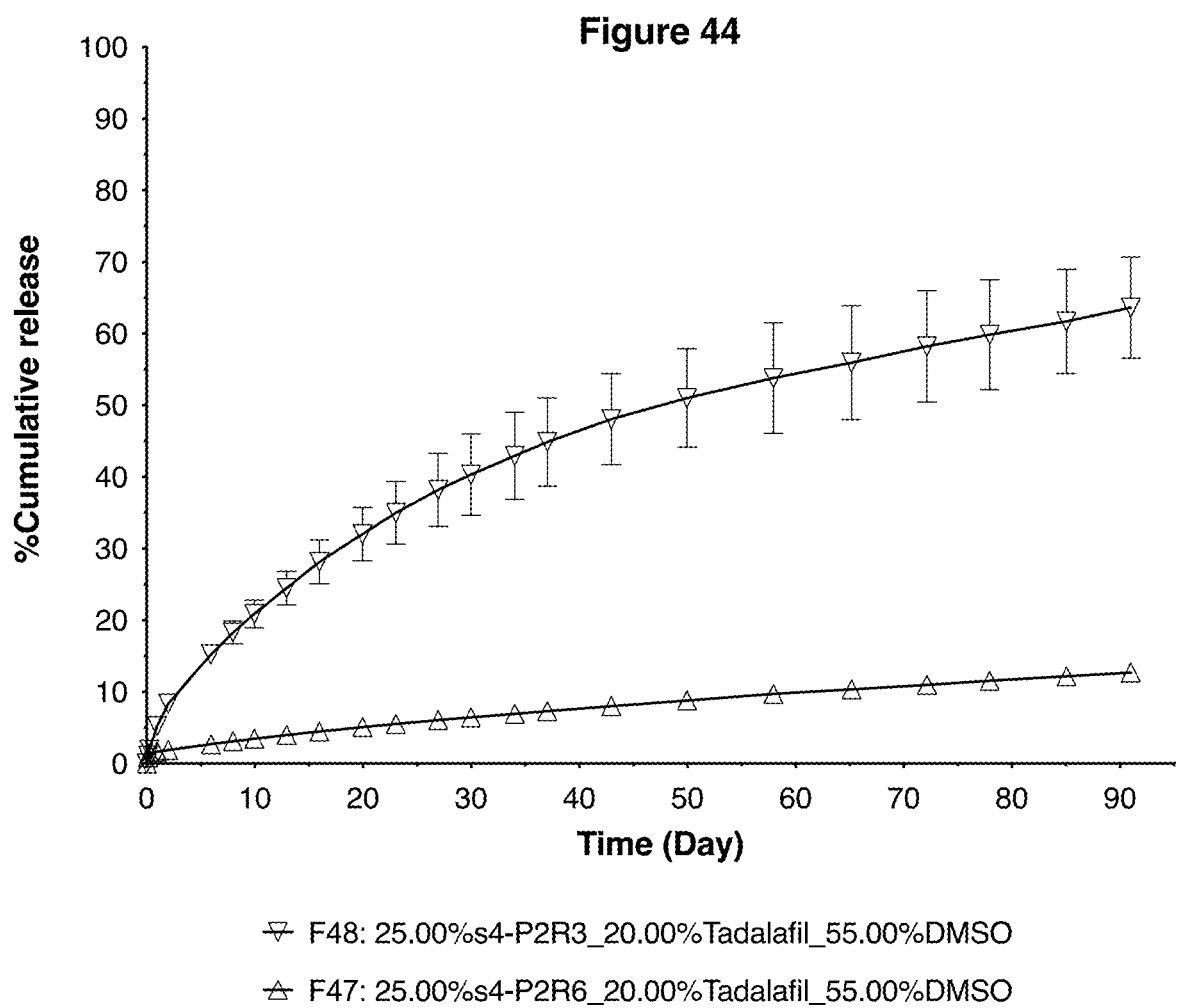

FIG. 44 is a graph showing the percentage total in vitro cumulative release of tadalafil over time from F47 and F48. Formulation F47 (Δ) contains 25.00% of s4-P2R6 star-shaped copolymer with 20.00% active ingredient (API) and 55.00% of DMSO. Formulation F48 (∇) contains 25.00% of s4-P2R3 star-shaped copolymer with 20.00% active ingredient (API) and 55.00% of DMSO. In vitro release tests have been conducted according to set up 3 in table 2, example 3. The specific block copolymer formulations are set forth in Table 1 below.

Data shows that star-shaped copolymer-based formulations allow sustained release of Tadalafil over time. Data demonstrate that the modification of R ratio induces a modulation of obtained release profiles. Indeed, formulation F47 shows slower release kinetics than formulation F48.

Figure 45:
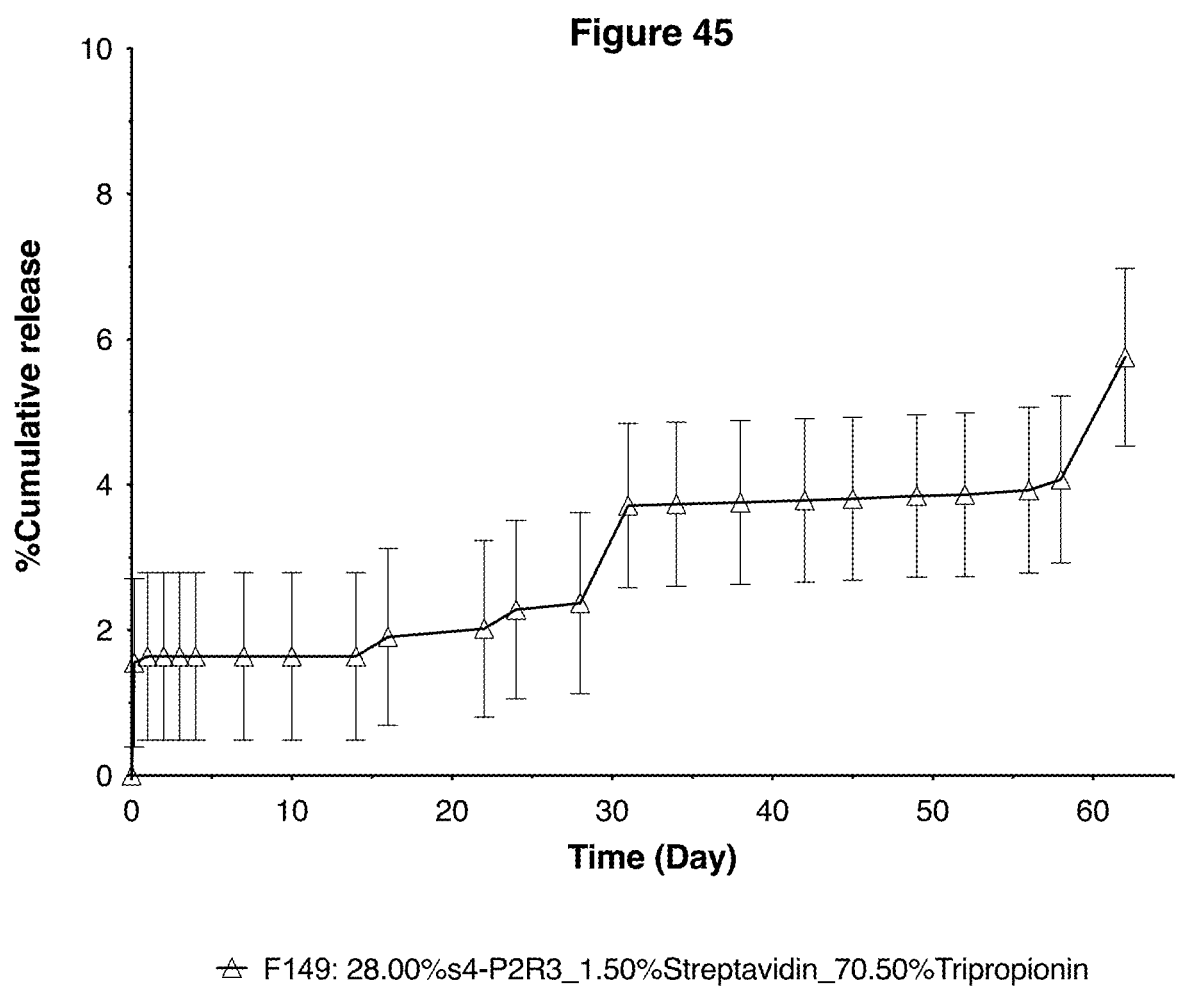

FIG. 45 is a graph showing the percentage total in vitro cumulative release of Streptavidin over time from F149. Formulation F149 (Δ) contains 28.00% of s4-P2R3 star-shaped copolymer with 1.50% active ingredient (API) and 70.50% of Tripropionin. In vitro release tests have been conducted according to set up 4 in table 2, example 3. The specific block copolymer formulations are set forth in Table 1 below.

Data shows that star-shaped copolymer-based formulations allow sustained release of Streptavidin over time.

Figure 46:
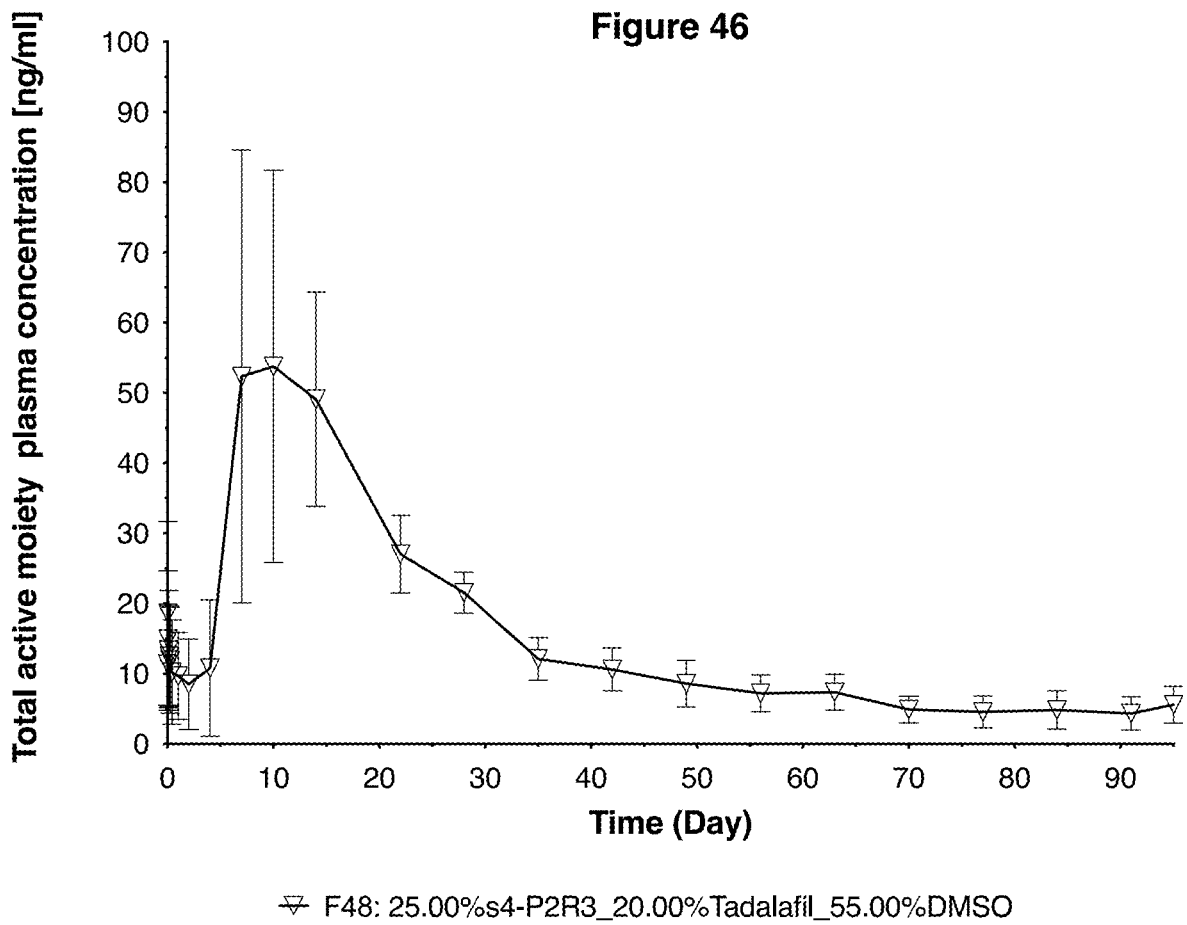

FIG. 46 is a graph showing the total active moiety plasma concentration expressed in nanogram per milliliter of tadalafil over time for F48 Formulation F48 (∇) contains 25.00% of s4-P2R3 star-shaped copolymer with 20.00% active ingredient (API) and 55.00% of DMSO. In vivo release tests have been conducted according to set up 2 in table 5, example 7.

Results indicate that, in accordance with the observations in vitro, the formulation allows sustained release of Tadalafil over time in vivo.

Figure 47:
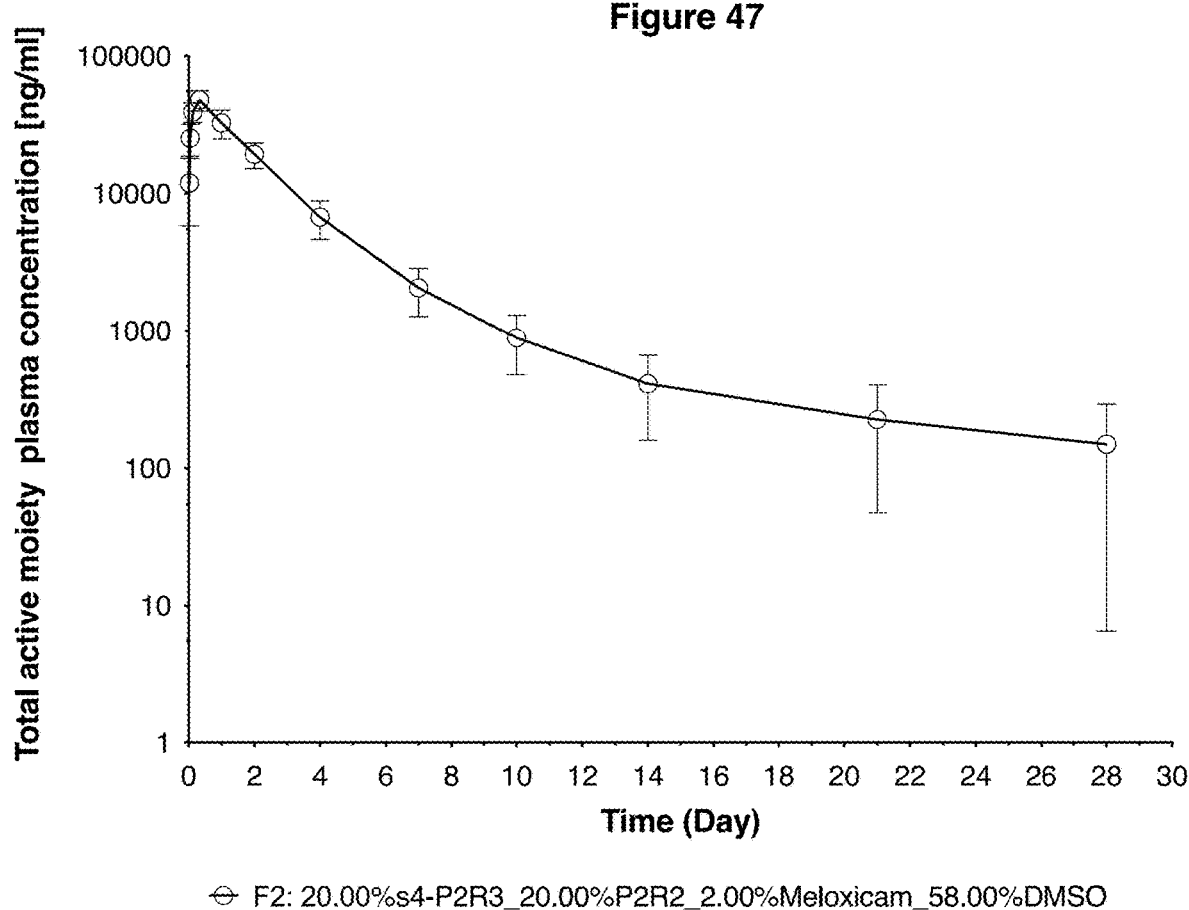

FIG. 47 is a graph showing the total active moiety plasma concentration expressed in nanogram per milliliter of meloxicam over time for formulation F2. F2 (○) contains 20.00% of s4-P2R3 star-shaped copolymer, 20.00% of P2R2 triblock copolymer with 2.00% active ingredient (API) and 58.00% of DMSO. In vivo release tests have been conducted according to set up 1 in table 5, example 7.

Results indicate that the combination of star-shaped and linear copolymer in formulation F2, led to a sustained release profile of meloxicam over time in vivo.

Figure 48:
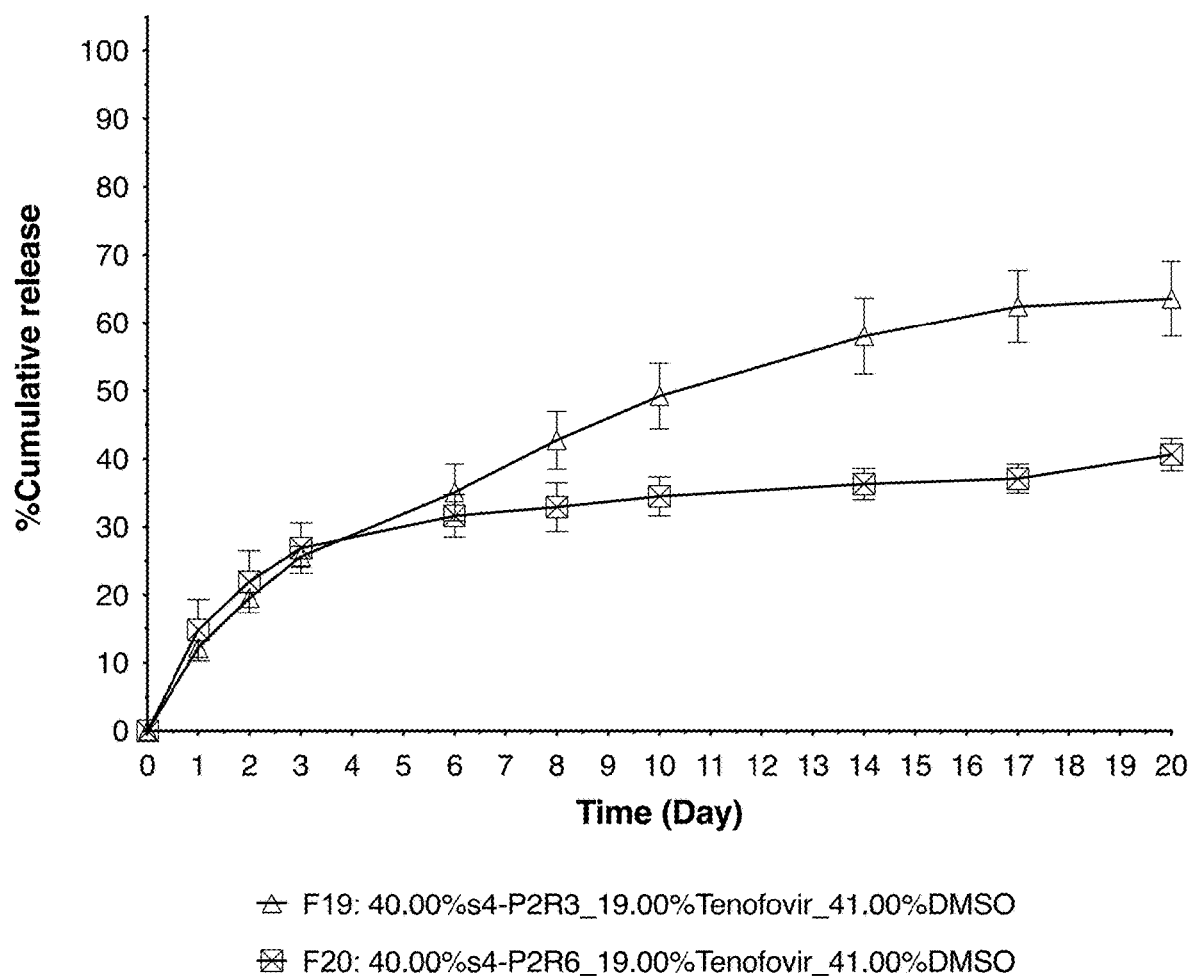

FIG. 48 displays the percentage in vitro cumulative release of tenofovir over time from two different formulations: Formulation F19 (Δ) containing 40.00% of s4-P2R3 star-shaped copolymer with 19.00% active ingredient (API) and 41.00% of DMSO and formulation F20 (□) containing 40.00% of s4-P2R6 star-shaped copolymer with 19.00% active ingredient (API) and 41.00% of DMSO. In vitro release tests have been conducted according to set up 5 in table 2, example 3.

Results demonstrate that the star-shaped copolymer-based formulations allow sustained release of tenofovir over time. Data demonstrate that the modification of R ratio induces a modulation of obtained release profiles. Indeed, formulation F20 shows slower release kinetics than formulation F19.

Figure 49:
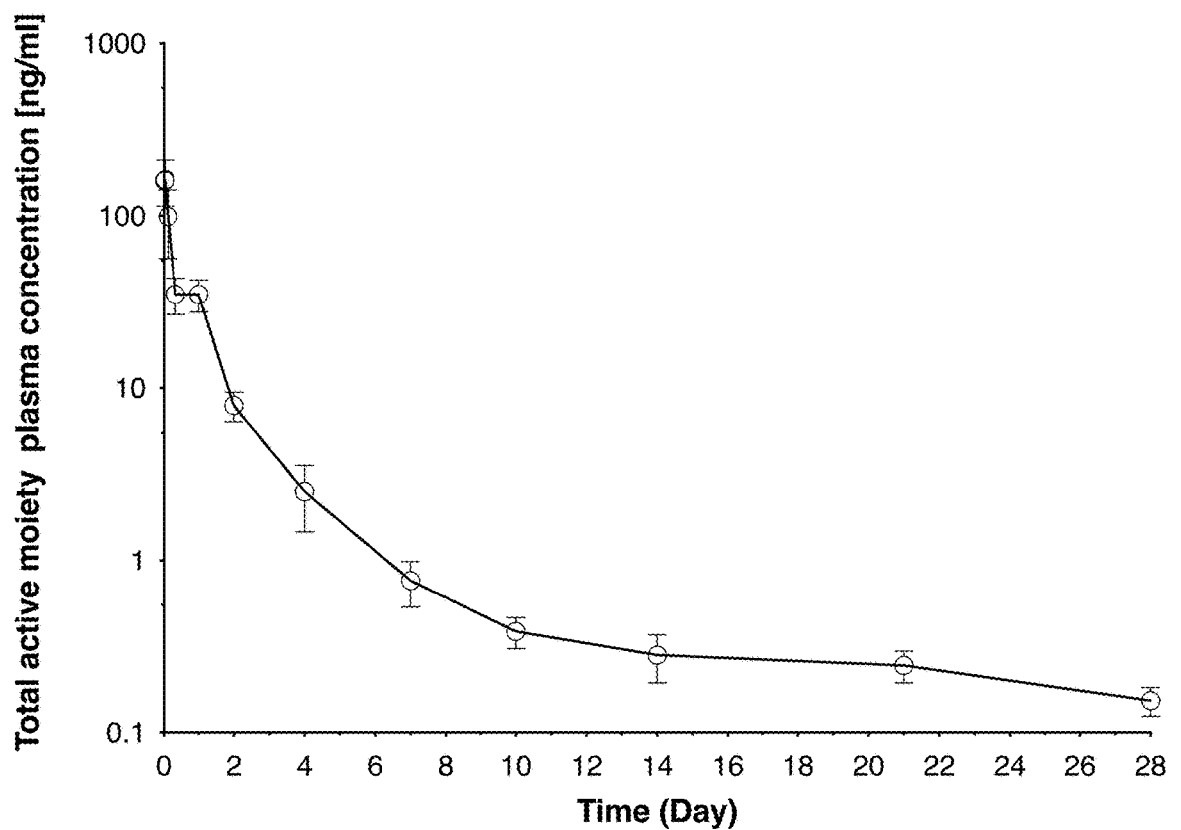

FIG. 49 is a graph showing the total active moiety plasma concentration expressed in nanogram per milliliter of octreotide over time for formulation F145. F145 (○) contains 28.00% of s4-P2R3 star-shaped copolymer, 18.00% of P1R4 triblock copolymer with 0.70% active ingredient (API) and 53.30% of DMSO. In vivo release tests have been conducted according to set up 3 in table 5, example 7.

Results indicate that the combination of star-shaped and linear copolymer in formulation F145, led to a sustained release profile of octreotide over time in vivo.

Figure 50:
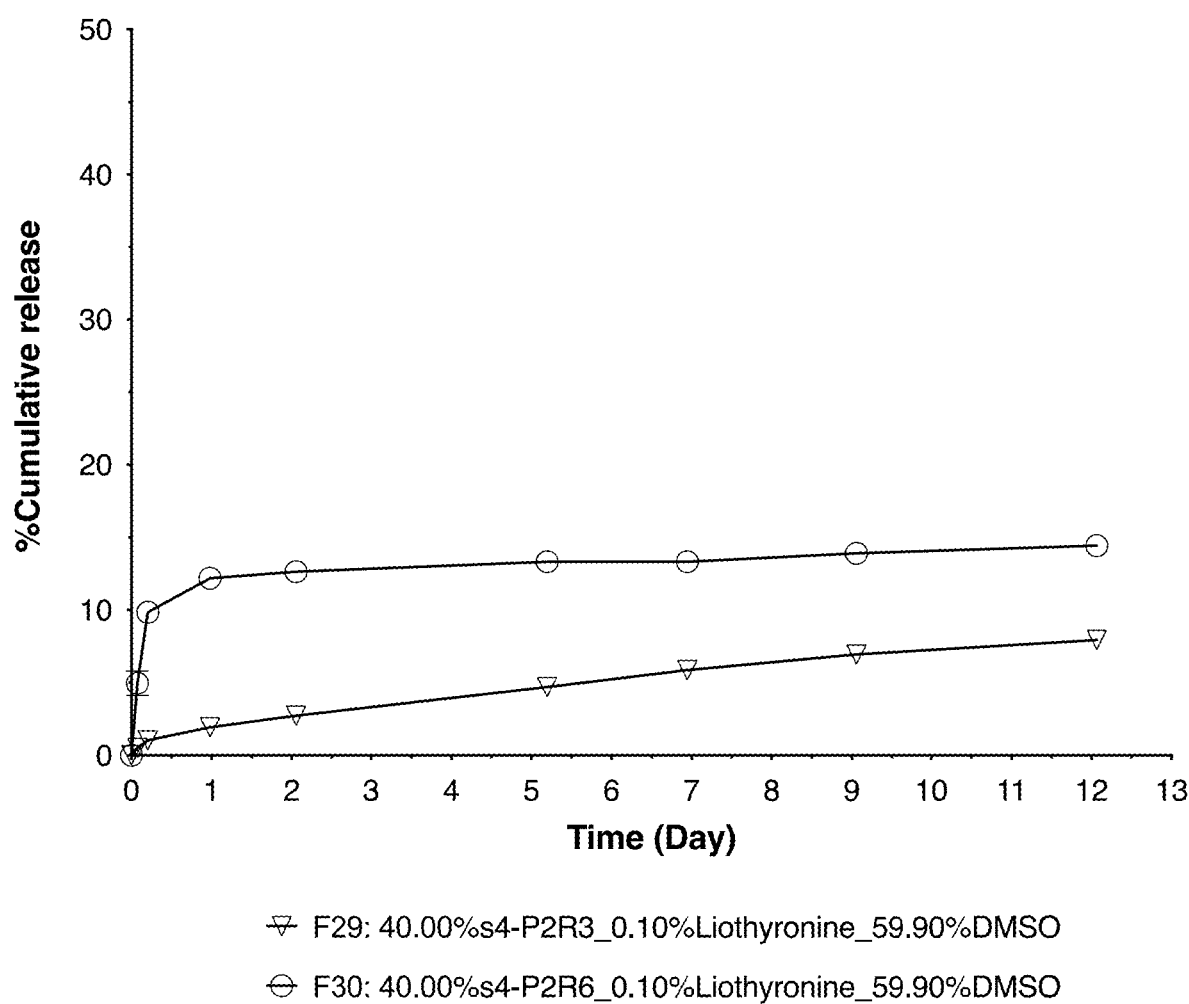

FIG. 50 displays the percentage in vitro cumulative release of tenofovir over time from two different formulations: Formulation F29 (∇) containing 40.00% of s4-P2R3 star-shaped copolymer with 0.10% active ingredient (API) and 59.90% of DMSO and formulation F30 (○) containing 40.00% of s4-P2R6 star-shaped copolymer with 0.10% active ingredient (API) and 59.90% of DMSO. In vitro release tests have been conducted according to set up 6 in table 2, example 3.

Results demonstrate that the star-shaped copolymer-based formulations allow sustained release of liothyronine over time. Data demonstrate that modification of the R ratio induces a modulation of obtained release profiles. Indeed, formulation F29 shows slower release kinetics than formulation F30.

Figure 51:
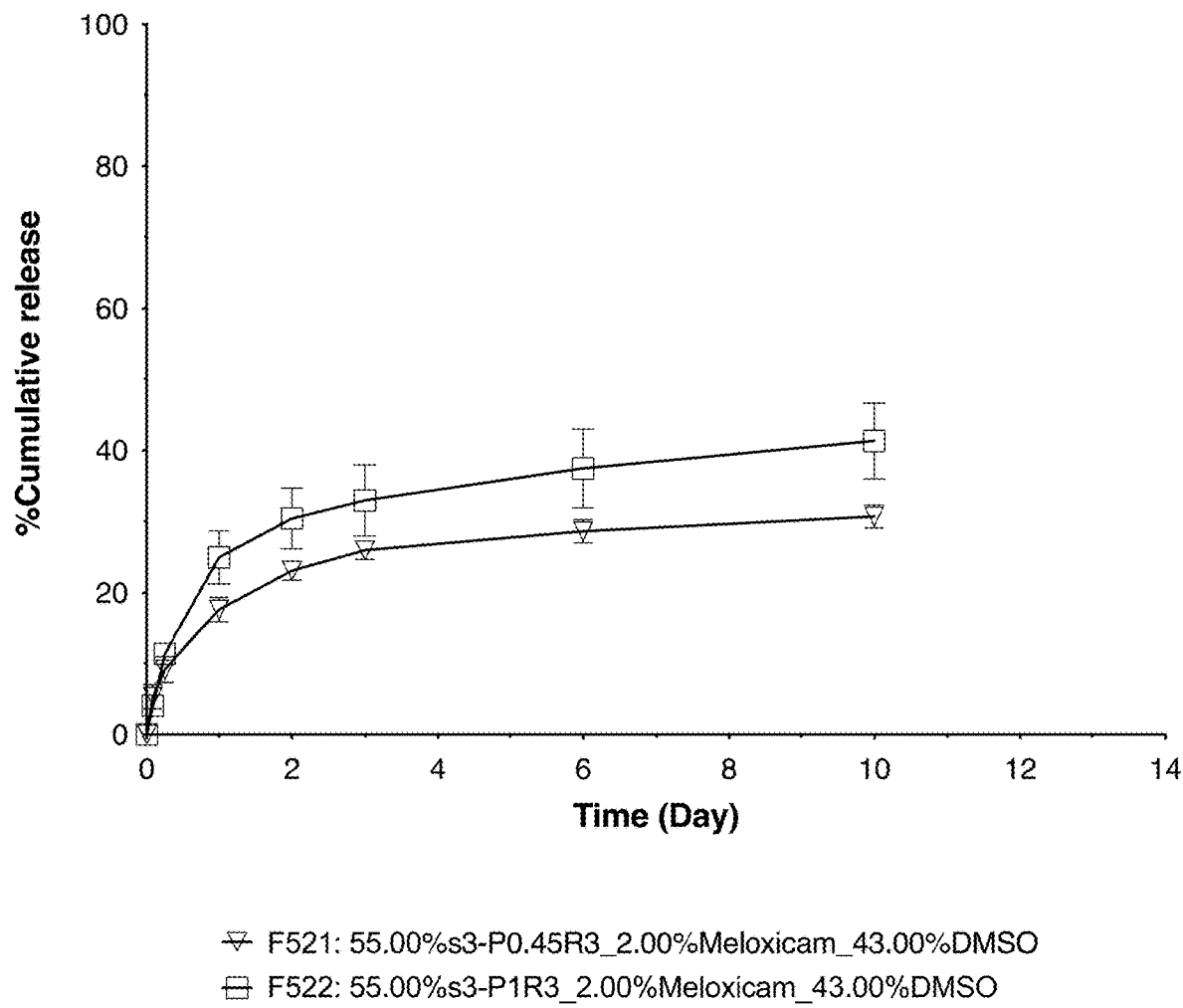

FIG. 51 displays the percentage in vitro cumulative release of meloxicam over time from two different formulations: Formulation F521 (∇) containing 55.00% of s3-P0.45R3 star-shaped copolymer with 2.00% active ingredient (API) and 43.00% of DMSO and formulation F522 (□) containing 55.00% of s3-P1R3 star-shaped copolymer with 2.00% active ingredient (API) and 43.00% of DMSO. In vitro release tests have been conducted according to set up 1 in table 2, example 3.

Results demonstrate that the increase of PEG chain length within the star-shaped copolymer with a fixed LA/EO ratio leads to a modulated release rate for formulations with the same copolymer content. Indeed, formulation F521 shows slower release kinetics than formulation F522.

EXAMPLES

Example 1: Materials

Star-Shaped Block Copolymers

Set out below is a generic reaction scheme to obtain multi-branched PEG-PLA as used in a pharmaceutical composition of the invention. The letters m and u describe the number of repetitive units in each PEG and PLA block respectively. Considering the synthetic pathway and experimental conditions, it is assumed that the multi-arm polymers are symmetrical, and each arm displays the same structure and composition. It will be understood that although in scheme 1 below, a 4-arm PEG derivative is used; an analogous reaction scheme can be used with a multi-branched PEG having a different number of PEG arms.

Scheme 1

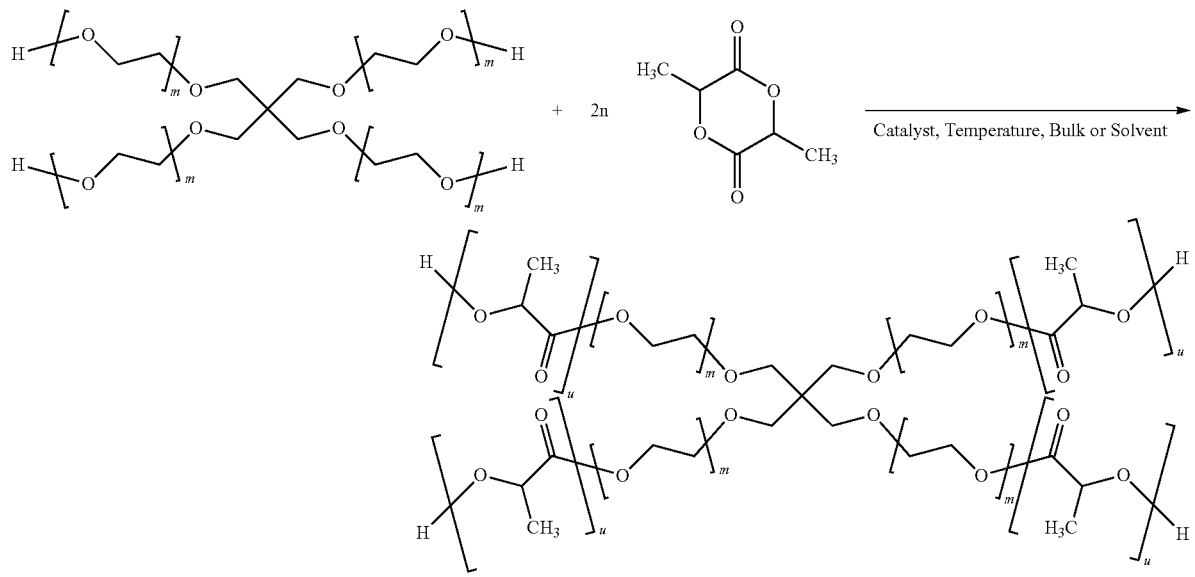

Multi-branched block copolymers were synthesized by ring-opening polymerization of D,L-lactide initiated by multi-branched polyethers referred to as multi-branched PEGs or star-PEGs (S. J. Buwalda et al., Influence of amide versus ester linkages on the properties of eight-armed PEG-PLA star block copolymer hydrogels, Biomacromolecules 11 (2010) 224-232). Star-PEGs are commercially available, for example from creative PEG works, for example 4-Arm PEG-OH as shown in scheme 1. Alternatively, multi-branched PEG can be formed by the reaction of ethylene oxide with a polyol.

The catalyst (such as monomer/catalyst mol/mol is 10000) was then added to the star-PEG at 80° C. in a reaction vessel and let to stir with the macroinitiator before adding the appropriate amount of D,L-lactide (the amount of monomer is determined depending on the targeted R ratio). To remove any water in the system, the mixture was further dried by several successive vacuum and nitrogen cycles. The reaction mixture was then heated and left to react for several hours (until complete conversion of the monomer). At the end of the polymerization reaction, the polymer is taken out of the reaction vessel and let to cool down. The polymer is then further purified to remove any unreacted monomer, catalyst and oligomers. To do so, the polymer mixture is dissolved in an appropriate solvent, namely acetone, and let to dissolve overnight. The polymer solution is then precipitated in a non-solvent of the block copolymer (i.e. ethanol). This step is repeated several times to ensure the recovering of the targeted polymer only. The collected polymer is left to dry under vacuum until all solvents have been extracted from the sample.

Star-shaped block copolymers were analysed and characterized after synthesis and purification to ensure that obtained polymers had the targeted structure and composition. To do so, $^1$H NMR in $CDCl_3$ and GPC analysis in chloroform were done.

$^1$H NMR was carried out by an external company according to their standard procedure on a Brucker advance 300 MHz spectrometer. For all $^1$H NMR spectrograms, MestReNova software was used for the integration of peaks and their analyses. Chemical shifts were referenced to the $\delta$=7.26 ppm solvent value of $CDCl_3$.

Gel permeation chromatography (GPC) measurements were carried out on a gel permeation chromatography triple detector array (GPC-TDA) apparatus supplied by Malvern. Between 150 and 200 mg of polymers were solubilized in 10 mL of chloroform (HPLC grade) over night before being put in a 1.5 mL vial for analysis with a closed cap. After determination of the dn/dc value for each polymer, 100 μL of polymer solution were injected 3 times in the GPC system. Each replicate was then separately analysed and integrated. $M_n$ and polydispersity index (PDI) values given above correspond to the mean value determined considering all the injections.

Linear Block Copolymers

The linear triblock copolymers compared with the star-shaped block copolymers typically have the formula:

Av-Bw-Ax wherein A is a polyester and B is polyethylene glycol and v and x are the number of repeat units ranging from 1 to 3,000 and w is the number of repeat units ranging from 3 to 300 and v=x or v≠x.

The linear diblock copolymers compared with the star-shaped block copolymers typically have the formula:

Cy-Az wherein A is a polyester and C is an end-capped polyethylene glycol and y and z are the number of repeat units with y ranging from 2 to 250 and z ranging from 1 to 3,000.

Typically the linear triblock copolymers compared with the star-shaped block copolymers have the formula:

LAv-EOw-LAx wherein v and x are the number of repeat units ranging from 1 to 3,000 and w is the number of repeat units ranging from 3 to 300 and v=x or v≠x.

Typically the linear diblock copolymers compared with the star-shaped block copolymers have the formula:

m(EO)y-LAz wherein y and z are the number of repeat units with y ranging from 2 to 250 and z ranging from 1 to 3,000.

Block copolymers were synthesized according to the method described in U.S. Pat. No. 6,350,812, incorporated herein by reference, with minor modifications. Typically, the necessary amount of PEG (in the triblock copolymer) or methoxy-PEG (in the diblock copolymer) was heated at 80° C. and dried under vacuum for 30 minutes in a reactor vessel. D,L-lactide (corresponding to the targeted LA/EO molar ratio) and catalyst (1/1000 of amount of lactide) were added. In order to avoid any side reaction due to the presence of water, the reaction mixture was subjected to two short cycles of vacuum/N2 cycles. The reaction was then heated at 130° C. under constant nitrogen flow (0.2 bar). Once the reaction was stopped, the block copolymer was discharged from the vessel and left to cool down. The obtained polymer sample was then solubilized in acetone before being precipitated in a high volume of non-solvent (ratio non-solvent/solvent=6-10) to remove any unreacted monomer, catalyst or oligomers present in the sample. This purification process was repeated twice. The collected polymer was then left to dry under vacuum to remove any traces of solvent and only recover the targeted polymer.

The product obtained was characterized by $^1$H NMR for its residual lactide content and for the determination of the R ratio.

$^1$H NMR spectroscopy was performed using a Brucker advance 300 MHz spectrometer. For all $^1$H NMR spectrograms, MestReNova software was used for the integration of peaks and their analyses. Chemical shifts were referenced to the δ=7.26 ppm solvent value of CDCl$_3$.

For the determination of the R ratio, that describes the ratio between lactic acid units over ethylene oxide units (LA/EO), all peaks were separately integrated. The intensity of the signal (integration value) is directly proportional to the number of hydrogens that constitutes the signal. So, and to determine the R ratio (LA/EO ratio), the integration values need to be homogenous and representative of the same number of protons (e.g. all signal values are determined for 1H). A characteristic peak of PLA and one of PEG are then used to determine the LA/EO ratio. This method is valid for molecular weight of PEGs above 1000 g/mol where the signal obtained for the polymer end-functions can be neglected.

Example 2: Analysis of Soluble Fraction of Star-Shaped Copolymers in Water

Water solubility tests were performed to determine the soluble fraction of star-shaped copolymer in water.

Water solubility analysis consisted of the following steps:

Empty 20 ml vials were weighed (1). 500 mg of copolymer was weighed and added to the corresponding vial. 5 mL of ultra-pure water was added to each vial. Vials were incubated for 2 h at 37° C. with vortexing. Visual observations were carried out and pictures were taken. The vials (1) were then centrifuged for 10 mins at 3000 rpm. A 10 mL glass vial (2) was weighed. The supernatant of (1) was transferred into (2) and masses were recorded. The wet copolymer in (1) was weighed. (1) and (2) were placed at −80° C. overnight. (1) and (2) were placed in the freeze dryer for 22h. Vials (1) and (2) were weighed. Water solubility was determined after drying and weighing the remaining dried copolymer. The amount of dissolved copolymer was determined as the difference of weight of the empty vial and the lyophilized one. The analysis of water solubility was performed in a single analysis.

Results show water solubility values of 2.7 mg/mL, 1.7 mg/ml and 1.7 mg/mL for s4-P2R2, s4-P2R6 and s4-P5R4, respectively.

Example 3: In Vitro Release Tests

Set-Up 1 Detailed Procedure 50 mg of meloxicam-containing formulation was added to 20 ml of buffer in an Erlenmeyer flask.

The buffer used is phosphate-buffered saline (PBS) pH 7.4, which was 137 mM sodium chloride, 2.7 mM potassium chloride, 10 mM disodium phosphate, 1.8 mM monopotassium phosphate and 0.1% sodium azide. Upon injection, the solvent diffused away from the formulation and the remaining polymer forms an in situ depot within the aqueous environment.

Closed Erlenmeyer flasks were maintained under constant shaking at 180 rpm (Unimax 1010 apparatus, Heidolph) at 37° C. At pre-determined time intervals, 2 mL of medium were collected and analysed by UPLC; the rest of the medium was discarded and 20 mL of fresh buffer were added to the Erlenmeyer. Sink conditions were maintained during the full duration of the study. The amount of meloxicam released from the formulation was calculated from a calibration curve where the concentration of meloxicam ranges between 0 and 160 μg/ml.

The meloxicam incorporated into the polymer solution was encapsulated within the polymer matrix as it solidifies.

In vitro release (IVR) was analysed following the consecutive steps detailed below:

Formulation Preparation

In an empty and tared 3 mL glass vial, required copolymer amounts were weighed. The glass vial was tared again. An accurate DMSO mass was added using a Pasteur pipette. Vehicles (copolymer+solvent) were then placed on a roller mixer at room temperature (RT) for 6 to 7 hours until complete copolymer dissolution. Glass vials were then tared and the required API amount was weighed. The formulations were then placed overnight at room temperature on a roller mixer.

IVR Start

50 μL of formulation were withdrawn from the corresponding glass vial previously vortexed, into a 0.5 mL Codan syringe. The syringe was cleaned, tared and the formulation was directly injected from the syringe without needle, into a 50 mL prefilled glass vial containing 20 mL of release buffer (PBS 1×). Once precipitation and depot formation had occurred, the depot was cut from the syringe using scissors. The syringe was weighed back to determine the accurate depot mass.

Once all depots were formed, glass vials were placed on a stirrer at 37° C.

IVR Sampling and Preparation of IVR Samples for API Quantification

At each desired time point, a sufficient amount of buffer was withdrawn for analysis from the 50 mL glass vial before total buffer refreshment. 1 mL of each sample was filtered through a 0.2 μm hydrophilic filter into a 1 mL HPLC glass vial. API contents in released buffer were determined using UPLC.

Some parameters, for example the mass of formulation, the buffer type or buffer volume may be adapted depending on the studied API, its solubility in different buffers and its targeted dose and release duration. Set-up with different parameters is presented in Table 2 below.

All of the studied formulations are presented in Table 1 below.

TABLE 1

| Formulation Number | API | | Copolymer | | | | | Solvent | |
|---|---|---|---|---|---|---|---|---|---|
| | Name | % (w/w) | Code | Structure | PEG size (Da)) | Ratio (LA/EO) | % (w/w) | Name | % (w/w) |
| 2 | Meloxicam | 2.00 | s4-P2R3 | Branched | 2000 | 3 | 20.00 | DMSO | 58.00 |
| | | | P2R2 | Linear | 2000 | 2 | 20.00 | | |
| 19 | Tenofovir | 19.00 | s4-P2R3 | Branched | 2000 | 3 | 40.00 | DMSO | 41.00 |
| 20 | Tenofovir | 19.00 | s4-P2R6 | Branched | 2000 | 6 | 40.00 | DMSO | 41.00 |
| 29 | Liothyronine | 0.10 | s4-P2R3 | Branched | 2000 | 3 | 40.00 | DMSO | 59.90 |
| 30 | Liothyronine | 0.10 | s4-P2R6 | Branched | 2000 | 6 | 40.00 | DMSO | 59.90 |
| 47 | Tadalafil | 20.00 | s4-P2R6 | Branched | 2000 | 6 | 25.00 | DMSO | 55.00 |
| 48 | Tadalafil | 20.00 | s4-P2R3 | Branched | 2000 | 3 | 25.00 | DMSO | 55.00 |
| 135 | Empagliflozin | 20.00 | s4-P2R3 | Branched | 2000 | 3 | 20.00 | DMSO | 60.00 |
| 136 | Empagliflozin | 20.00 | s4-P2R6 | Branched | 2000 | 6 | 20.00 | DMSO | 60.00 |
| 137 | Empagliflozin | 20.00 | s4-P2R6 | Branched | 2000 | 6 | 30.00 | DMSO | 50.00 |
| 145 | Octreotide | 0.70 | s4-P2R3 | Branched | 2000 | 3 | 28.00 | DMSO | 53.30 |
| | | | P1R4 | Linear | 1000 | 4 | 18.00 | | |
| 149 | Streptavidin | 1.50 | s4-P2R3 | Branched | 2000 | 3 | 28 | Tripropionin | 70.50 |
| 388 | Meloxicam | 2.00 | P2R2 | Linear | 2000 | 2 | 40.00 | DMSO | 58.00 |
| 389 | Meloxicam | 2.00 | s4-P2R2 | Branched | 2000 | 2 | 40.00 | DMSO | 58.00 |
| 390 | Meloxicam | 2.00 | P2R2 | Linear | 2000 | 2 | 20.00 | DMSO | 58.00 |
| | | | s4-P2R2 | Branched | 2000 | 2 | 20.00 | | |
| 391 | Meloxicam | 2.00 | P2R3.5 | Linear | 2000 | 3.5 | 40.00 | DMSO | 58.00 |
| 396 | Meloxicam | 2.00 | P2R6 | Linear | 2000 | 6 | 40.00 | DMSO | 58.00 |
| 397 | Meloxicam | 2.00 | s4-P2R6 | Branched | 2000 | 6 | 40.00 | DMSO | 58.00 |
| 399 | Meloxicam | 2.00 | P2R2 | Linear | 2000 | 2 | 20.00 | DMSO | 58.00 |
| | | | s4-P2R6 | Branched | 2000 | 6 | 20.00 | DMSO | 58.00 |
| 401 | Meloxicam | 2.00 | s4-P2R2 | Branched | 2000 | 2 | 20.00 | DMSO | 58.00 |
| | | | s4-P2R6 | Branched | 2000 | 6 | 20.00 | | |
| 402 | Meloxicam | 2.00 | s4-P5R2 | Branched | 5000 | 2 | 40.00 | DMSO | 58.00 |
| 404 | Meloxicam | 2.00 | s4-P5R2 | Branched | 5000 | 2 | 20.00 | DMSO | 58.00 |
| | | | s4-P2R6 | Branched | 2000 | 6 | 20.00 | | |
| 405 | Meloxicam | 2.00 | s4-P2R3 | Branched | 2000 | 3 | 40.00 | DMSO | 58.00 |
| 407 | Bupivacaine | 2.00 | P2R2 | Linear | 2000 | 2 | 40.00 | DMSO | 58.00 |
| 408 | Bupivacaine | 2.00 | s4-P2R2 | Branched | 2000 | 2 | 40.00 | DMSO | 58.00 |
| 409 | Bupivacaine | 2.00 | s4-P2R2 | Branched | 2000 | 2 | 20.00 | DMSO | 58.00 |
| | | | P2R2 | Linear | 2000 | 2 | 20.00 | | |
| 413 | Bupivacaine | 2.00 | P2R6 | Linear | 2000 | 6 | 40.00 | DMSO | 58.00 |
| 414 | Bupivacaine | 2.00 | s4-P2R6 | Branched | 2000 | 6 | 40.00 | DMSO | 58.00 |
| 449 | Meloxicam | 2.00 | dP2R3 | Linear | 2000 | 3 | 45.00 | DMSO | 53.00 |
| 451 | Meloxicam | 2.00 | s4-P2R3 | Branched | 2000 | 3 | 47.00 | DMSO | 51.00 |
| 460 | Tamsulosin | 2.00 | s4-P2R6 | Branched | 2000 | 6 | 40.00 | DMSO | 58.00 |
| 463 | Tamsulosin | 14.40 | s4-P2R6 | Branched | 2000 | 6 | 40.00 | DMSO | 45.60 |
| 483 | Meloxicam | 2.00 | P2R3.5 | Linear | 2000 | 3.5 | 44.00 | NMP | 54.00 |
| 484 | Meloxicam | 2.00 | dP2R3 | Linear | 2000 | 3 | 47.00 | NMP | 51.00 |
| 485 | Meloxicam | 2.00 | P2R3.5 | Linear | 2000 | 3.5 | 22.00 | Triacetin | 76.00 |
| 486 | Meloxicam | 2.00 | dP2R3 | Linear | 2000 | 3 | 24.00 | Triacetin | 74.00 |
| 488 | Meloxicam | 2.00 | s4-P2R3 | Branched | 2000 | 3 | 26.00 | Triacetin | 72.00 |
| 489 | Meloxicam | 2.00 | s4-P2R3 | Branched | 2000 | 3 | 51.00 | NMP | 47.00 |
| 496 | Tamsulosin | 2.00 | P2R2 | Linear | 2000 | 2 | 40.00 | DMSO | 58.00 |
| 497 | Tamsulosin | 2.00 | s4-P2R2 | Branched | 2000 | 2 | 40.00 | DMSO | 58.00 |
| 498 | Tamsulosin | 2.00 | dP2R3 | Linear | 2000 | 3 | 40.00 | DMSO | 58.00 |
| 499 | Tamsulosin | 2.00 | s4-P2R3 | Branched | 2000 | 3 | 40.00 | DMSO | 58.00 |
| 509 | Meloxicam | 2.00 | dP2R0.8 | Linear | 2000 | 0.8 | 68.00 | DMSO | 30.00 |
| 510 | Meloxicam | 2.00 | dP2R1.5 | Linear | 2000 | 1.5 | 61.00 | DMSO | 37.00 |
| 511 | Meloxicam | 2.00 | dP2R6 | Linear | 2000 | 6 | 38.00 | DMSO | 60.00 |
| 521 | Meloxicam | 2.00 | s3-P0045R3 | Branched | 450 | 3 | 55.00 | DMSO | 43.00 |
| 522 | Meloxicam | 2.00 | s2-P1R3 | Branched | 1000 | 3 | 55.00 | DMSO | 43.00 |

TABLE 2

| IVR Set-up Number | Procedure | Injected mass (mg) | Syringe use | Needle use | Buffer Type | Volume (mL) |
|---|---|---|---|---|---|---|
| 1 | Injected in the medium from the syringe without needle | 60 | 0.5 mL Codan syringe | none | PBS-1X | 20 |
| 2 | Injected in the medium from the syringe with a needle | 250 | 1 mL softJect luer lock | 19G*1.1 × 50 mm | PBS-1X | 100 |
| 3 | Injected in the medium from the syringe with a needle | 150 | 1 mL softJect luer lock | 21G*0.8 × 16 mm | PBS-1X + 1% tween80 | 150 |
| 4 | Injected in the medium from the syringe without needle | 100 | 0.5 mL Codan syringe | none | SEC-1X | 20 |
| 5 | Injected in the medium from the syringe with a needle | 250 | 1 mL softJect luer lock | 21G*1.1 × 50 mm | KRT-1X + 2% tween80 | 33 |
| 6 | Injected in the medium from the syringe with a needle | 1000 | 1 mL softJect Luer lock | 21G 1.1 × 50 mm | PBS-1X + 1% Triton X100 | 20 |

Example 4: Depot Degradation Assessment

Depot degradation assessment was conducted by quantifying the lactic acid in the buffer used for IVR tests at every sampling time point. The amount of lactic acid in the medium is linked to the degradation of PLA chains.

First the samples were hydrolysed. 500 µL of released medium was transferred into a 1.5 mL Eppendorf tube. 250 µL of NaOH 5M is added. The Eppendorf was placed 1 hour at 40° C. The reaction was stopped by adding 250 µL of HCl 5 M.

The material used was a commercial kit called "Megazyme L-lactic acid Kit®" commercially available from Libios, Pontcharra-sur-Turdine, France. Lactic acid quantification was performed using the standard protocol without any modification.

Example 5: Injectability

The objective of this experiment was to assess the potential impact of using star-shaped copolymers on the injectability of the formulations by comparing the values to that of formulations with analogue linear copolymers.

Injectability analyses were performed using a Lloyd Instruments FT plus texturometer following the procedure described below:

Formulations (copolymer dissolved in the organic solvent) were vortexed for 15 seconds. 500 µL of formulation was withdrawn using a 1 mL Codan syringe without needle. Air bubbles were removed to avoid any interference during the injectability measurement. A 23G 1" Terumo needle was then mounted on the syringe, for vehicles or formulations respectively. The syringe was placed onto the texturometer. The flow rate was fixed at 1 mL/min. The speed rate was fixed at 56.3 mm/min. Injection of the formulation started at fixed speed. The injection device (i.e. syringe+needle) was changed for each replicate.

The average force in Newton (N) necessary to inject each replicate was calculated using texturometer software. Using the set up described above, the inventors defined 20 N as the maximum value for having a formulation that can be easily injected by hand.

TABLE 3

| Formulation Number | API Name | % (w/w) | Copolymer Code | Structure | % (w/w) | Solvent Name | % (w/w) | Number of replicates | Force (N) | Standard deviation |
|---|---|---|---|---|---|---|---|---|---|---|
| 388 | Meloxicam | 2.00 | P2R2 | Linear | 40.00 | DMSO | 58.00 | 6 | 6.3 | 1.1 |
| 389 | Meloxicam | 2.00 | s4-P2R2 | Branched | 40.00 | DMSO | 58.00 | 6 | 4.2 | 0.6 |
| 391 | Meloxicam | 2.00 | P2R3.5 | Linear | 40.00 | DMSO | 58.00 | 6 | 15.7 | 1.0 |
| 396 | Meloxicam | 2.00 | P2R6 | Linear | 40.00 | DMSO | 58.00 | 6 | 57.1 | 3.9 |
| 397 | Meloxicam | 2.00 | s4-P2R6 | Branched | 40.00 | DMSO | 58.00 | 6 | 21.6 | 1.6 |
| 449 | Meloxicam | 2.00 | dP2R3 | Linear | 45.00 | DMSO | 53.00 | 6 | 20.4 | 0.5 |
| 451 | Meloxicam | 2.00 | s4-P2R3 | Branched | 47.00 | DMSO | 51.00 | 6 | 15.9 | 1.4 |
| 483 | Meloxicam | 2.00 | P2R3.5 | Linear | 44.00 | NMP | 54.00 | 6 | 19.2 | 0.9 |
| 484 | Meloxicam | 2.00 | dP2R3 | Linear | 47.00 | NMP | 51.00 | 6 | 19.2 | 1.1 |
| 489 | Meloxicam | 2.00 | s4-P2R3 | Branched | 51.00 | NMP | 47.00 | 6 | 17.2 | 1.3 |
| 509 | Meloxicam | 2.00 | dP2R0.8 | Linear | 68.00 | DMSO | 30.00 | 6 | 19.0 | 1.1 |
| 510 | Meloxicam | 2.00 | dP2R1.5 | Linear | 61.00 | DMSO | 37.00 | 6 | 21.3 | 2.7 |
| 511 | Meloxicam | 2.00 | dP2R6 | Linear | 38.00 | DMSO | 60.00 | 6 | 20.6 | 0.5 |

Example 6: Dynamic Viscosity Analysis

Dynamic viscosity analysis was performed using an Anton Paar Rheometer equipped with cone plate measuring system, with the following analytical conditions:

Temperature controlled at 25° C.
Amount of vehicle: 0.25 mL.
Measuring system: Cone plate of 25 mm diameter and cone angle of 1 degree (CP25-1).
Working range: from 10 to 1000 mPa·s.

The formulation was vortexed for 10 seconds before analysis. 250 µL of formulation was placed at the centre of the thermo-regulated measuring plate using a spatula. The measuring system was lowered down and a 0.051 mm gap was left between the measuring system and the measuring plate. Twenty-one viscosity measurements points were determined across the 10 to 1000 $s^{-1}$ shear rate (10 points per decade). Viscosity data correspond to those calculated at a shear rate of 100 $s^{-1}$ which is an average value of the curve plateau. The analysis of formulation dynamic viscosity was performed in triplicate.

TABLE 4

| | API | | Copolymer | | | Solvent | | Number of replicates | Viscosity | |
|---|---|---|---|---|---|---|---|---|---|---|
| Formulation Number | Name | % (w/w) | Code | Structure | % (w/w) | Name | % (w/w) | | Dynamic viscosity (mP · s) | Standard deviation |
| 388 | Meloxicam | 2.00 | P2R2 | Linear | 40.00 | DMSO | 58.00 | 6 | 341.2 | 5.9 |
| 389 | Meloxicam | 2.00 | s4-P2R2 | Branched | 40.00 | DMSO | 58.00 | 6 | 213.5 | 1.8 |
| 391 | Meloxicam | 2.00 | P2R3.5 | Linear | 40.00 | DMSO | 58.00 | 6 | 1001.7 | 3.3 |
| 396 | Meloxicam | 2.00 | P2R6 | Linear | 40.00 | DMSO | 58.00 | 6 | 4602.9 | 123.1 |
| 397 | Meloxicam | 2.00 | s4-P2R6 | Branched | 40.00 | DMSO | 58.00 | 6 | 1790.7 | 26.1 |
| 449 | Meloxicam | 2.00 | dP2R3 | Linear | 45.00 | DMSO | 53.00 | 6 | 1427.0 | 28.2 |
| 451 | Meloxicam | 2.00 | s4-P2R3 | Branched | 47.00 | DMSO | 51.00 | 6 | 1083.7 | 5.7 |
| 483 | Meloxicam | 2.00 | P2R3.5 | Linear | 44.00 | NMP | 54.00 | 6 | 1286.4 | 20.7 |
| 484 | Meloxicam | 2.00 | dP2R3 | Linear | 47.00 | NMP | 51.00 | 6 | 1376.3 | 6.6 |
| 489 | Meloxicam | 2.00 | s4-P2R3 | Branched | 51.00 | NMP | 47.00 | 6 | 1182.0 | 7.1 |
| 509 | Meloxicam | 2.00 | dP2R0.8 | Linear | 68.00 | DMSO | 30.00 | 6 | 1232.3 | 17.2 |
| 510 | Meloxicam | 2.00 | dP2R1.5 | Linear | 61.00 | DMSO | 37.00 | 6 | 1579.9 | 15.1 |
| 511 | Meloxicam | 2.00 | dP2R6 | Linear | 38.00 | DMSO | 60.00 | 6 | 1465.3 | 23.4 |

Example 7: Pharmacokinetic Study

In Vivo Detailed Set-Up 1 Procedure

Several meloxicam formulations were tested in a pharmacokinetic study in male adult rats with a weight between 300 and 350 g. Drug products containing 3.6 mg of meloxicam were subcutaneously administered in the interscapular area of the rats using 1 mL Soft Ject® syringes and 23G (1" 0.6×25 mm) Terumo® needles. Injected formulation volumes were fixed to 160 µL. Blood samples were collected into EDTA tubes at different time points: T0.5h, T1h, T3h, T8h, T24h (Day 1), T48h (Day 2), T96h (Day 4), T168h (Day 7), T240h (Day 10), T336h (Day 14). Blood samples were centrifuged and the plasma from each time point was retained. The plasma samples were analysed by LC/MS/MS for quantifying meloxicam content.

Some parameters, for example the mass of formulation, the animal model, or the needle size may be adapted depending on the studied API, its intended medical use and its targeted dose and release duration. Set-ups with different parameters are presented in Table 5 below.

TABLE 5

| In vivo set-up Number | Procedure | | | Animal | | |
|---|---|---|---|---|---|---|
| | Syringe | Needle | Injection volume (µL) | Model | Injection site | Route of administration |
| 1 | 1 mL luer lock soft ject ® | 23G (1" 0.6 × 25 mm) Terumo ® | 160 | Rat | Intrascapular | Subcutaneous |
| 2 | 1.5 mL luer lock Terumo | 21G (1" 0.80 × 25 mm) Terumo ® | 1700 | Minipig | Axillary | Subcutaneous |
| 3 | 1 mL luer lock soft ject ® | 23G (1" 0.6 × 30 mm) Terumo ® | 180 | Rat | Intrascapular | Subcutaneous |

Embodiments of the invention are set out below with reference to the following numbered paragraphs (paras):

1. A pharmaceutical composition suitable for generating an in situ depot comprising: a biodegradable multi-branched copolymer comprising at least three polyester arms attached to a central core which comprises a polyether, and wherein the multi-branched copolymer is substantially insoluble in aqueous solution.

2. The composition according to para 1, wherein the molecular weight of the polyether is 10 kDa or less, preferably 5 kDa or less, 4 kDa or less, 3 kDa or less, or 2 kDa or less.

3. A pharmaceutical composition suitable for generating an in situ depot comprising:

a biodegradable polyester multi-branched copolymer comprising at least three polyester arms attached to a central core which comprises a polyether, and wherein the molecular weight of the polyether is 10 kDa or less, preferably 5 kDa or less, 4 kDa or less, 3 kDa or less, or 2 kDa or less 4. The composition according to para 3, wherein the multi-branched copolymer is substantially insoluble in aqueous solution.

5. The composition according to any preceding para, wherein the multi-branched copolymer has less than 15 mg/mL, optionally less than 10 mg/mL, less than 5 mg/mL, less than 5 g/mL, less than 2 mg/mL, or less than 1 mg/mL solubility in aqueous solution.

6. The composition according to para 5, wherein solubility is measured at 37° C.

7. The composition according to any preceding para, wherein the multi-branched copolymer is of formula $A(B)_n$ wherein A represents the central core and B represents the polyester arms and n is an integer of at least 3.

8. The composition according to para 7, wherein n is at least 4, or at least 6, or at least 8.

9. The composition according to any preceding para, wherein the central core is a multi-branched polyether which is derivable from poly(ethylene glycol) (PEG) and a polyol.

10. The composition according to para 9 wherein the polyol comprises at least three hydroxyl groups.

11. The composition according to para 10, wherein the polyol is a hydrocarbon substituted with at least three hydroxyl groups, optionally 3, 4, 5, 6, or 8 hydroxyl groups.

12. The composition according to any of paras 9 to 11 wherein the polyol further comprises one or more ether groups.

13. The composition according any of paras 9 to 12, wherein the polyol is pentaerythritol (PE), dipentaerythritol (DPE), trimethylolpropane (TMP), glycerol, hexaglycerol, erythritol, xylitol, di(trimethylolpropane) (diTMP), sorbitol, or inositol.

14. The composition according to any of paras 9 to 13 wherein each branch of the multi-branched polyether has a terminal reactive group capable of reacting with a polyester or monomer or precursor thereof.

15. The composition of para 14, wherein the terminal reactive group is a hydroxyl group.

16. The composition according to any of paras 9 to 15, wherein the multi-branched polyether has Formula 1a or Formula 2a:

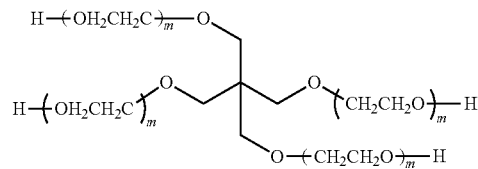

Formula 1a wherein m is an integer between 5 and 150

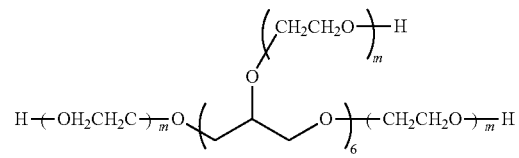

Formula 2a wherein m is an integer between 5 and 150

17. The composition according to any preceding para, wherein the polyester is or is formed from at least one polymer or copolymer selected from the group of poly(lactic acid) (PLA), poly(glycolic acid), poly(epsilon-caprolactone), poly(ethylene adipate), poly(lactic acid-co-glycolic acid) (PLGA) and poly(hydroxyalkanoate) or mixtures thereof.

18. The composition according to any preceding para, wherein the polyester is a homopolymer.

19. The composition according to any one of paras 1 to 17, wherein the polyester is derived from more than one monomer.

20. The composition according to para 19, wherein when the polyester is derived from more than one monomer, the polyester is a random copolymer or a block copolymer.

21. The composition according to any preceding para, wherein the polyester is or comprises PLA.

22. The composition of para 21, wherein the multi-branched copolymer is obtainable by reacting a multi-branched polyether as defined in any of paras 9 to 13 with D,L-lactide.

23. The composition of para 22, where the multi-branched copolymer is obtainable by ring-opening polymerisation of the D,L-lactide initiated by the multi-branched polyether.

24. The composition of para 23, wherein the multi-branched copolymer has Formula 5:

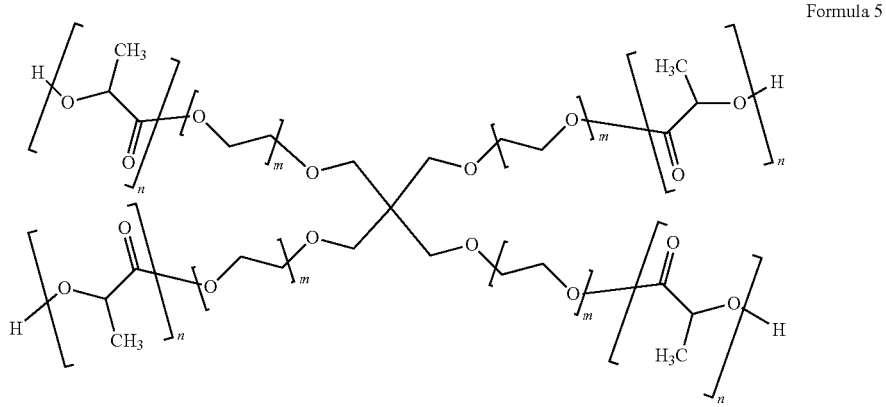

Formula 5 wherein n is an integer between 10 to 200 and m is an integer between 5 and 150.

25. The composition according to any preceding para, wherein the number of polyester repeat units in each arm is independently in the range of 10 to 200.

26. A composition according to any preceding para, wherein the mass of the polyether ranges from 500 g/mol to 40 kg/mol, optionally 500 g/mol to 20 kg/mol, optionally 10 kg/mol to 40 kg/mol, preferably 2 kg/mol to 10 kg/ml.

27. The composition according to any preceding para, further comprising a pharmaceutically acceptable vehicle, optionally wherein the pharmaceutically acceptable vehicle is an organic solvent.

28 The composition according to para 27, wherein the pharmaceutically acceptable vehicle is selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin, glycofurol, and mixtures thereof.

29. The composition according to any preceding para, further comprising at least one pharmaceutically active ingredient.

30. The composition according to para 29, wherein the pharmaceutically active ingredient is hydrophobic.

31. The composition according to para 29, wherein the pharmaceutically active ingredient is meloxicam, bupivacaine, tamsulosin, or combinations thereof.

32. The composition according to any one of paras 29 to 31, wherein the at least one pharmaceutically active ingredient is present in an amount of from 0.05% to 60%, optionally 0.05% to 40%, optionally 0.05% to 30%, optionally 0.05% to 10%, optionally 0.05% to 7%, optionally 0.05% to 2% (w/w %) of the total composition.

33. The composition according to any preceding para, wherein the composition is an injectable liquid.

34. The composition according to any preceding para, wherein the multi-branched copolymer is present in an amount of 2% to 80%, optionally 2% to 70%, optionally 2% to 60%, optionally 10% to 60%, optionally 10% to 50%, optionally 20% to 40%, optionally 20% to 35%, optionally 30% to 50% (w/w %) of the total composition.

35. The composition according to any preceding para, wherein the polyester repeat unit to ethylene oxide molar ratio in the composition is from 1 to 10.

36. The composition according to any preceding para, wherein the release of at least one active ingredient can be modulated.

37. The composition according to any preceding para, which is suitable to deliver a pharmaceutically active ingredient to a subject for at least 1 day, optionally at least 3 days, optionally at least 7 days, optionally at least 30 days, optionally at least 90 days, optionally at least 1 year.

38. Use of the pharmaceutical composition according to any of paras 1 to 37 to modulate the kinetics of release of at least one active ingredient.

39. A method of producing a pharmaceutical composition of any one of paras 1 to 37, said method comprising dissolving a multi-branched copolymer as defined in any of paras 1 to 35 in a pharmaceutically acceptable vehicle.

40. The method of para 39, further comprising adding a pharmaceutically active ingredient to the composition.

41. A biodegradable depot which is produced ex vivo or in situ by contacting the composition as defined in any of paras 1 to 37 with an aqueous medium, water or body fluid.

42. A method for the controlled release of a pharmaceutically active ingredient comprising administering the composition of any one of paras 1 to 37 and allowing an in situ depot to be formed in vivo.

The invention claimed is:

1. A pharmaceutical composition comprising:
at least one pharmaceutically active ingredient and a biodegradable multi-branched copolymer comprising at least three polyester arms attached to a central core which comprises a polyether, wherein the central core is a multi-branched polyether which is poly(ethylene glycol) (PEG) and a polyol and the polyether is 10 kDa or less, the polyester is or comprises PLA, wherein the PLA is or comprises PDLLA, the multi-branched copolymer having the formula $A(B)_n$ wherein A represents the central core, B represents the polyester arms and n is an integer of at least 3, wherein the multi-branched copolymer is substantially insoluble in aqueous solution; and
a biocompatible organic solvent in an amount at least 25% (w/w %) of the total composition.

2. The composition according to claim 1, wherein the molecular weight of the polyether is 5 kDa or less, 4 kDa or less, 3 kDa or less, 2 kDa or less, 1 kDa or less, or 0.5 kDa or less.

3. The composition according to claim 1, wherein the multi-branched copolymer has less than 15 mg/mL, less than 10 mg/mL, less than 5 g/mL, less than 2 mg/mL, or less than 1 mg/mL solubility in aqueous solution, when measured at 37° C.

4. The composition according to claim 1 which forms an in-situ depot.

5. The composition according to claim 1, wherein n is at least 4, at least 6, at least 8, or n is 4.

6. The composition according to claim 2, wherein n is at least 4, at least 6, at least 8, or n is 4.

7. The composition according to claim 1, wherein the polyol is a hydrocarbon substituted with at least three hydroxyl groups.

8. The composition according to claim 1 wherein the polyol further comprises one or more ether groups.

9. The composition according to claim 1, wherein the polyol is pentaerythritol (PE), dipentaerythritol (DPE), trimethylolpropane (TMP), glycerol, hexaglycerol, erythritol, xylitol, di(trimethylolpropane) (diTMP), sorbitol, or inositol.

10. The composition according to claim 1, wherein each branch of the multi-branched polyether has a terminal reactive group capable of reacting with a polyester or monomer or precursor thereof.

11. The composition of claim 10, wherein the terminal reactive group is a hydroxyl group.

12. The composition according to claim 1, wherein the polyester further comprises at least one polymer or copolymer selected from the group of poly(glycolic acid) (PGA), poly(epsilon-caprolactone) (PCL), poly(ethylene adipate) (PEA), poly(lactic acid-co-glycolic acid) (PLGA) and poly(hydroxyalkanoate) (PHA).

13. The composition according to claim 1, wherein the polyester is a homopolymer.

14. The composition according to claim 1, wherein the polyester is derived from more than one monomer.

15. The composition according to claim 14, wherein when the polyester is derived from more than one monomer, the polyester is a random copolymer or a block copolymer.

16. The composition of claim 1, wherein the multi-branched copolymer has Formula 5 or Formula 6 or Formula 7 or Formula 8:

Formula 5

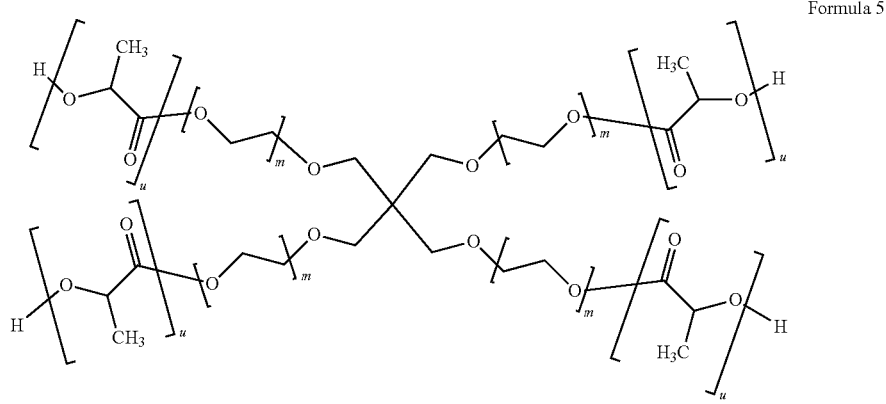

wherein u is an integer between 4 to 200 and m is an integer between 2 and 150

Formula 6

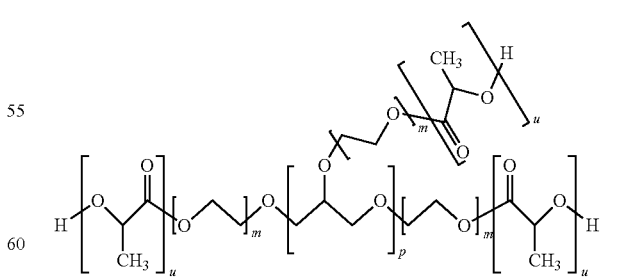

wherein u is an integer between 4 to 200, m is an integer between 2 and 150 and p is 6, Formula 7

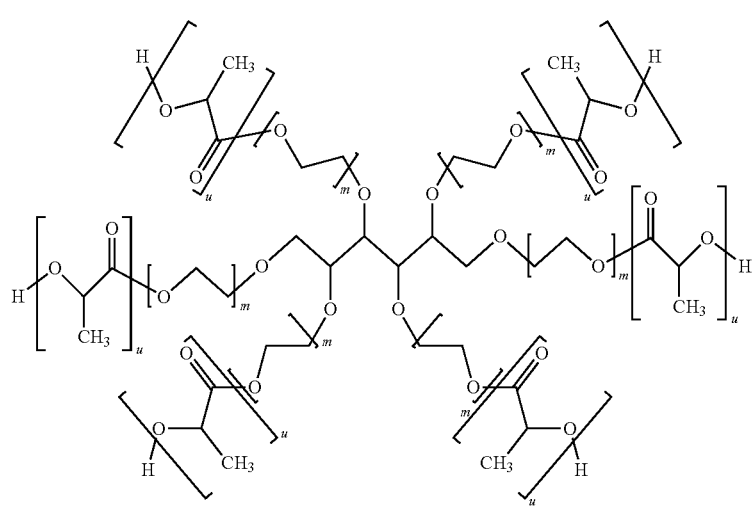

wherein u is an integer between 4 to 200 and m is an integer between 2 and 150,

Formula 8

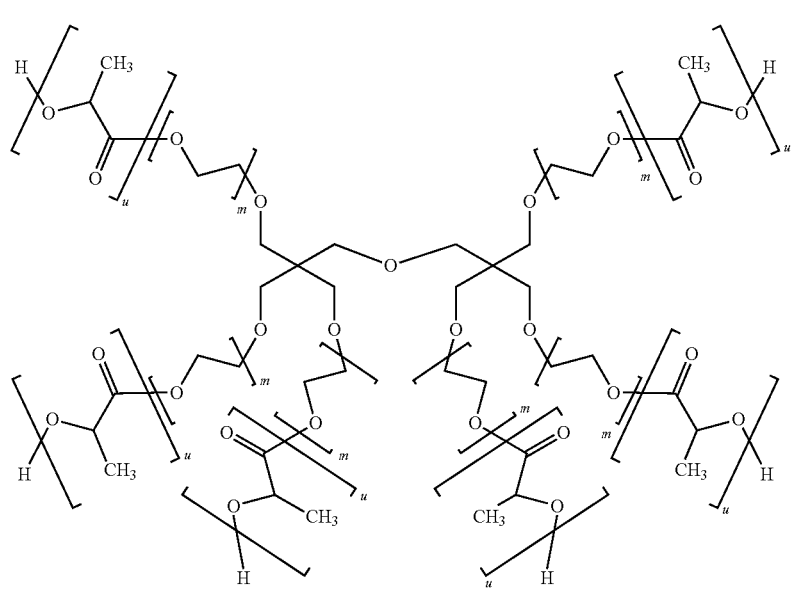

wherein u is an integer between 4 to 200 and m is an integer between 2 and 150.

17. The composition according to claim 1, wherein the number of polyester repeat units in each arm is independently in the range of 4 to 200.

18. A composition according to claim 1, wherein the molecular weight of the polyether ranges from 0.5 kDa to 10 kDa, 1 kDa to 10 kDa, 2 kDa to 10 kDa, 0.5 kDa to 2 kDa, or 2 kDa to 5 kDa.

19. The composition according to claim 1, wherein the ester repeat unit to ethylene oxide molar ratio of the multi-branched copolymer in the composition is from 1 to 10, or from 2 to 6.

20. The composition according to claim 1, the biocompatible organic solvent is at least 35% (w/w %) of the total composition.

21. The composition according to claim 1, wherein the biocompatible organic solvent is selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin, glycofurol, and mixtures thereof.

22. The composition according to claim 1, wherein the pharmaceutically active ingredient is hydrophobic.

23. The composition according to claim 1, wherein the pharmaceutically active ingredient is meloxicam, bupivacaine, tamsulosin, octreotide, tadalafil, empaglifozin, tenofovir, liothyronine, or combinations thereof.

24. The composition according to claim 1, wherein the at least one pharmaceutically active ingredient is present in an amount of from 0.05% to 60%, 0.05% to 40%, 0.05% to 30%, 0.05% to 10%, 0.05% to 7%, or 0.05% to 2% (w/w %) of the total composition.

25. The composition according to claim 1, wherein the multi-branched copolymer is present in an amount of 2% to 80%, 2% to 70%, 2% to 60%, 10% to 60%, 10% to 50%, 20% to 40%, 20% to 35%, or 30% to 50% (w/w %) of the total composition.

26. The pharmaceutical composition of claim 1, wherein the pharmaceutically active ingredient is delivered to a subject for at least 30 days.

27. A method for the controlled release of a pharmaceutically active ingredient comprising administering the composition of claim 1 to a subject.

* * * * *